United States Patent
Nathwani et al.

(10) Patent No.: US 10,842,885 B2
(45) Date of Patent: Nov. 24, 2020

(54) FACTOR IX ENCODING NUCLEOTIDES

(71) Applicant: UCL Business LTD, London (GB)

(72) Inventors: Amit Nathwani, Rickmansworth (GB); Jenny McIntosh, Surrey (GB)

(73) Assignee: UCL Business LTD, Greater London (GB)

(*) Notice: Subject to any disclaimer, the term of this patent is extended or adjusted under 35 U.S.C. 154(b) by 0 days.

(21) Appl. No.: 16/105,583

(22) Filed: Aug. 20, 2018

(65) Prior Publication Data

US 2020/0054767 A1    Feb. 20, 2020

(51) Int. Cl.
| | |
|---|---|
| *C12N 15/63* | (2006.01) |
| *A61K 48/00* | (2006.01) |
| *C07K 14/81* | (2006.01) |
| *A61P 7/00* | (2006.01) |

(52) U.S. Cl.
CPC ...... *A61K 48/0066* (2013.01); *A61K 48/0075* (2013.01); *A61K 48/0091* (2013.01); *A61P 7/00* (2018.01); *C07K 14/8107* (2013.01); *C12Y 304/21022* (2013.01)

(58) Field of Classification Search
None
See application file for complete search history.

(56) References Cited

U.S. PATENT DOCUMENTS

| | | |
|---|---|---|
| 6,271,025 B1 | 8/2001 | Negrier et al. |
| 6,419,921 B1 | 7/2002 | Négrier et al. |
| 6,723,551 B2 | 4/2004 | Kotin et al. |
| 6,800,461 B2 | 10/2004 | Negrier et al. |
| 6,884,616 B1 | 4/2005 | Negrier et al. |
| 8,168,425 B2 | 5/2012 | Gray |
| 8,198,421 B2 | 6/2012 | Samulski |
| 9,764,045 B2 | 9/2017 | Nathwani et al. |
| 2002/0076798 A1* | 6/2002 | Miao ................ A61K 48/00 435/226 |
| 2002/0086427 A1 | 7/2002 | Leiden et al. |
| 2003/0022378 A1 | 1/2003 | Ehrhardt et al. |
| 2003/0130221 A1 | 7/2003 | High et al. |
| 2003/0148506 A1 | 8/2003 | Kotin et al. |
| 2003/0186291 A1* | 10/2003 | Faust ................ C12N 9/22 435/6.18 |
| 2004/0053870 A1 | 3/2004 | Yew et al. |
| 2007/0003521 A1 | 1/2007 | Yew |
| 2007/0180546 A1 | 8/2007 | Rapp et al. |
| 2008/0102115 A1 | 5/2008 | Oyhenart et al. |
| 2008/0153156 A1* | 6/2008 | Gray ................ A61K 48/0066 435/320.1 |
| 2008/0167219 A1 | 7/2008 | Lin et al. |
| 2008/0269125 A1 | 10/2008 | Ballance et al. |
| 2008/0305991 A1 | 12/2008 | Defrees et al. |
| 2011/0070241 A1 | 3/2011 | Yang |
| 2012/0009222 A1 | 1/2012 | Nguyen et al. |
| 2013/0236974 A1 | 9/2013 | De Fougerolles |
| 2014/0271550 A1 | 9/2014 | Rabinowitz et al. |
| 2016/0122739 A1 | 5/2016 | Sheehan et al. |
| 2016/0222414 A1 | 8/2016 | Rabinowitz et al. |
| 2016/0361427 A1 | 12/2016 | Defrees et al. |
| 2016/0375110 A1 | 12/2016 | High et al. |
| 2017/0136104 A1 | 5/2017 | Defrees et al. |

FOREIGN PATENT DOCUMENTS

| | | |
|---|---|---|
| CN | 201610898732 | 10/2016 |
| EP | 1010762 A1 | 6/2000 |
| EP | 1026250 A1 | 8/2000 |
| EP | 1038959 A1 | 9/2000 |
| EP | 1048726 A2 | 11/2000 |
| EP | 1048736 A1 | 11/2000 |
| EP | 1048735 B1 | 9/2006 |
| EP | 2067488 A1 | 6/2009 |
| EP | 2149603 A1 | 2/2010 |
| EP | 2492347 A1 | 8/2012 |
| EP | 2216409 B1 | 12/2014 |
| WO | WO-1994017810 A1 | 8/1994 |
| WO | WO-9742900 A1 | 11/1997 |
| WO | WO-9841240 A1 | 9/1998 |
| WO | WO-9903496 A1 | 1/1999 |
| WO | WO-9949803 A1 | 10/1999 |
| WO | WO-1999049880 A1 | 10/1999 |
| WO | WO-0014262 A2 | 3/2000 |
| WO | WO-2000049147 A1 | 8/2000 |
| WO | WO-0136620 A2 | 5/2001 |
| WO | WO-0166149 A2 | 9/2001 |
| WO | WO-0170763 A1 | 9/2001 |
| WO | WO-2001070968 A3 | 9/2001 |
| WO | WO-0175092 A2 | 10/2001 |
| WO | WO-0179271 A1 | 10/2001 |
| WO | WO-2001077137 A1 | 10/2001 |
| WO | WO-0198482 A2 | 12/2001 |
| WO | WO-0240544 A2 | 5/2002 |
| WO | WO-2002034296 A1 | 5/2002 |
| WO | WO-02062376 A1 | 8/2002 |
| WO | WO-02062377 A2 | 8/2002 |
| WO | WO-02064799 A2 | 8/2002 |
| WO | WO-02071843 A1 | 9/2002 |
| WO | WO-02079447 A2 | 10/2002 |
| WO | WO-2002099105 A2 | 12/2002 |
| WO | WO-03020764 A2 | 3/2003 |
| WO | WO-03025146 A2 | 3/2003 |
| WO | WO-03048364 A2 | 6/2003 |

(Continued)

OTHER PUBLICATIONS

Score result for instant SEQ ID No. 13 for Miao & Kay and Gray (Year: 2019).*

(Continued)

*Primary Examiner* — Catherine S Hibbert
(74) *Attorney, Agent, or Firm* — Wilson Sonsini Goodrich & Rosati

(57) ABSTRACT

The present invention relates to polynucleotides comprising a Factor IX nucleotide sequence, wherein the Factor IX nucleotide sequence comprises a coding sequence that encodes a Factor IX protein or fragment thereof and wherein a portion of the coding sequence is not wild type. The present invention further relates to viral particles comprising a recombinant genome comprising the polynucleotide of the invention, compositions comprising the polynucleotides or viral particles, and methods and uses of the polynucleotides, viral particles or compositions.

24 Claims, 13 Drawing Sheets

Specification includes a Sequence Listing.

(56) References Cited

FOREIGN PATENT DOCUMENTS

| | | |
|---|---|---|
| WO | WO-2004027019 A2 | 4/2004 |
| WO | WO-2004080162 A2 | 9/2004 |
| WO | WO-2004092351 A2 | 10/2004 |
| WO | WO-2004098532 A2 | 11/2004 |
| WO | WO-2005040215 A2 | 5/2005 |
| WO | WO-2005084430 A1 | 9/2005 |
| WO | WO-2006015789 A3 | 2/2006 |
| WO | WO-2006018204 A1 | 2/2006 |
| WO | WO-2006026238 A2 | 3/2006 |
| WO | WO-2006036502 A2 | 4/2006 |
| WO | WO-2006093847 A1 | 9/2006 |
| WO | WO-2006103258 A1 | 10/2006 |
| WO | WO-2006110689 A2 | 10/2006 |
| WO | WO-2006127896 A2 | 11/2006 |
| WO | WO-2007036233 A2 | 4/2007 |
| WO | WO-2007046703 A2 | 4/2007 |
| WO | WO-2007047706 A2 | 4/2007 |
| WO | WO-2007120533 A2 | 10/2007 |
| WO | WO-2007130453 A2 | 11/2007 |
| WO | WO-2007135182 A2 | 11/2007 |
| WO | WO-2007148971 A2 | 12/2007 |
| WO | WO-2007149406 A2 | 12/2007 |
| WO | WO-2007149852 A2 | 12/2007 |
| WO | WO-2008091311 A1 | 7/2008 |
| WO | WO-2008092643 A2 | 8/2008 |
| WO | WO-2008092644 A2 | 8/2008 |
| WO | WO-2008124724 A1 | 10/2008 |
| WO | WO-2008153366 A2 | 12/2008 |
| WO | WO-2009014445 A2 | 1/2009 |
| WO | WO-2009026393 A2 | 2/2009 |
| WO | WO-2009038462 A1 | 3/2009 |
| WO | WO-2009051717 A2 | 4/2009 |
| WO | WO-2009059056 A2 | 5/2009 |
| WO | WO-2009061369 A2 | 5/2009 |
| WO | WO-2009102085 A1 | 8/2009 |
| WO | WO-2009130198 A2 | 10/2009 |
| WO | WO-2009137254 A2 | 11/2009 |
| WO | WO-2009140015 A2 | 11/2009 |
| WO | WO-2008118507 A3 | 12/2009 |
| WO | WO-2010012451 A1 | 2/2010 |
| WO | WO-2010029178 A1 | 3/2010 |
| WO | WO-2010055413 A1 | 5/2010 |
| WO | WO-2011005968 A1 | 1/2011 |
| WO | WO-2011011841 A1 | 2/2011 |
| WO | WO-2011014890 A1 | 2/2011 |
| WO | WO-2011054994 A1 | 5/2011 |
| WO | WO-2011122950 A1 | 10/2011 |
| WO | WO-2011154520 A1 | 12/2011 |
| WO | WO-2012061654 A1 | 5/2012 |
| WO | WO-2012135805 A2 | 10/2012 |
| WO | WO-2012170930 A1 | 12/2012 |
| WO | WO-2013090648 A1 | 6/2013 |
| WO | WO-2013173512 A2 | 11/2013 |
| WO | WO-2014016580 A1 | 1/2014 |
| WO | WO-2014063108 A1 | 4/2014 |
| WO | WO-2014063753 A1 | 5/2014 |
| WO | WO-2014064277 A1 | 5/2014 |
| WO | WO-2014070349 A1 | 5/2014 |
| WO | WO-2014081831 A1 | 5/2014 |
| WO | WO-2014152940 A1 | 9/2014 |
| WO | WO-2014182684 A2 | 11/2014 |
| WO | WO-2014193716 A2 | 12/2014 |
| WO | WO-2015012924 A2 | 1/2015 |
| WO | WO-2015013313 A2 | 1/2015 |
| WO | WO-2015038625 A1 | 3/2015 |
| WO | WO-2015073988 A1 | 5/2015 |
| WO | WO-2015085276 A1 | 6/2015 |
| WO | WO-2015086406 A2 | 6/2015 |
| WO | WO-2015139093 A1 | 9/2015 |
| WO | WO-2015162302 A2 | 10/2015 |
| WO | WO-2016004113 A1 | 1/2016 |
| WO | WO-2016028872 A2 | 2/2016 |
| WO | WO-2016041588 A1 | 3/2016 |
| WO | WO-2016073837 A1 | 5/2016 |
| WO | WO-2016075473 A2 | 5/2016 |
| WO | WO-2016075473 A3 | 8/2016 |
| WO | WO-2016123200 A1 | 8/2016 |
| WO | WO-2016127057 A1 | 8/2016 |
| WO | WO-2016146757 A1 | 9/2016 |
| WO | WO-2016168728 A2 | 10/2016 |
| WO | WO-2016179644 A1 | 11/2016 |
| WO | WO-2016181122 A1 | 11/2016 |
| WO | WO-2016181123 A1 | 11/2016 |
| WO | WO-2016210170 A1 | 12/2016 |
| WO | WO-2017021359 A1 | 2/2017 |
| WO | WO-2017024060 A1 | 2/2017 |
| WO | WO-2017070167 A1 | 4/2017 |
| WO | WO-2017075619 A1 | 5/2017 |
| WO | WO-2017083762 A1 | 5/2017 |
| WO | WO-2017083764 A1 | 5/2017 |
| WO | WO-2017093482 A1 | 6/2017 |
| WO | WO-2017096039 A1 | 6/2017 |
| WO | WO-2017180861 A1 | 10/2017 |
| WO | WO-2017191274 A2 | 11/2017 |
| WO | WO-2018199214 A1 | 11/2018 |
| WO | WO-2018206168 A1 | 11/2018 |
| WO | WO-2018213786 A1 | 11/2018 |
| WO | WO-2018217731 A1 | 11/2018 |
| WO | WO-2018222792 A1 | 12/2018 |
| WO | WO-2018222890 A1 | 12/2018 |
| WO | WO-2018226887 A1 | 12/2018 |
| WO | WO-2019011893 A1 | 1/2019 |
| WO | WO-2018022844 A3 | 4/2019 |
| WO | WO-2019067766 A1 | 4/2019 |
| WO | WO-2019079215 A1 | 4/2019 |
| WO | WO-2019094521 A1 | 5/2019 |
| WO | WO-2000054787 A1 | 9/2020 |

OTHER PUBLICATIONS

Monahan et al entitled "Employing a Gain-of-Function Factor IX Variant R338L to Advance the Efficacy and Safety of Hemophilia B Human Gene Therapy: Preclinical Evaluation Supporting an Ongoing Adeno-Associated Virus Clinical Trial" (Human Gene Therapy Feb. 2015 vol. 26: pp. 69-81.) (Year: 2015).*

Score result for instant SEQ ID No. 14 for Miao & Kay and Gray (Year: 2019).*

Bantel-Schaal, et al., Human Adeno-Associated Virus Type 5 is Only Distantly Related to Other Known Primate Helper-Dependent Parvoviruses, Journal of Virology, (1999) vol. 73 (2), pp. 939-947.

Berns, Parvoviridae: The Viruses and Their Replication, Fields Virology; Feb. 7, 2018; pp. 2173-2197.

Cantore, et al., Hyperfunctional coagulation factor IX improves the efficacy of gene therapy inhemophilic mice, Blood, (2012), vol. 120, pp. 4517-4520.

Fagone, et al., Systemic Errors in Quantitative Polymerase Chain ReactionTitration of Self-Complementary Adeno-AssociatedViral Vectors and Improved Alternative Methods, Hum Gene Ther Methods. Feb. 23, 2012 (1):1-7.

Nathwani, et al., Long-term Safety and Efficacy Following Systemic Administration of a Self-complementary AAV Vector Encoding Human FIX Pseudotyped With Serotype 5 and 8 Capsid Proteins, Mol Ther. May 2011, vol. 19. (5), pp. 876-85.

Altschul, et al, Gapped BLAST and PSI-BLAST: a new generation of protein database search programs, Nucleic Acids Research, (1997) Vol, 25(17), pp. 3389-3402.

Altschul, et al, Basic Local Alignment Search Tool, J. Mol. Biol. 215 (1990), pp. 403-410.

Wu, et al., Optimization of Self-complementary AAV Vectorsfor Liver-directed Expression Results in Sustained Correction of Hemophilia B at Low Vector Dose, Mol Ther. Feb. 2008; vol. 16(2), pp. 280-289.

Allan et al. Evolutionary Duplication of a Hepatic Control Region in the Human Apolipoprotein E Gene Locus. The Journal of Biological Chemistry, vol. 270(44):26278-26281, (Nov. 3, 1995).

Anson et al. The gene structure of human anti-haemophilic factor IX. The EMBO Journal 3(5):1053-1060 (1984).

(56) References Cited

OTHER PUBLICATIONS

Arruda et al. Emerging therapies for haemophilia: controversies and unanswered questions [version 1; referees: 4 approved]. F1000Research 2018, 7(F1000 Faculty Rev):489 Last updated: Apr. 24, 2018.
Arruda et al. Safety and efficacy of factor IX gene transfer to skeletal muscle in murine and canine hemophilia B models by adeno-associated viral vector serotype 1. Blood 103(1):85-92 (Jan. 1, 2004).
Chang et al. Changing Residue 338 in Human Factor IX from Arginine to Alanine Causes an Increase in Catalytic Activity. The Journal of Biological Chemistry, 273(20):12089-12094 (May 15, 1998).
Chiorini J.A. et al. Cloning of adeno-associated virus type 4 (AAV4) and generation of recombinant AAV4 particles. Journal of Virology, 71:6823-6833 (1997).
Chiorini, J.A. Ja et al. Cloning and characterization of adeno-associated virus type 5, Journal of Virology 73:1309-1319 (1999).
Dang, et al. In Vivo Footprinting Analysis of the Hepatic Control Region of the Human Apolipoprotein E/C-I/C-IV/C-II Gene Locus. The Journal of Biological Chemistry, 271(45): 28667-28676 (Nov. 8, 1996).
Dang et al. Structure of the Hepatic Control Region of the Human Apolipoprotein E/C-I Gene Locus. The Journal of Biological Chemistry, 270(38):22577-22585 (Sep. 22, 1995).
Enjolras et al. The Three In-frame ATG, Clustered in the Translation Initiation Sequence of Human Factor IX Gene, are Required for an Optimal Protein Production. Thrombosis and Haemostasis, Schattauer GMBH Germany, 82(4):1264-1269 (Oct. 1, 1999).
George et al. Hemophilia B Gene Therapy with a High-Specific-Activity Factor IX Variant. The New England Journal of Medicine, 377(23):2215-2227 (Dec. 7, 2017).
Giannelli et al. Haemophilia B: database of point mutations and short additions and deletions, Oxford University Press, Nucleic Acids Research, 18(14):4053-4059 (1990).
Haas et al. Codon usage limitation in the expression of HIV-1 envelope glycoprotein, Current Biology 6(3):315-324 (1996).
Hafenrichter et al. Quantitative Evaluation of Liver-Specific Promoters From Retroviral Vectors After In Vivo Transduction of Hepatocytes, Blood, 84(10):3394-3404 (Nov. 15, 1994).
Ketterling et al. The Rates of G:C- > T:A and G:C- > C:G Transversions at CpG Dinucleotides in the Human Factor IX Gene, Am. J. Hum. Genet. 54:831-835(1994).
Kurachi et al. Role of Intron I in Expression of the Human Factor IX Gene, Journal of Biological Chemistry, American Society for Biochemistry and Molecular Biology, US, 270(10):5276-5281(Mar. 10, 1995).
Lu et al. Gene therapy for hemophilia B mediated by recombinant adeno-associated viral vector with hFIXR338A, a high catalytic activity mutation of human coagulation factor IX, Science in China (Series C), 44(6):585-592(Dec. 2001).
Mathur et al. Protease and EGF1 Domains of Factor IXa Play Distinct Roles in Binding to Factor VIIIa, The Journal of Biological Chemistry, 274(26):18477-18486 (Jun. 25, 1999).
McIntosh J. et al. Therapeutic levels of FVIII following a single peripheral vein administration of rAAV vector encoding a novel human factor VIII variant. Blood 121(17):3335-44 (Apr. 25, 1993).
Miao, C.H. et al. Inclusion of the hepatic locus control region, an intron, and untranslated region increases and stabilizes hepatic factor IX gene expression in vivo but not in vitro. Mol Ther. 1(6):522-32(Jun. 2000).
Nathwani, A.C. et al. Self-complementary adeno-associated virus vectors containing a novel liver-specific human factor IX expression cassette enable highly efficient transduction of murine and nonhuman primate liver. Blood, 107(7): 2653-2661 (Apr. 1, 2006).
Nathwani et al. Adenovirus-Associated Virus Vector-Mediated Gene Transfer in Hemophilia B. New England Journal of Medicine, 365(25):2357-65 (Dec. 22, 2011).
Nathwani et al. Our Journey to Successful Gene Therapy for Hemophilia B, Human Gene Therapy, 25(11):923-926 (Nov. 1, 2014).
Needleman, S.B. et al. A general method applicable to the search for similarities in the amino acid sequence of two proteins. Journal Molecular Biology 48(3):443-53 (Mar. 1970).
Okuyama T. et al. Liver-directed gene therapy: a retroviral vector with a complete LTR and the ApoE enhancer-alpha 1-antitrypsin promoter dramatically increases expression of human alpha 1-antitrypsin in vivo. Human Gene Therapy 7(5):637-45 (Mar. 20, 1996).
Rodriguez et al. Biosynthesis of FVIII in megakaryocytic cells: improved production and biochemical characterization, Blackwell Publishing Ltd, British Journal of Haematology, 127:568-575 (2004).
Rutledge, E.A. et al. Infectious clones and vectors derived from adeno-associated virus (AAV) serotypes other than AAV type 2. Journal of Virology 72:309-319 (1998).
Sabatino et al. Novel hemophilia B mouse models exhibiting a range of mutations in the Factor IX gene, Blood, 104(9): 2767-2774 (Nov. 1, 2004).
Schuettrumpf et al. Factor IX variants improve gene therapy efficacy for hemophilia B, Blood, 105(6):2316-2323 (Mar. 15, 2005).
Simioni et al. Evidence of the first X-linked thrombophilia due to a novel mutation in clotting factor IX gene resulting in hyperfunctional fix: factor IX arginine 338 leucine (factor IX padua), 2009 The Authors. Journal Compilation. International Society on Thrombosis and Haemostasis 7 (Suppl. 2). Abstract PL-TU-0004.
Simioni et al. X-Linked Thrombophilia with a Mutant Factor IX (Factor IX Padua). New England Journal of Medicine 361:1671-5(2009).
Srivastava, A. et al. Nucleotide sequence and organization of the adeno-associated virus 2 genome, Journal of Virology 45(2): 555-64(Feb. 1983).
Wang et al. Sustained correction of bleeding disorder in hemophilia B mice by gene therapy. Proc Natl Acad. Sci. USA 96(7): 3906-3910 (Mar. 30, 1999).
Welch et al. You're one in a googol: optimizing genes for protein expression, J.R. Soc. Interface 6(Suppl. 4):S467-76(Aug. 9, 2009). E-published: Mar. 11, 2009.
Wooddell et al. Sustained liver-specific transgene expression from the albumin promoter in mice following hydrodynamic plasmid DNA delivery. The Journal of Gene Medicine, 10: 551-563 (2008).
Wu, P. et al. Mutational analysis of the adeno-associated virus type 2 (AAV2) capsid gene and construction of AAV2 vectors with altered tropism. Journal of Virology, 74(18):8635-47 (Sep. 2000).
Yan et al. Transgenic Mice Can Express Mutant Human Coagulation Factor IX with Higher Level of Clotting Activity. Biochemical Genetics, 44(7/8):349-360 (Aug. 2006).
Bryan et al., 2013, http://www.elsevierblogs.com/currentcomments/?p=962, Implications of protein fold switching, pp. 1-4.
Dunbar et al., 2018, Gene therapy comes of age, Science, vol. 359, eaan4672, pp. 1-10.
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.
Shim et al., 2017, Nonviral Delivery Systems for Cancer Gene Therapy: Strategies and Challenges, Current Gene Therapy, vol. 17, No. 5, pp. 1-18.
Suwanmanee et al., 2014, Molecular Therapy, Integration-deficient lentiviral vectors expressing codon-optimized R338L human FIX restore normal hemostasis in Hemophilia B mice, vol. 22, No. 3, pp. 567-574.
Kaur et al., 2009, Addressing the Challenge: Current and Future Directions in Ovarian Cancer Therapy, Current Gene Therapy, vol. 9, pp. 434-458.
Maqbool et al., 2015, The substrate-binding protein in bacterial ABC transporters: dissecting roles in the evolution of substrate specificity, Biochemical Society Transactions, vol. 43, No. 5, pp. 1011-1017.
Plantier et al., 2001, Thromb Haemost, A factor VIII minigene comprising the truncated intron I of factor IX highly improves the in vitro production of factor VIII, 86(2), pp. 596-603.
Paul E. Monahan et al., "Employing a Gain-of-Function Factor IX Variant R338L to Advance the Efficacy and Safety of Hemophilia B Human Gene Therapy: Preclinical Evaluation Supporting an Ongoing Adeno-Associated Virus Clinical Trial", Human Gene Therapy 26:69-81 (Feb. 2015), DOI: 10.1089/hum.2014.106.

(56) References Cited

OTHER PUBLICATIONS

"Satya et al., 2003 "A Pattern Matching Algorithm for Codon Optimization and CpG Motif-Engineering in DNA Expression Vectors" Proceeding IEEE Computer Society Bioninformatic Conference, 2003 pp. 294-305 vol. 2".

"Bauer et al., 2010 "The impact of intragenic CpG content on gene expression" Nucleic Acids Research, Jul. 2010, vol. 38, pp. 3891-3908".

"Binny et al., 2012 "Vector Systems for Prenatal Gene Therapy: Principles of Adeno-Associated Virus Vector Design and Production" Methods in Molecular Biology, Apr. 25, 2012 pp. 109-131 vol. 891".

"Chen et al., 2005 "Improved Production and Purification of Minicircle DNA Vector Free of Plasmid Bacterial Sequences and Capable of Persistent Transgene Expression in Vivo" Human Gene Therapy, Jan. 2005 pp. 126-131 vol. 16 No. 1".

"Database UniProt [Online] May 10, 2017 (May 10, 2017), "SubName:Full=coagulation factor IX isoform X2 {ECO:00003131RefSeq:XP 008059975.1};", XP002796360, retrieved from EBI accession No. UNIPROT:A0A1U7TQC."

"Faust et al., 2013a "CpG-depleted adeno-associated virus vectors evade immune detection" Journal of Clinical Investigation, Jul. 1, 2013 pp. 2994-3001 vol. 123 No. 7".

"Frumkin et al., 2018 "Codon usage if highly expressed genes affects proteomewide translation efficency" PNAS, May 7, 2018 pp. E4940-E4949 vol. 115 No. 21".

"Hodges et al., 2004 "Long-term Transgene Expression From a Plasmid DNS Gene Therapy Vectors is Negatively Affected by CpG Dinucleotides" Molecular Therapy, Apr. 2004 pp. 269-278 vol. 10 No. 2".

"Kao C Yet al., 2013 "Incorporation of the factor IX Padua mutation into FIX-Triple improves clotting activity in vitro and in vivo" Thrombosis and Haemostasis, May 16, 2013 pp. 244-256 vol. 110 No. 2".

"Krinner et al., 2014 "CpG domains downstream of TSSs promote high levels of gene expression" Nucleic Acids Research, Apr. 2014, vol. 42, pp. 3551-3564".

"Nair et al., 2011 "Effect of different UCOE-promoter combinations in creation of engineered cell lines for the production of Factor VIII" BMC Research Notes, Jun. 10, 2011 vol. 4 Art. 178".

"Pierce & Iorio 2018 "Past, present and future of haemophilia gene therapy: From vectors and transgenes to known and unknown outcomes" Haemophilia, May 21, 2018 pp. 60-67 vol. 24 Suppl. 6".

"Faust et al., 2013b "Escaping Immune Activation through the Use of CpG-Depleted AAV Vectors" Molecular Therapy, May 2013 pp. S44-S45 vol. 21 Suppl. 1".

"Terry 2016"Shire Kills Baxalta's Hemophilia B Program; Clears Path for BioMarin, Spark Therapeutics and uniQure." BioSpace, Aug. 4, 2016 https://www.biospace.com/article/shire-kills-baxalta-s-hemophilia-b-program-clears-path-for-biomarin-spark-therapeutics-and-uniqure-/".

"Hyde et al., 2008 "CpG-free plasmids confer reduced inflammation and sustained pulmonary gene expression" Nature Biotechnology, Apr. 27, 2008 pp. 549-551 vol. 26".

"Wang et al., 1997"A factor IX-deficient Mouse Model of hemophilia B gene therapy". Proceeding of the National Academy of Sciences of the United States of America, 1997 pp. 11563-11566 vol. 94".

"Yew et al., 2002 "CpG-depleted Plasmid DNA Vectors With Enhanced Safety and Long-Term Gene Expression in Vivo" Molecular Therapy, Jun. 2002 pp. 731-738 vol. 5 No. 6".

Mauro, et al. "Codon Optimization in the Production of Recombinant Biotherapeutics: Potential Risks and Considerations" BioDrugs (2018) 32:69-81.

Inouye et al. "Protein expression of preferred human codon-optimized Gaussia luciferase genes with an artificial open-reading frame in mammalian and bacterial cells." Protein Expression and Purification 128 (2016) 93-100.

\* cited by examiner

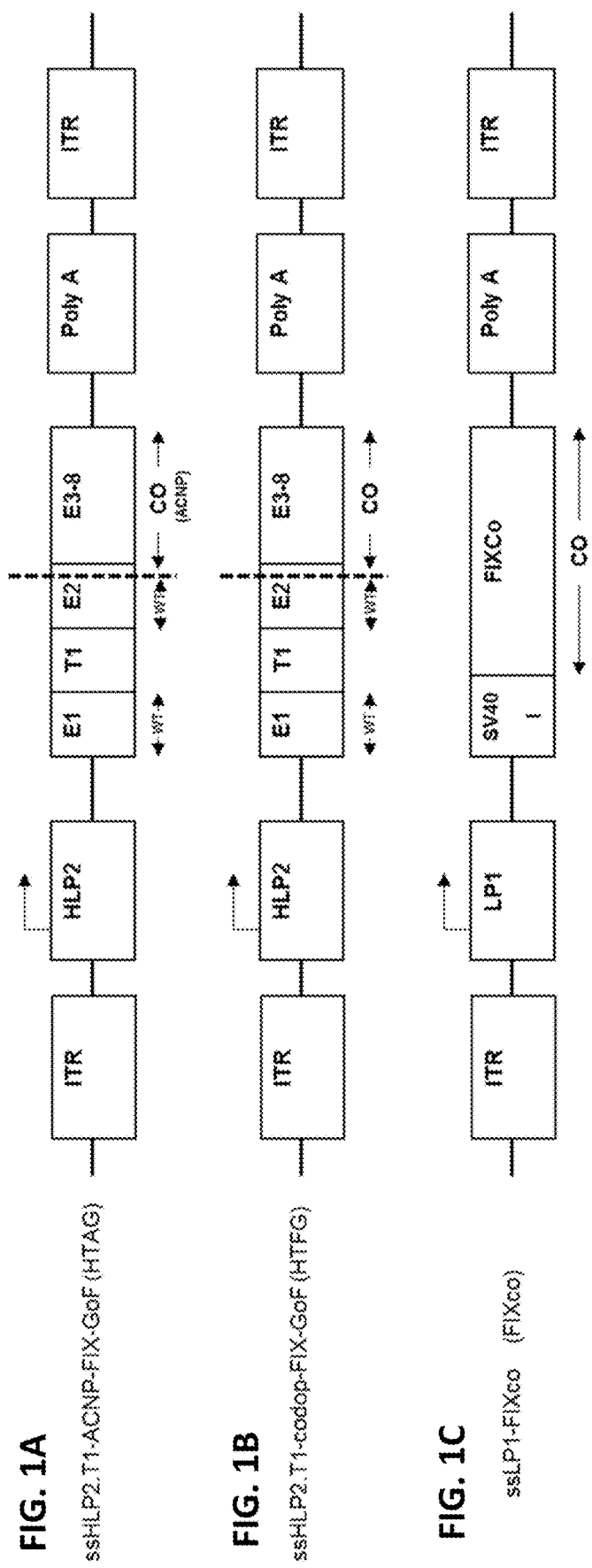

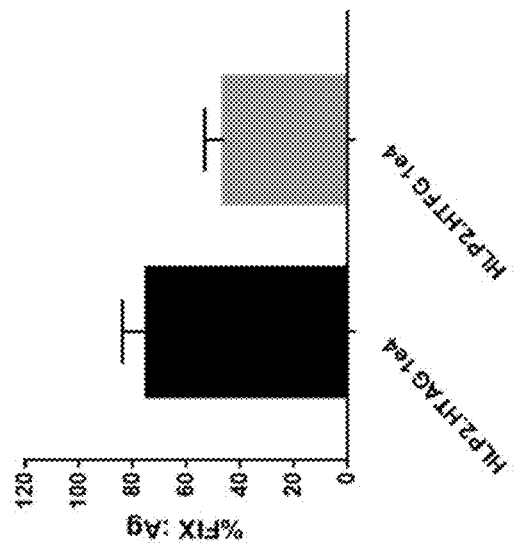
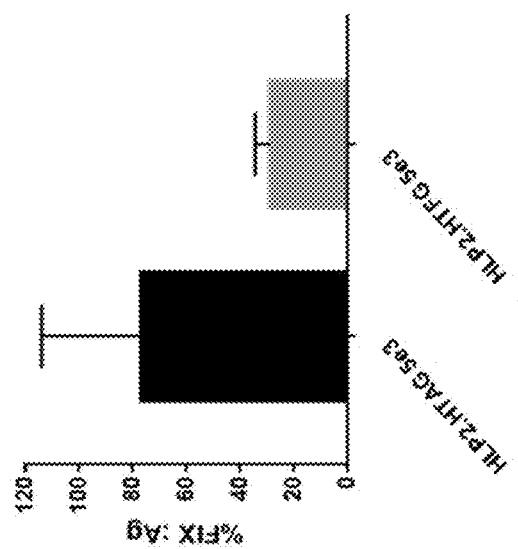
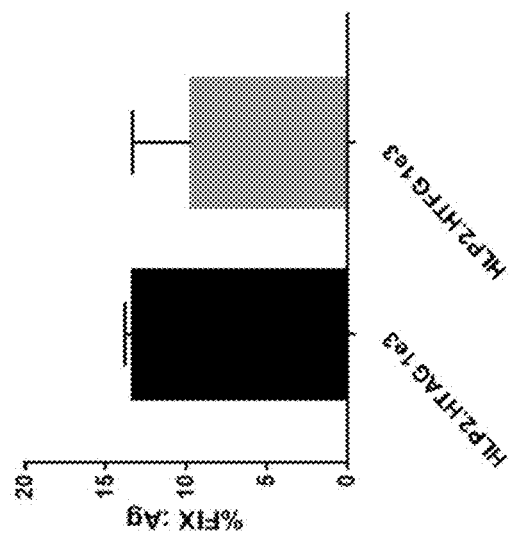

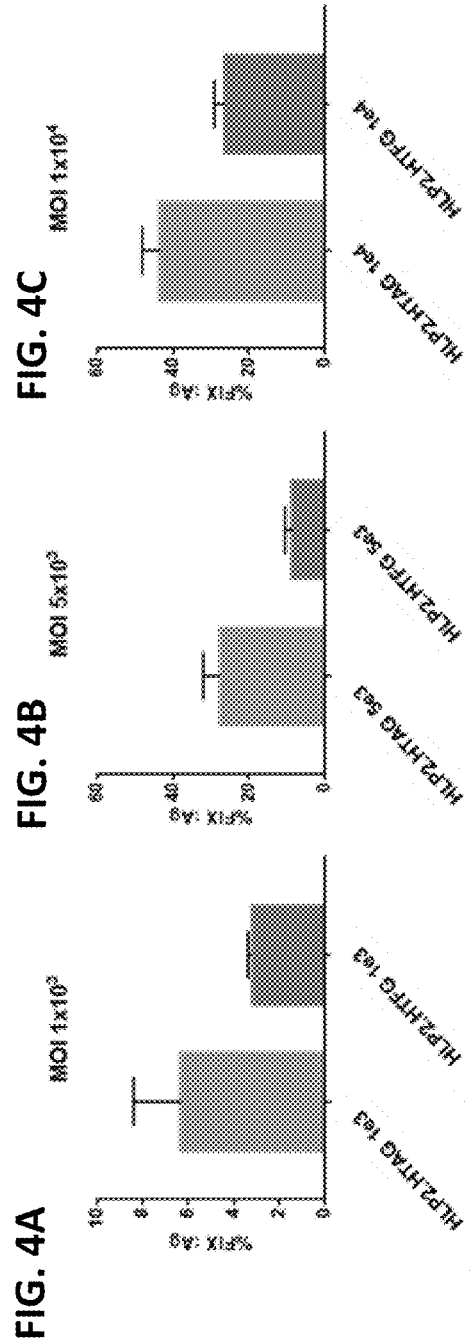
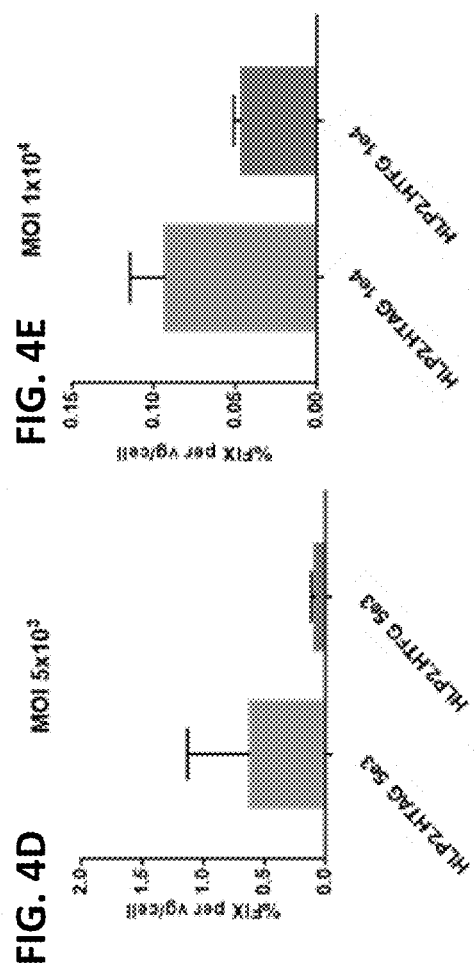

SEQUENCE LISTING

<160> NUMBER OF SEQ ID NOS: 26

<210> SEQ ID NO 1
<211> LENGTH: 1191
<212> TYPE: DNA
<213> ORGANISM: Artificial Sequence
<220> FEATURE:
<223> OTHER INFORMATION: Synthetic construct

<400> SEQUENCE: 1

```
gaggagaagt gcagctttga ggaggccagg gaggtgtttg agaacactga gaggaccact    60
gagttctgga agcagtatgt ggatgggggac cagtgtgaga gcaacccctg cctgaatggg   120
ggcagctgca aggatgacat caacagctat gagtgctggt gccccttttgg ctttgagggc   180
aagaactgtg agctggatgt gacctgcaac atcaagaatg gcagatgtga gcagttctgc   240
aagaactctg ctgacaacaa ggtggtgtgc agctgcactg agggctacag gctggctgag   300
aaccagaaga gctgtgagcc tgctgtgcca ttcccatgtg gcagagtgtc tgtgagccag   360
accagcaagc tgaccagggc tgaggctgtg ttccctgatg tggactatgt gaacagcact   420
gaggctgaaa ccatcctgga acatcacc cagagcaccc agagcttcaa tgacttcacc     480
agggtggtgg ggggggagga tgccaagcct ggccagttcc cctggcaagt ggtgctgaat   540
ggcaaggtgg atgccttctg tgggggcagc attgtgaatg agaagtggat tgtgactgct   600
gcccactgtg tggagactgg ggtgaagatc actgtggtgg ctggggagca caacattgag   660
gagactgagc acactgagca agaggaat gtgatcagga tcatccccca ccacaactac      720
aatgctgcca tcaacaagta caaccatgac attgccctgc tggagctgga tgagcccctg   780
gtgctgaaca gctatgtgac ccccatctgc attgctgaca ggagtacac caacatcttc    840
ctgaagtttg gctctggcta tgtgtctggc tgggggcaggg tgttccacaa gggcaggtct   900
gccctggtgc tgcagtacct gagggtgccc tggtggaca gggccacctg cctgctcagc    960
accaagttca ccatctacaa caacatgttc tgtgctggct tccatgaggg gggcagggac  1020
agctgccagg ggactctgg gggcccccat gtgactgagg tggagggcac cagcttcctg   1080
actggcatca tcagctggg ggaggagtgt gccatgaagg gcaagtatgg catctacacc   1140
aaagtctcca gatatgtgaa ctggatcaag gagaagacca gctgacctg a             1191
```

<210> SEQ ID NO 2
<211> LENGTH: 494
<212> TYPE: DNA
<213> ORGANISM: Artificial Sequence
<220> FEATURE:
<223> OTHER INFORMATION: Synthetic construct

<400> SEQUENCE: 2

```
atgcagcgcg tgaacatgat catggcagaa tcaccaggcc tcatcaccat ctgccttta     60
ggatatctac tcagtgctga atgtacaggt ttgtttcctt ttttaaaata cattgagtat   120
gcttgccttt tagatataga aatatctgat gctgtcttct tcactaaatt ttgattacat   180
gatttgacag caatattgaa gagtctaaca gccagcacgc aggttggtaa gtactgtggg   240
aacatcacag attttggctc catgccctaa agagaaattg ctttcagat tatttggatt    300
aaaaacaaag actttcttaa gagatgtaaa attttcatga tgttttcttt tttgctaaaa   360
ctaaagaatt attcttttac atttcagttt ttcttgatca tgaaaacgcc aacaaaattc   420
tgaatcggcc aaagaggtat aattcaggta aattggaaga gtttgttcaa gggaaccttg   480
agagagaatg tatg                                                     494
```

<210> SEQ ID NO 3
<211> LENGTH: 299
<212> TYPE: DNA
<213> ORGANISM: Artificial Sequence
<220> FEATURE:
<223> OTHER INFORMATION: Synthetic construct

<400> SEQUENCE: 3

```
gtttgtttcc ttttttaaaa tacattgagt atgcttgcct tttagatata gaaatatctg    60
atgctgtctt cttcactaaa ttttgattac atgatttgac agcaatattg aagagtctaa   120
cagccagcac gcaggttggt aagtactgtg gaacatcac agattttggc tccatgccct    180
aaagagaaat tggctttcag attatttgga ttaaaaacaa agactttctt aagagatgta   240
aaatttcat gatgttttct tttttgctaa aactaaagaa ttattctttt acatttcag     299
```

<210> SEQ ID NO 4
<211> LENGTH: 1386
<212> TYPE: DNA
<213> ORGANISM: Artificial Sequence
<220> FEATURE:
<223> OTHER INFORMATION: Synthetic construct

<400> SEQUENCE: 4

```
atgcagcgcg tgaacatgat catggcagaa tcaccaggcc tcatcaccat ctgccttta    60
ggatatctac tcagtgctga atgtacagtt tttcttgatc atgaaaacgc caacaaaatt   120
ctgaatcggc caaagaggta taattcaggt aaattggaag agtttgttca agggaaccctt  180
gagagagaat gtatggagga aagtgcagc tttgaggagg ccagggaggt gtttgagaac    240
actgagagga ccactgagtt ctggaagcag tatgtggatg gggaccagtg tgagagcaac   300
ccctgcctga tgggggcag ctgcaaggat gacatcaaca gctatgagtg ctggtgcccc    360
tttggctttg agggcaagaa ctgtgagctg gatgtgacct gcaacatcaa gaatggcaga   420
tgtgagcagt tctgcaagaa ctctgctgac aacaaggtgg tgtgcagctg cactgagggc   480
tacaggctgg ctgagaacca gaagagctgt gagcctgctg tgccattccc atgtggcaga   540
gtgtctgtga gccagaccag caagctgacc agggctgagg ctgtgttccc tgatgtggac   600
tatgtgaaca gcactgaggc tgaaaccatc ctggacaaca tcacccagag cacccagagc   660
ttcaatgact tcaccagggt ggtgggggg gaggatgcca agcctggcca gttcccctgg   720
caagtggtgc tgaatggcaa ggtggatgcc ttctgtgggg gcagcattgt gaatgagaag   780
tggattgtga ctgctgccca ctgtgtggag actggggtga agatcactgt ggtggctggg   840
gagcacaaca ttgaggagac tgagcacact gagcagaaga ggaatgtgat caggatcatc   900
ccccaccaca actacaatgc tgccatcaac aagtacaacc atgacattgc cctgctggag   960
ctggatgagc cctggtgct gaacagctat gtgacccca tctgcattgc tgacaaggag   1020
tacaccaaca tcttcctgaa gtttggctct ggctatgtgt ctggctgggg cagggtgttc   1080
cacaagggca ggtctgccct ggtgctgcag tacctgaggg tgcccctggt ggacagggcc   1140
acctgcctgc tcagcaccaa gttcaccatc tacaacaaca tgttctgtgc tggcttccat   1200
gagggggca gggacagctg ccaggggac tctgggggcc cccatgtgac tgaggtggag   1260
ggcaccagct tcctgactgg catcatcagc tgggggagg agtgtgccat gaagggcaag   1320
tatggcatct acaccaaagt ctccagatat gtgaactgga tcaaggagaa gaccaagctg   1380
acctga                                                              1386
```

<210> SEQ ID NO 5
<211> LENGTH: 1685
<212> TYPE: DNA
<213> ORGANISM: Artificial Sequence
<220> FEATURE:
<223> OTHER INFORMATION: Synthetic construct

<400> SEQUENCE: 5

```
atgcagcgcg tgaacatgat catggcagaa tcaccaggcc tcatcaccat ctgccttta         60
ggatatctac tcagtgctga atgtacaggt ttgtttcctt ttttaaaata cattgagtat       120
gcttgccttt tagatataga aatatctgat gctgtcttct tcactaaatt ttgattacat       180
gatttgacag caatattgaa gagtctaaca gccagcacgc aggttggtaa gtactgtggg       240
aacatcacag attttggctc catgccctaa agagaaattg ctttcagat tatttggatt        300
aaaaacaaag acttcttaa gagatgtaaa attttcatga tgttttcttt tttgctaaaa        360
ctaaagaatt attcttttac atttcagttt tcttgatca tgaaaacgcc aacaaaattc        420
tgaatcggcc aaagaggtat aattcaggta aattggaaga gtttgttcaa gggaaccttg       480
agagagaatg tatggaggag aagtgcagct tgaggaggc cagggaggtg tttgagaaca        540
ctgagaggac cactgagttc tggaagcagt atgtggatgg ggaccagtgt gagagcaacc       600
cctgcctgaa tggggcagc tgcaaggatg acatcaacag ctatgagtgc tggtgcccct       660
ttggctttga gggcaagaac tgtgagctgg atgtgacctg caacatcaag aatggcagat       720
gtgagcagtt ctgcaagaac tctgctgaca caaggtggt gtgcagctgc actgagggct       780
acaggctggc tgagaaccag aagagctgtg agcctgctgt gccattccca tgtggcagag       840
tgtctgtgag ccagaccagc aagctgacca gggctgaggc tgtgttccct gatgtggact       900
atgtgaacag cactgaggct gaaaccatcc tggacaacat cacccagagc acccagagct       960
tcaatgactt caccagggtg gtgggggggg aggatgccaa gcctggccag ttcccctggc      1020
aagtggtgct gaatggcaag gtggatgcct ctgtgggg cagcattgtg aatgagaagt       1080
ggattgtgac tgctgcccac tgtgtggaga ctggggtgaa gatcactgtg gtggctgggg      1140
agcacaacat tgaggagact gagcacactg agcagaagag gaatgtgatc aggatcatcc      1200
cccaccacaa ctacaatgct gccatcaaca gtacaacca tgacattgcc ctgctggagc      1260
tggatgagcc cctggtgctg aacagctatg tgacccccat ctgcattgct gacaaggagt      1320
acaccaacat cttcctgaag tttggctctg gctatgtgtc tggctgggc agggtgttcc      1380
acaagggcag gtctgccctg gtgctgcagt acctgagggt gccccctggtg acagggcca       1440
cctgcctgct cagcaccaag ttcaccatct acaacaat gttctgtgct ggcttccatg       1500
aggggggcag ggacagctgc caggggact ctggggcccc ccatgtgact gaggtggagg      1560
gcaccagctt cctgactggc atcatcagct gggggagga gtgtgccatg aagggcaagt      1620
atggcatcta caccaaagtc tccagatatg tgaactggat caaggagaag accaagctga      1680
cctga                                                                  1685
```

<210> SEQ ID NO 6
<211> LENGTH: 334
<212> TYPE: DNA
<213> ORGANISM: Artificial Sequence
<220> FEATURE:
<223> OTHER INFORMATION: Synthetic regulatory element

<400> SEQUENCE: 6

```
ccctaaaatg ggcaaacatt gcaagcagca aacagcaaac acacagccct ccctgcctgc        60
tgaccttgga gctggggcag aggtcagaca cctctctggg cccatgccac ctccaactgg       120
acacaggacg ctgtggtttc tgagccaggg ggcgactcag atcccagcca gtggacttag       180
cccctgtttg ctcctccgat aactgggtg accttggtta atattcacca gcagcctccc        240
ccgttgcccc tctggatcca ctgcttaaat acggacgagg acagggccct gtctcctcag       300
```
cttcaggcac caccactgac ctgggacagt gaat        334

<210> SEQ ID NO 7
<211> LENGTH: 447
<212> TYPE: DNA
<213> ORGANISM: Artificial Sequence
<220> FEATURE:
<223> OTHER INFORMATION: Synthetic regulatory element

<400> SEQUENCE: 7
ccctaaaatg ggcaaacatt gcaagcagca acagcaaac acacagccct ccctgcctgc        60
tgaccttgga gctggggcag aggtcagaga cctctctggg cccatgccac ctccaacatc      120
cactcgaccc cttggaattt cggtggagag gagcagaggt tgtcctggcg tggtttaggt      180
agtgtgagag gggaatgact cctttcggta agtgcagtgg aagctgtaca ctgcccaggc      240
aaagcgtccg ggcagcgtag gcgggcgact cagatcccag ccagtggact tagcccctgt      300
ttgctcctcc gataactggg gtgaccttgg ttaatattca ccagcagcct ccccgttgc       360
ccctctggat ccactgctta aatacggacg aggacagggc cctgtctcct cagcttcagg      420
caccaccact gacctgggac agtgaat                                           447

<210> SEQ ID NO 8
<211> LENGTH: 415
<212> TYPE: PRT
<213> ORGANISM: Homo sapiens

<400> SEQUENCE: 8

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu

```
                225                 230                 235                 240

Thr Glu His Thr Glu Gln Lys Arg Asn Val Ile Arg Ile Ile Pro His
                        245                 250                 255

His Asn Tyr Asn Ala Ala Ile Asn Lys Tyr Asn His Asp Ile Ala Leu
                        260                 265                 270

Leu Glu Leu Asp Glu Pro Leu Val Leu Asn Ser Tyr Val Thr Pro Ile
                        275                 280                 285

Cys Ile Ala Asp Lys Glu Tyr Thr Asn Ile Phe Leu Lys Phe Gly Ser
                        290                 295                 300

Gly Tyr Val Ser Gly Trp Gly Arg Val Phe His Lys Gly Arg Ser Ala
        305                 310                 315                 320

Leu Val Leu Gln Tyr Leu Arg Val Pro Leu Val Asp Arg Ala Thr Cys
                        325                 330                 335

Leu Leu Ser Thr Lys Phe Thr Ile Tyr Asn Asn Met Phe Cys Ala Gly
                        340                 345                 350

Phe His Glu Gly Gly Arg Asp Ser Cys Gln Gly Asp Ser Gly Gly Pro
                        355                 360                 365

His Val Thr Glu Val Glu Gly Thr Ser Phe Leu Thr Gly Ile Ile Ser
                        370                 375                 380

Trp Gly Glu Glu Cys Ala Met Lys Gly Lys Tyr Gly Ile Tyr Thr Lys
        385                 390                 395                 400

Val Ser Arg Tyr Val Asn Trp Ile Lys Glu Lys Thr Lys Leu Thr
                        405                 410                 415

<210> SEQ ID NO 9
<211> LENGTH: 1386
<212> TYPE: DNA
<213> ORGANISM: Homo sapiens

<400> SEQUENCE: 9
atgcagcgcg tgaacatgat catggcagaa tcaccaggcc tcatcaccat ctgccttta       60 ggatatctac tcagtgctga atgtacagtt tttcttgatc atgaaaacgc caacaaaatt     120
ctgaatcggc aaagaggta taattcaggt aaattggaag agtttgttca agggaacctt     180
gagagagaat gtatggaaga aaagtgtagt tttgaagaag cacgagaagt ttttgaaaac     240
actgaaagaa caactgaatt ttggaagcag tatgttgatg agatcagtg tgagtccaat     300 ccatgtttaa atggcggcag ttgcaaggat gacattaatt cctatgaatg ttggtgtccc     360
tttggatttg aaggaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgagg ctgttttttcc tgatgtggac     600 tatgtaaatt ctactgaagc tgaaaccatt ttggataaca tcactcaaag cacccaatca     660
tttaatgact tcactcgggt tgttggtgga agatgccaa aaccaggtca attcccttgg     720
caggttgttt tgaatggtaa agttgatgca ttctgtggag gctctatcgt taatgaaaaa     780
tggattgtaa ctgctgccca ctgtgttgaa actggtgtta aaattacagt tgtcgcaggt     840
gaacataata ttgaggagac agaacataca gagcaaaagc gaaatgtgat tcgaattatt     900
cctcaccaca actacaatgc agctattaat aagtacaacc atgacattgc ccttctggaa     960
ctggacgaac cctagtgct aaacagctac gttacaccta tttgcattgc tgacaaggaa    1020
tacacgaaca tcttcctcaa atttggatct ggctatgtaa gtggctgggg aagagtcttc    1080
```

```
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaa                                                               1386
```

<210> SEQ ID NO 10
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

```
Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
                530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
```

<210> SEQ ID NO 11
<211> LENGTH: 1386
<212> TYPE: DNA
<213> ORGANISM: Artificial Sequence
<220> FEATURE:
<223> OTHER INFORMATION: Synthetic construct

<400> SEQUENCE: 11

```
atgcagaggg tgaacatgat catggctgag agccctggcc tgatcaccat ctgcctgctg      60
ggctacctgc tgtctgctga gtgcactgtg ttcctggacc atgagaatgc caacaagatc     120
ctgaacaggc ccaagagata caactctggc aagctggagg agtttgtgca gggcaacctg     180
gagagggagt gcatggagga gaagtgcagc tttgaggagg ccagggaggt gtttgagaac     240
actgagagga ccactgagtt ctggaagcag tatgtggatg gggaccagtg tgagagcaac     300
ccctgcctga tgggggcag ctgcaaggat gacatcaaca gctatgagtg ctggtgcccc     360
tttggctttg agggcaagaa ctgtgagctg gatgtgacct gcaacatcaa gaatggcaga     420
tgtgagcagt tctgcaagaa ctctgctgac aacaaggtgg tgtgcagctg cactgagggc     480
tacaggctgg ctgagaacca aagagctgt gagcctgctg tgccattccc atgtggcaga     540
gtgtctgtga ccagaccag caagctgacc agggctgagg ctgtgttccc tgatgtggac     600
tatgtgaaca gcactgaggc tgaaaccatc ctggacaaca tcacccagag cacccagagc     660
ttcaatgact tcaccagggt ggtggggggg gaggatgcca agcctggcca gttcccctgg     720
caagtggtgc tgaatggcaa ggtggatgcc ttctgtgggg gcagcattgt gaatgagaag     780
tggattgtga ctgctgccca ctgtgtggag actggggtga agatcactgt ggtggctggg     840
gagcacaaca ttgaggagac tgagcacact gagcagaaga ggaatgtgat caggatcatc     900
ccccaccaca actacaatgc tgccatcaac aagtacaacc atgacattgc cctgctggag     960
ctggatgagc cctggtgct gaacagctat gtgaccccca tctgcattgc tgacaaggag    1020
tacaccaaca tcttcctgaa gtttggctct ggctatgtgt ctggctgggg cagggtgttc    1080
cacaagggca ggtctgccct ggtgctgcag tacctgaggg tgcccctggt ggacagggcc    1140
acctgcctgt tgagcaccaa gttcaccatc tacaacaaca tgttctgtgc tggcttccat    1200
gagggggggca gggacagctg ccaggggggac tctgggggcc cccatgtgac tgaggtggag    1260
ggcaccagct tcctgactgg catcatcagc tggggggagg agtgtgccat gaagggcaag    1320
tatggcatct acaccaaagt ctccagatat gtgaactgga tcaaggagaa gaccaagctg    1380
acctga                                                                1386
```

<210> SEQ ID NO 12
<211> LENGTH: 1386
<212> TYPE: DNA
<213> ORGANISM: Artificial Sequence
<220> FEATURE:
<223> OTHER INFORMATION: Synthetic construct

<400> SEQUENCE: 12

```
atgcagaggg tgaacatgat catggctgag agccctggcc tgatcaccat ctgcctgctg      60
ggctacctgc tgtctgctga gtgcactgtg ttcctggacc atgagaatgc caacaagatc     120
ctgaacaggc ccaagagata caactctggc aagctggagg agtttgtgca gggcaacctg     180
gagagggagt gcatggagga gaagtgcagc tttgaggagg ccagggaggt gtttgagaac     240
actgagagga ccactgagtt ctggaagcag tatgtggatg gggaccagtg tgagagcaac     300
```

```
cectgcctga atgggggcag ctgcaaggat gacatcaaca gctatgagtg ctggtgcccc    360
tttggctttg agggcaagaa ctgtgagctg gatgtgacct gcaacatcaa gaatggcaga    420
tgtgagcagt tctgcaagaa ctctgctgac aacaaggtgg tgtgcagctg cactgagggc    480
tacaggctgg ctgagaacca gaagagctgt gagcctgctg tgccattccc atgtggcaga    540
gtgtctgtga gccagaccag caagctgacc agggctgagg ctgtgttccc tgatgtggac    600
tatgtgaaca gcactgaggc tgaaaccatc ctggacaaca tcacccagag cacccagagc    660
ttcaatgact tcaccagggt ggtggggggg gaggatgcca agcctggcca gttcccctgg    720
caagtggtgc tgaatggcaa ggtggatgcc ttctgtgggg gcagcattgt gaatgagaag    780
tggattgtga ctgctgccca ctgtgtggag actggggtga agatcactgt ggtggctggg    840
gagcacaaca ttgaggagac tgagcacact gagcagaaga ggaatgtgat caggatcatc    900
ccccaccaca actacaatgc tgccatcaac aagtacaacc atgacattgc cctgctggag    960
ctggatgagc ccctggtgct gaacagctat gtgacccccca tctgcattgc tgacaaggag   1020
tacaccaaca tcttcctgaa gtttggctct ggctatgtgt ctggctgggg cagggtgttc   1080
cacaagggca ggtctgccct ggtgctgcag tacctgaggg tgcccctggt ggacagggcc   1140
acctgcctga ggagcaccaa gttcaccatc tacaacaaca tgttctgtgc tggcttccat   1200 gagggggggca gggacagctg ccaggggggac tctggggggcc ccatgtgac tgaggtggag   1260 ggcaccagct tcctgactgg catcatcagc tggggggagg agtgtgccat gaagggcaag   1320
tatggcatct acaccaaagt ctccagatat gtgaactgga tcaaggagaa gaccaagctg   1380
acctga                                                              1386

<210> SEQ ID NO 13
<211> LENGTH: 117
<212> TYPE: DNA
<213> ORGANISM: Artificial Sequence
<220> FEATURE:
<223> OTHER INFORMATION: Synthetic enhancer element

<400> SEQUENCE: 13
ccctaaaatg gcaaacatt gcaagcagca aacagcaaac acacagccct ccctgcctgc     60
tgaccttgga gctggggcag aggtcagaca cctctctggg cccatgccac ctccaac     117

<210> SEQ ID NO 14
<211> LENGTH: 185
<212> TYPE: DNA
<213> ORGANISM: Artificial Sequence
<220> FEATURE:
<223> OTHER INFORMATION: Synthetic promoter element

<400> SEQUENCE: 14
gggcgactca gatcccagcc agtggactta gcccctgttt gctcctccga taactggggt    60
gaccttggtt aatattcacc agcagcctcc ccgttgccc ctctggatcc actgcttaaa    120
tacggacgag gacagggccc tgtctcctca gcttcaggca ccaccactga cctgggacag    180
tgaat                                                               185

<210> SEQ ID NO 15
<211> LENGTH: 195
<212> TYPE: DNA
<213> ORGANISM: Artificial Sequence
<220> FEATURE:
<223> OTHER INFORMATION: Synthetic construct
```

<400> SEQUENCE: 15

```
atgcagcgcg tgaacatgat catggcagaa tcaccaggcc tcatcaccat ctgccttta      60 ggatatctac tcagtgctga atgtacagtt tttcttgatc atgaaaacgc caacaaaatt    120
ctgaatcggc caaagaggta taattcaggt aaattggaag agtttgttca agggaacctt    180
gagagagaat gtatg                                                     195
```

<210> SEQ ID NO 16
<211> LENGTH: 461
<212> TYPE: PRT
<213> ORGANISM: Homo sapiens

<400> SEQUENCE: 16

```
Met Gln Arg Val Asn Met Ile Met Ala Glu Ser Pro Gly Leu Ile Thr
  1               5                  10                  15

Ile Cys Leu Leu Gly Tyr Leu Leu Ser Ala Glu Cys Thr Val Phe Leu
             20                  25                  30

Asp His Glu Asn Ala Asn Lys Ile Leu Asn Arg Pro Lys Arg Tyr Asn
         35                  40                  45

Ser Gly Lys Leu Glu Glu Phe Val Gln Gly Asn Leu Glu Arg Glu Cys
     50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
```

```
                    325                 330                 335
Ala Asp Lys Glu Tyr Thr Asn Ile Phe Leu Lys Phe Gly Ser Gly Tyr
                340                 345                 350
Val Ser Gly Trp Gly Arg Val Phe His Lys Gly Arg Ser Ala Leu Val
                355                 360                 365
Leu Gln Tyr Leu Arg Val Pro Leu Val Asp Arg Ala Thr Cys Leu Leu
                370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
                420                 425                 430
Glu Glu Cys Ala Met Lys Gly Lys Tyr Gly Ile Tyr Thr Lys Val Ser
                435                 440                 445
Arg Tyr Val Asn Trp Ile Lys Glu Lys Thr Lys Leu Thr
                450                 455                 460

<210> SEQ ID NO 17
<211> LENGTH: 724
<212> TYPE: PRT
<213> ORGANISM: adeno-associated virus 5

<400> SEQUENCE: 17

Met Ser Phe Val Asp His Pro Pro Asp Trp Leu Glu Val Gly Glu
1               5                   10                  15
Gly Leu Arg Glu Phe Leu Gly Leu Glu Ala Gly Pro Pro Lys Pro Lys
                20                  25                  30
Pro Asn Gln Gln His Gln Asp Gln Ala Arg Gly Leu Val Leu Pro Gly
                35                  40                  45
Tyr Asn Tyr Leu Gly Pro Gly Asn Gly Leu Asp Arg Gly Glu Pro Val
            50                  55                  60
Asn Arg Ala Asp Glu Val Ala Arg Glu His Asp Ile Ser Tyr Asn Glu
65              70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
                100                 105                 110
Leu Gly Lys Ala Val Phe Gln Ala Lys Lys Arg Val Leu Glu Pro Phe
                115                 120                 125
Gly Leu Val Glu Glu Gly Ala Lys Thr Ala Pro Thr Gly Lys Arg Ile
                130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
                180                 185                 190
Met Ser Ala Gly Gly Gly Gly Pro Leu Gly Asp Asn Asn Gln Gly Ala
                195                 200                 205
Asp Gly Val Gly Asn Ala Ser Gly Asp Trp His Cys Asp Ser Thr Trp
                210                 215                 220
Met Gly Asp Arg Val Val Thr Lys Ser Thr Arg Thr Trp Val Leu Pro
225                 230                 235                 240
```

-continued

```
Ser Tyr Asn Asn His Gln Tyr Arg Glu Ile Lys Ser Gly Ser Val Asp
            245                 250                 255

Gly Ser Asn Ala Asn Ala Tyr Phe Gly Tyr Ser Thr Pro Trp Gly Tyr
        260                 265                 270

Phe Asp Phe Asn Arg Phe His Ser His Trp Ser Pro Arg Asp Trp Gln
    275                 280                 285

Arg Leu Ile Asn Asn Tyr Trp Gly Phe Arg Pro Arg Ser Leu Arg Val
290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
```

```
            660                 665                 670
Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 18
<211> LENGTH: 1685
<212> TYPE: DNA
<213> ORGANISM: Artificial Sequence
<220> FEATURE:
<223> OTHER INFORMATION: Synthetic construct

<400> SEQUENCE: 18
atgcagcgcg tgaacatgat catggcagaa tcaccaggcc tcatcaccat ctgcctttta      60
ggatatctac tcagtgctga atgtacaggt ttgtttcctt ttttaaaata cattgagtat     120
gcttgccttt tagatataga aatatctgat gctgtcttct tcactaaatt ttgattacat     180
gatttgacag caatattgaa gagtctaaca gccagcacgc aggttggtaa gtactgtggg     240
aacatcacag attttggctc catgccctaa agagaaattg gctttcagat tatttggatt     300
aaaaacaaag acttcttaa gagatgtaaa attttcatga tgttttcttt tttgctaaaa      360
ctaaagaatt attcttttac atttcagttt ttcttgatca tgaaaacgcc aacaaaattc     420
tgaatcggcc aaagaggtat aattcaggta aattggaaga gtttgttcaa gggaaccttg     480
agagagaatg tatggaggag aagtgttctt cgaggaggc gagagaggtt tcgagaata      540 ctgagcgaac aaccgaattc tggaaacaat atgtggatgg cgaccaatgt gaatctaatc     600
cctgcctcaa cggtggctca tgcaaagacg atatcaacag ctacgagtgt ggtgcccct     660 ttggtttcga gggaaagaat tgcgagcttg atgtaacctg taacattaag aatgggcgct     720
gcgaacagtt ttgcaagaac agcgccgaca taaggtcgt ctgcagttgt accgaaggct     780
ataggcttgc agagaatcag aagagttgcg agcctgctgt gccgttccca tgtggcagag     840
tcagtgtgtc ccaaactagc aagctgacaa gagcagaagc cgttttcccc gatgtggact     900
acgtgaattc cactgaagcc gaaacgatcc tggacaatat cacacagagc actcagtctt     960
tcaacgactt cacacgggtt gtgggaggag aggacgccaa acccggccag tttccttggc    1020
aagtcgttct taacggcaag gtcgacgcct tttgtggagg gagtattgtg aacgagaaat    1080
ggattgtcac cgctgctcat tgtgttgaaa ctgggggtgaa aatcactgtt gtcgcaggag    1140
agcacaatat cgaagagaca gaacacaccg agcagaaacg caacgttatt cggatcattc    1200
cacatcacaa ctacaatgct gccatcaaca agtacaacca cgacattgcg ctgctggagt    1260
tggatgaacc tctcgtgctc aactcctatg tgaccccaat ctgcatagca gataaggagt    1320
ataccaacat cttcctgaag tttgggtcag ttatgtgtc aggctgggga cgagtgtttc    1380
ataaagggag atcagcactg gtgttgcagt atctgcgcgt accactggtg atcgggcta    1440 cttgcctgct aagcacaaaa ttcaccatct acaacaacat gttttgtgcc ggttttcacg    1500
aaggcggcag ggacagctgt caggaagatt ccggagggcc tcatgtcaca gaggtcgagg    1560
gcacctcctt tctcactggg attataagct ggggagaaga atgcgccatg aaagggaagt    1620
acggcatata cacgaaagtg tctagatacg tgaattggat taaggaaaag accaaactga    1680
```

-continued cgtga 1685

<210> SEQ ID NO 19
<211> LENGTH: 1248
<212> TYPE: DNA
<213> ORGANISM: Homo sapiens

<400> SEQUENCE: 19

```
tataattcag gtaaattgga agagtttgtt caagggaacc ttgagagaga atgtatggaa    60
gaaaagtgta gttttgaaga agcacgagaa gttttgaaa acactgaaag aacaactgaa   120
ttttggaagc agtatgttga tggagatcag tgtgagtcca atccatgttt aaatggcggc   180
agttgcaagg atgacattaa ttcctatgaa tgttggtgtc cctttggatt tgaaggaaag   240
aactgtgaat tagatgtaac atgtaacatt aagaatggca gatgcgagca gttttgtaaa   300
aatagtgctg ataacaaggt ggtttgctcc tgtactgagg gatatcgact tgcagaaaac   360
cagaagtcct gtgaaccagc agtgccattt ccatgtggaa gagtttctgt ttcacaaact   420
tctaagctca cccgtgctga ggctgttttt cctgatgtgg actatgtaaa ttctactgaa   480
gctgaaacca ttttggataa catcactcaa agcacccaat catttaatga cttcactcgg   540
gttgttggtg gagaagatgc caaaccaggt caattccctt ggcaggttgt tttgaatggt   600
aaagttgatg cattctgtgg aggctctatc gttaatgaaa aatggattgt aactgctgcc   660
cactgtgttg aaactggtgt taaaattaca gttgtcgcag gtgaacataa tattgaggag   720
acagaacata cagagcaaaa gcgaaatgtg attcgaatta ttcctcacca caactacaat   780
gcagctatta taagtacaa ccatgacatt gcccttctgg aactggacga acccttagtg   840
ctaaacagct acgttacacc tatttgcatt gctgacaagg aatacacgaa catcttcctc   900
aaatttggat ctggctatgt aagtggctgg ggaagagtct tccacaaagg agatcagct   960
ttagttcttc agtaccttag agttccactt gttgaccgag ccacatgtct tcgatctaca  1020
aagttcacca tctataacaa catgttctgt gctggcttcc atgaaggagg tagagattca  1080
tgtcaaggag atagtggggg accccatgtt actgaagtgg aagggaccag tttcttaact  1140
ggaattatta gctggggtga agagtgtgca atgaaaggca aatatggaat atataccaag  1200
gtatcccggt atgtcaactg gattaaggaa aaaacaaagc tcacttaa             1248
```

<210> SEQ ID NO 20
<211> LENGTH: 724
<212> TYPE: PRT
<213> ORGANISM: Artificial Sequence
<220> FEATURE:
<223> OTHER INFORMATION: Synthetic polypeptide

<400> SEQUENCE: 20

```
Met Ala Ala Asp Gly Tyr Leu Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95
```

```
Ala Glu Phe Gln Glu Lys Leu Ala Asp Asp Thr Ser Phe Gly Gly Asn
                100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
        130                 135                 140

Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510
```

```
Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 21
<211> LENGTH: 725
<212> TYPE: PRT
<213> ORGANISM: Artificial Sequence
<220> FEATURE:
<223> OTHER INFORMATION: Synthetic polypeptide

<400> SEQUENCE: 21

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Asn Tyr Leu Gly Pro Gly Asn Gly Leu Asp Arg Gly Glu Pro
    50                  55                  60

Val Asn Arg Ala Asp Glu Val Ala Arg Glu His Asp Ile Ser Tyr Asn
65                  70                  75                  80

Glu Gln Leu Glu Ala Gly Asp Asn Pro Tyr Leu Lys Tyr Asn His Ala
            85                  90                  95

Asp Ala Glu Phe Gln Glu Lys Leu Ala Asp Asp Thr Ser Phe Gly Gly
        100                 105                 110

Asn Leu Gly Lys Ala Val Phe Gln Ala Lys Lys Arg Val Leu Glu Pro
    115                 120                 125

Phe Gly Leu Val Glu Glu Gly Ala Lys Thr Ala Pro Thr Gly Lys Arg
130                 135                 140

Ile Asp Asp His Phe Pro Lys Arg Lys Lys Ala Arg Thr Glu Glu Asp
```

-continued

```
            145                 150                 155                 160
        Ser Lys Pro Ser Thr Ser Ser Asp Ala Glu Ala Gly Pro Ser Gly Ser
                            165                 170                 175
        Gln Gln Leu Gln Ile Pro Ala Gln Pro Ala Ser Ser Leu Gly Ala Asp
                            180                 185                 190
        Thr Met Ser Ala Gly Gly Gly Pro Leu Gly Asp Asn Asn Gln Gly
                    195                 200                 205
        Ala Asp Gly Val Gly Asn Ala Ser Gly Asp Trp His Cys Asp Ser Thr
                210                 215                 220
        Trp Met Gly Asp Arg Val Val Thr Lys Ser Thr Arg Thr Trp Val Leu
        225                 230                 235                 240
        Pro Ser Tyr Asn Asn His Gln Tyr Arg Glu Ile Lys Ser Gly Ser Val
                            245                 250                 255
        Asp Gly Ser Asn Ala Asn Ala Tyr Phe Gly Tyr Ser Thr Pro Trp Gly
                    260                 265                 270
        Tyr Phe Asp Phe Asn Arg Phe His Ser His Trp Ser Pro Arg Asp Trp
                    275                 280                 285
        Gln Arg Leu Ile Asn Asn Tyr Trp Gly Phe Arg Pro Arg Ser Leu Arg
                    290                 295                 300
        Val Lys Ile Phe Asn Ile Gln Val Lys Glu Val Thr Val Gln Asp Ser
        305                 310                 315                 320
        Thr Thr Thr Ile Ala Asn Asn Leu Thr Ser Thr Val Gln Val Phe Thr
                            325                 330                 335
        Asp Asp Asp Tyr Gln Leu Pro Tyr Val Val Gly Asn Gly Thr Glu Gly
                    340                 345                 350
        Cys Leu Pro Ala Phe Pro Pro Gln Val Phe Thr Leu Pro Gln Tyr Gly
                    355                 360                 365
        Tyr Ala Thr Leu Asn Arg Asp Asn Thr Glu Asn Pro Thr Glu Arg Ser
                370                 375                 380
        Ser Phe Phe Cys Leu Glu Tyr Phe Pro Ser Lys Met Leu Arg Thr Gly
        385                 390                 395                 400
        Asn Asn Phe Glu Phe Thr Tyr Asn Phe Glu Glu Val Pro Phe His Ser
                            405                 410                 415
        Ser Phe Ala Pro Ser Gln Asn Leu Phe Lys Leu Ala Asn Pro Leu Val
                    420                 425                 430
        Asp Gln Tyr Leu Tyr Arg Phe Val Ser Thr Asn Asn Thr Gly Gly Val
                    435                 440                 445
        Gln Phe Asn Lys Asn Leu Ala Gly Arg Tyr Ala Asn Thr Tyr Lys Asn
                    450                 455                 460
        Trp Phe Pro Gly Pro Met Gly Arg Thr Gln Gly Trp Asn Leu Gly Ser
        465                 470                 475                 480
        Gly Val Asn Arg Ala Ser Val Ser Ala Phe Ala Thr Thr Asn Arg Met
                            485                 490                 495
        Glu Leu Glu Gly Ala Ser Tyr Gln Val Pro Pro Gln Pro Asn Gly Met
                    500                 505                 510
        Thr Asn Asn Leu Gln Gly Ser Asn Thr Tyr Ala Leu Glu Asn Thr Met
                    515                 520                 525
        Ile Phe Asn Ser Gln Pro Ala Asn Pro Gly Thr Thr Ala Thr Tyr Leu
                    530                 535                 540
        Glu Gly Asn Met Leu Ile Thr Ser Glu Ser Glu Thr Gln Pro Val Asn
        545                 550                 555                 560
        Arg Val Ala Tyr Asn Val Gly Gly Gln Met Ala Thr Asn Asn Gln Ser
                            565                 570                 575
```

```
Ser Thr Thr Ala Pro Ala Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
        675                 680                 685

Gln Tyr Thr Asn Asn Tyr Asn Asp Pro Gln Phe Val Asp Phe Ala Pro
690                 695                 700

Asp Ser Thr Gly Glu Tyr Arg Thr Thr Arg Pro Ile Gly Thr Arg Tyr
705                 710                 715                 720

Leu Thr Arg Pro Leu
                725

<210> SEQ ID NO 22
<211> LENGTH: 725
<212> TYPE: PRT
<213> ORGANISM: Artificial Sequence
<220> FEATURE:
<223> OTHER INFORMATION: Synthetic polypeptide

<400> SEQUENCE: 22

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Arg Ala Asp Glu Val Ala Arg Glu His Asp Ile Ser Tyr Asn
65                  70                  75                  80

Glu Gln Leu Glu Ala Gly Asp Asn Pro Tyr Leu Lys Tyr Asn His Ala
                85                  90                  95

Asp Ala Glu Phe Gln Glu Lys Leu Ala Asp Asp Thr Ser Phe Gly Gly
            100                 105                 110

Asn Leu Gly Lys Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Gly Pro Leu Gly Asp Asn Asn Gln Gly
        195                 200                 205
```

```
Ala Asp Gly Val Gly Asn Ala Ser Gly Asp Trp His Cys Asp Ser Thr
    210                 215                 220
Trp Met Gly Asp Arg Val Val Thr Lys Ser Thr Arg Thr Trp Val Leu
225                 230                 235                 240
Pro Ser Tyr Asn Asn His Gln Tyr Arg Glu Ile Lys Ser Gly Ser Val
                245                 250                 255
Asp Gly Ser Asn Ala Asn Ala Tyr Phe Gly Tyr Ser Thr Pro Trp Gly
                260                 265                 270
Tyr Phe Asp Phe Asn Arg Phe His Ser His Trp Ser Pro Arg Asp Trp
            275                 280                 285
Gln Arg Leu Ile Asn Asn Tyr Trp Gly Phe Arg Pro Arg Ser Leu Arg
        290                 295                 300
Val Lys Ile Phe Asn Ile Gln Val Lys Glu Val Thr Val Gln Asp Ser
305                 310                 315                 320
Thr Thr Thr Ile Ala Asn Asn Leu Thr Ser Thr Val Gln Val Phe Thr
                325                 330                 335
Asp Asp Asp Tyr Gln Leu Pro Tyr Val Val Gly Asn Gly Thr Glu Gly
            340                 345                 350
Cys Leu Pro Ala Phe Pro Pro Gln Val Phe Thr Leu Pro Gln Tyr Gly
        355                 360                 365
Tyr Ala Thr Leu Asn Arg Asp Asn Thr Glu Asn Pro Thr Glu Arg Ser
    370                 375                 380
Ser Phe Phe Cys Leu Glu Tyr Phe Pro Ser Lys Met Leu Arg Thr Gly
385                 390                 395                 400
Asn Asn Phe Glu Phe Thr Tyr Asn Phe Glu Glu Val Pro Phe His Ser
                405                 410                 415
Ser Phe Ala Pro Ser Gln Asn Leu Phe Lys Leu Ala Asn Pro Leu Val
            420                 425                 430
Asp Gln Tyr Leu Tyr Arg Phe Val Ser Thr Asn Asn Thr Gly Gly Val
        435                 440                 445
Gln Phe Asn Lys Asn Leu Ala Gly Arg Tyr Ala Asn Thr Tyr Lys Asn
    450                 455                 460
Trp Phe Pro Gly Pro Met Gly Arg Thr Gln Gly Trp Asn Leu Gly Ser
465                 470                 475                 480
Gly Val Asn Arg Ala Ser Val Ser Ala Phe Ala Thr Thr Asn Arg Met
                485                 490                 495
Glu Leu Glu Gly Ala Ser Tyr Gln Val Pro Pro Gln Pro Asn Gly Met
            500                 505                 510
Thr Asn Asn Leu Gln Gly Ser Asn Thr Tyr Ala Leu Glu Asn Thr Met
        515                 520                 525
Ile Phe Asn Ser Gln Pro Ala Asn Pro Gly Thr Thr Ala Thr Tyr Leu
    530                 535                 540
Glu Gly Asn Met Leu Ile Thr Ser Glu Ser Glu Thr Gln Pro Val Asn
545                 550                 555                 560
Arg Val Ala Tyr Asn Val Gly Gly Gln Met Ala Thr Asn Asn Gln Ser
                565                 570                 575
Ser Thr Thr Ala Pro Ala Thr Gly Thr Tyr Asn Leu Gln Glu Ile Val
            580                 585                 590
Pro Gly Ser Val Trp Met Glu Arg Asp Val Tyr Leu Gln Gly Pro Ile
        595                 600                 605
Trp Ala Lys Ile Pro Glu Thr Gly Ala His Phe His Pro Ser Pro Ala
    610                 615                 620
```

```
Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
            645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
        675                 680                 685

Gln Tyr Thr Asn Asn Tyr Asn Asp Pro Gln Phe Val Asp Phe Ala Pro
    690                 695                 700

Asp Ser Thr Gly Glu Tyr Arg Thr Thr Arg Pro Ile Gly Thr Arg Tyr
705                 710                 715                 720

Leu Thr Arg Pro Leu
                725

<210> SEQ ID NO 23
<211> LENGTH: 725
<212> TYPE: PRT
<213> ORGANISM: Artificial Sequence
<220> FEATURE:
<223> OTHER INFORMATION: Synthetic polypeptide

<400> SEQUENCE: 23

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Lys Leu Ala Asp Asp Thr Ser Phe Gly Gly
            100                 105                 110

Asn Leu Gly Lys Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255
```

```
Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Ser
                565                 570                 575

Ser Thr Thr Ala Pro Ala Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
    610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
```

```
                    675                 680                 685
Gln Tyr Thr Asn Asn Tyr Asn Asp Pro Gln Phe Val Asp Phe Ala Pro
    690                 695                 700
Asp Ser Thr Gly Glu Tyr Arg Thr Arg Pro Ile Gly Thr Arg Tyr
705                 710                 715                 720
Leu Thr Arg Pro Leu
                725

<210> SEQ ID NO 24
<211> LENGTH: 725
<212> TYPE: PRT
<213> ORGANISM: Artificial Sequence
<220> FEATURE:
<223> OTHER INFORMATION: Synthetic polypeptide

<400> SEQUENCE: 24

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Phe Gly Leu Val Glu Glu Gly Ala Lys Thr Ala Pro Thr Gly Lys Arg
    130                 135                 140
Ile Asp Asp His Phe Pro Lys Arg Lys Lys Ala Arg Thr Glu Glu Asp
145                 150                 155                 160
Ser Lys Pro Ser Thr Ser Ser Asp Ala Glu Ala Gly Pro Ser Gly Ser
                165                 170                 175
Gln Gln Leu Gln Ile Pro Ala Gln Pro Ala Ser Ser Leu Gly Ala Asp
            180                 185                 190
Thr Met Ser Ala Gly Gly Gly Gly Pro Leu Gly Asp Asn Asn Gln Gly
        195                 200                 205
Ala Asp Gly Val Gly Asn Ala Ser Gly Asp Trp His Cys Asp Ser Thr
    210                 215                 220
Trp Met Gly Asp Arg Val Val Thr Lys Ser Thr Arg Thr Trp Val Leu
225                 230                 235                 240
Pro Ser Tyr Asn Asn His Gln Tyr Arg Glu Ile Lys Ser Gly Ser Val
                245                 250                 255
Asp Gly Ser Asn Ala Asn Ala Tyr Phe Gly Tyr Ser Thr Pro Trp Gly
            260                 265                 270
Tyr Phe Asp Phe Asn Arg Phe His Ser His Trp Ser Pro Arg Asp Trp
        275                 280                 285
Gln Arg Leu Ile Asn Asn Tyr Trp Gly Phe Arg Pro Arg Ser Leu Arg
    290                 295                 300
Val Lys Ile Phe Asn Ile Gln Val Lys Glu Val Thr Val Gln Asp Ser
```

```
        305                 310                 315                 320
    Thr Thr Thr Ile Ala Asn Asn Leu Thr Ser Thr Val Gln Val Phe Thr
                    325                 330                 335
    Asp Asp Asp Tyr Gln Leu Pro Tyr Val Val Gly Asn Gly Thr Glu Gly
                    340                 345                 350
    Cys Leu Pro Ala Phe Pro Pro Gln Val Phe Thr Leu Pro Gln Tyr Gly
                    355                 360                 365
    Tyr Ala Thr Leu Asn Arg Asp Asn Thr Glu Asn Pro Thr Glu Arg Ser
                    370                 375                 380
    Ser Phe Phe Cys Leu Glu Tyr Phe Pro Ser Lys Met Leu Arg Thr Gly
    385                 390                 395                 400
    Asn Asn Phe Glu Phe Thr Tyr Asn Phe Glu Glu Val Pro Phe His Ser
                    405                 410                 415
    Ser Phe Ala Pro Ser Gln Asn Leu Phe Lys Leu Ala Asn Pro Leu Val
                    420                 425                 430
    Asp Gln Tyr Leu Tyr Arg Phe Val Ser Thr Asn Asn Thr Gly Gly Val
                    435                 440                 445
    Gln Phe Asn Lys Asn Leu Ala Gly Arg Tyr Ala Asn Thr Tyr Lys Asn
                    450                 455                 460
    Trp Phe Pro Gly Pro Met Gly Arg Thr Gln Gly Trp Asn Leu Gly Ser
    465                 470                 475                 480
    Gly Val Asn Arg Ala Ser Val Ser Ala Phe Ala Thr Thr Asn Arg Met
                    485                 490                 495
    Glu Leu Glu Gly Ala Ser Tyr Gln Val Pro Pro Gln Pro Asn Gly Met
                    500                 505                 510
    Thr Asn Asn Leu Gln Gly Ser Asn Thr Tyr Ala Leu Glu Asn Thr Met
                    515                 520                 525
    Ile Phe Asn Ser Gln Pro Ala Asn Pro Gly Thr Thr Ala Thr Tyr Leu
                    530                 535                 540
    Glu Gly Asn Met Leu Ile Thr Ser Glu Ser Glu Thr Gln Pro Val Asn
    545                 550                 555                 560
    Arg Val Ala Tyr Asn Val Gly Gly Gln Met Ala Thr Asn Asn Gln Ser
                    565                 570                 575
    Ser Thr Thr Ala Pro Ala Thr Gly Thr Tyr Asn Leu Gln Glu Ile Val
                    580                 585                 590
    Pro Gly Ser Val Trp Met Glu Arg Asp Val Tyr Leu Gln Gly Pro Ile
                    595                 600                 605
    Trp Ala Lys Ile Pro Glu Thr Gly Ala His Phe His Pro Ser Pro Ala
    610                 615                 620
    Met Gly Gly Phe Gly Leu Lys His Pro Pro Pro Met Met Leu Ile Lys
    625                 630                 635                 640
    Asn Thr Pro Val Pro Gly Asn Ile Thr Ser Phe Ser Asp Val Pro Val
                    645                 650                 655
    Ser Ser Phe Ile Thr Gln Tyr Ser Thr Gly Gln Val Thr Val Glu Met
                    660                 665                 670
    Glu Trp Glu Leu Lys Lys Glu Asn Ser Lys Arg Trp Asn Pro Glu Ile
                    675                 680                 685
    Gln Tyr Thr Asn Asn Tyr Asn Asp Pro Gln Phe Val Asp Phe Ala Pro
                    690                 695                 700
    Asp Ser Thr Gly Glu Tyr Arg Thr Thr Arg Pro Ile Gly Thr Arg Tyr
    705                 710                 715                 720
    Leu Thr Arg Pro Leu
                    725
```

```
<210> SEQ ID NO 25
<211> LENGTH: 725
<212> TYPE: PRT
<213> ORGANISM: Artificial Sequence
<220> FEATURE:
<223> OTHER INFORMATION: Synthetic polypeptide

<400> SEQUENCE: 25
```

| Met | Ala | Ala | Asp | Gly | Tyr | Leu | Pro | Asp | Trp | Leu | Glu | Asp | Thr | Leu | Ser |
|---|---|---|---|---|---|---|---|---|---|---|---|---|---|---|---|
| 1 | | | | 5 | | | | | 10 | | | | | 15 | |

| Glu | Gly | Ile | Arg | Gln | Trp | Trp | Lys | Leu | Lys | Pro | Gly | Pro | Pro | Pro |
|---|---|---|---|---|---|---|---|---|---|---|---|---|---|---|
| | | | 20 | | | | | 25 | | | | | 30 | |

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Thr Gly Lys Arg
    130                 135                 140

Ile Asp Asp His Phe Pro Lys Arg Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Ser
                565                 570                 575

Ser Thr Thr Ala Pro Ala Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
    610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
        675                 680                 685

Gln Tyr Thr Asn Asn Tyr Asn Asp Pro Gln Phe Val Asp Phe Ala Pro
    690                 695                 700

Asp Ser Thr Gly Glu Tyr Arg Thr Thr Arg Pro Ile Gly Thr Arg Tyr
705                 710                 715                 720

Leu Thr Arg Pro Leu
            725

<210> SEQ ID NO 26
<211> LENGTH: 1386
<212> TYPE: DNA
<213> ORGANISM: Artificial Sequence
<220> FEATURE:
<223> OTHER INFORMATION: Synthetic construct

```
<400> SEQUENCE: 26
atgcagaggg tgaacatgat catggctgag agccctggcc tgatcaccat ctgcctgctg      60
ggctacctgc tgtctgctga gtgcactgtg ttcctggacc atgagaatgc caacaagatc     120
ctgaacaggc caagagata caactctggc aagctggagg agtttgtgca gggcaacctg      180
gagagggagt gcatggagga gaagtgcagc tttgaggagg ccagggaggt gtttgagaac     240
actgagagga ccactgagtt ctggaagcag tatgtggatg gggaccagtg tgagagcaac     300
ccctgcctga atgggggcag ctgcaaggat gacatcaaca gctatgagtg ctggtgcccc     360
tttggctttg agggcaagaa ctgtgagctg gatgtgacct gcaacatcaa gaatggcaga     420
tgtgagcagt tctgcaagaa ctctgctgac aacaaggtgg tgtgcagctg cactgagggc     480
tacaggctgg ctgagaacca gaagagctgt gagcctgctg tgccattccc atgtggcaga     540
gtgtctgtga gccagaccag caagctgacc agggctgagg ctgtgttccc tgatgtggac     600
tatgtgaaca gcactgaggc tgaaaccatc ctggacaaca tcacccagag cacccagagc     660
ttcaatgact tcaccagggt ggtgggggg gaggatgcca agcctggcca gttcccctgg      720
caagtggtgc tgaatggcaa ggtggatgcc ttctgtgggg gcagcattgt gaatgagaag     780
tggattgtga ctgctgccca ctgtgtggag actggggtga agatcactgt ggtggctggg     840
gagcacaaca ttgaggagac tgagcacact gagcagaaga ggaatgtgat caggatcatc     900
ccccaccaca actacaatgc tgccatcaac aagtacaacc atgacattgc cctgctggag     960
ctggatgagc ccctggtgct gaacagctat gtgacccca tctgcattgc tgacaaggag     1020
tacaccaaca tcttcctgaa gtttggctct ggctatgtgt ctggctgggg cagggtgttc    1080
cacaagggca ggtctgccct ggtgctgcag tacctgaggg tgcccctggt ggacagggcc    1140
acctgcctgc tgagcaccaa gttcaccatc tacaacaaca tgttctgtgc tggcttccat    1200 gagggggca gggacagctg ccagggggac tctgggggcc cccatgtgac tgaggtggag     1260
ggcaccagct tcctgactgg catcatcagc tgggggggagg agtgtgccat gaagggcaag    1320
tatggcatct acaccaaagt ctccagatat gtgaactgga tcaaggagaa gaccaagctg    1380
acctga                                                                1386
```

FACTOR IX ENCODING NUCLEOTIDES

FIELD

The present invention relates to polynucleotides comprising a nucleotide sequence encoding Factor IX, viral particles comprising the polynucleotides and treatments utilising the polynucleotides.

SEQUENCE LISTING

The instant application contains a Sequence Listing which has been submitted in ASCII format via EFS-Web and is hereby incorporated by reference in its entirety. Said ASCII copy, created on Aug. 20, 2018, is named 52186-706.201_SL.txt and is 79,915 bytes in size.

BACKGROUND

Haemophilia B, an X-linked life threatening bleeding disorder affects 1:30,000 males. Current treatment involves frequent intravenous injections (2-3 times per week) of Factor IX (FIX) protein. This treatment is highly effective at arresting bleeding but it is not curative and is extremely expensive (£150,000/patient/year), thus making it unaffordable by the majority of haemophilia B patients in the world. Gene therapy for haemophilia B offers the potential for a cure through persistent, endogenous production of Factor IX following the transfer of a functioning copy of the Factor IX gene to an affected patient.

The present application relates to a gene therapy approach for treating haemophilia B, involving administering a vector comprising a polynucleotide encoding Factor IX. Such a gene therapy approach would avoid the need for frequent intravenous injections of Factor IX. However, it is difficult to provide an effective gene therapy vector, i.e. one that allows for a high level of Factor IX expression and of the expression of Factor IX which is highly active.

SUMMARY

The present application demonstrates that various modifications to a polynucleotide comprising a Factor IX nucleotide sequence can help to improve the expression level and the activity of the expressed Factor IX polypeptide. For example, the present application demonstrates that the following can improve the efficacy of a polynucleotide comprising a Factor IX nucleotide sequence for treatment of haemophilia B:
  using a codon optimised sequence;
  maintaining a portion of the Factor IX polypeptide that is not codon optimised;
  including an intron or a fragment of an intron;
  providing sequences flanking the intron or fragment of an intron that are not codon optimised;
  using a gain of function mutation;
  using a specific promoter; and/or
  maintaining an AAV genome, comprising the nucleotide, in single stranded form.

These modifications provide a Factor IX sequence which is expressed highly, and which encodes a highly active Factor IX polypeptide or fragment thereof. As demonstrated in the Examples, the polynucleotide of the invention expresses, and provides overall Factor IX activity, at higher levels than other Factor IX encoding polynucleotides, for example those disclosed in WO16/075473.

Accordingly, in a first aspect of the invention, there is provided a polynucleotide comprising a Factor IX nucleotide sequence, wherein the Factor IX nucleotide sequence comprises a coding sequence that encodes a Factor IX protein or fragment thereof and wherein a portion of the coding sequence is not wild type.

In a second aspect of the invention, there is provided a polynucleotide comprising a Factor IX nucleotide sequence, wherein the Factor IX nucleotide sequence comprises a coding sequence that encodes a Factor IX protein or a fragment thereof and the coding sequence comprises: (i) a sequence that is at least 95%, at least 98%, at least 99%, at least 99.5%, at least 99.8%, or 100% identical to SEQ ID NO.1; and (ii) a sequence that is at least 98%, at least 99%, at least 99.5%, at least 99.8%, or 100% identical to SEQ ID NO. 15.

In a third aspect of the invention, there is provided a polynucleotide comprising a Factor IX nucleotide sequence, wherein the Factor IX nucleotide sequence encodes a Factor IX protein or fragment thereof and has at least 97%, at least 98%, at least 99%, at least 99.5%, at least 99.8%, or 100% identity to SEQ ID NO. 5.

In a fourth aspect of the invention, there is provided a viral particle comprising a recombinant genome comprising the polynucleotide of the invention.

In a fifth aspect of the invention, there is provided a composition comprising the polynucleotide or viral particle of the invention and a pharmaceutically acceptable excipient.

In a sixth aspect of the invention, there is provided a method of treatment comprising administering an effective amount of the polynucleotide or viral particle of the invention to a patient.

In a seventh aspect of the invention, there is provided a use of the polynucleotide, viral particle or composition of the invention in the manufacture of a medicament for use in a method of treatment.

The invention described herein also relates to the following aspects:
1. A polynucleotide comprising a Factor IX nucleotide sequence, wherein the Factor IX nucleotide sequence comprises a coding sequence that encodes a Factor IX protein or fragment thereof and wherein a portion of the coding sequence is not wild type.
2. The polynucleotide of aspect 1, wherein the portion of the coding sequence that is not wild type is codon optimised.
3. A polynucleotide comprising a Factor IX nucleotide sequence, wherein the Factor IX nucleotide sequence comprises a coding sequence that encodes a Factor IX protein or a fragment thereof and the coding sequence comprises:
   (i) a sequence that is at least 95%, at least 98%, at least 99%, at least 99.5%, at least 99.8%, or 100% identical to SEQ ID NO.1; and
   (ii) a sequence that is at least 98%, at least 99%, at least 99.5%, at least 99.8%, or 100% identical to SEQ ID NO. 15.
4. The polynucleotide of aspect 3, wherein the sequence that is at least 95%, at least 98%, at least 99%, at least 99.5%, or at least 99.8% identical to SEQ ID NO. 1 is codon optimised.
5. A polynucleotide comprising a Factor IX nucleotide sequence, wherein the Factor IX nucleotide sequence encodes a Factor IX protein or fragment thereof and has at least 97%, at least 98%, at least 99%, at least 99.5%, at least 99.8%, or 100% identity to SEQ ID NO. 5.

6. The polynucleotide of aspect 5, wherein the Factor IX nucleotide sequence comprises a coding sequence and a portion of the coding sequence is codon optimised.
7. The polynucleotide of any one of the preceding aspects, wherein the polynucleotide comprises DNA or RNA.
8. The polynucleotide of any one of aspects 2, 4, 6 or 7, wherein the portion of the coding sequence that is codon optimised is a contiguous portion.
9. The polynucleotide of aspect 2, 4, 6, 7 or 8, wherein the portion of the coding sequence that is codon optimised is codon optimised for expression in the human liver.
10. The polynucleotide of any one of the preceding aspects, wherein a polypeptide encoded by the Factor IX nucleotide sequence is expressed in human liver cells at higher levels compared to a reference wild type Factor IX nucleotide sequence.
11. The polynucleotide of any one of aspects 2, 4, 6 or 7, wherein the portion of the coding sequence that is codon optimised is at least 800, at least 900, at least 1100, less than 1500, less than 1300, less than 1200, between 800 and 1500, between 900 and 1300, between 1100 and 1200, or around 1191 nucleotides in length.
12. The polynucleotide of any one of aspects 2, 4 or 6-11, wherein the portion of the coding sequence that is codon optimised comprises 1, 2, 3, 4, 5 or all of:
    a) exon 3 or a portion of at least 10, at least 15, at least 20, less than 25, between 10 and 25, between 15 and 25, or between 20 and 25 nucleotides of exon 3;
    b) exon 4 or a portion of at least 80, at least 90, at least 100, less than 114, between 80 and 114, between 90 and 114, or between 100 and 114 nucleotides of exon 4;
    c) exon 5 or a portion of at least 90, at least 100, at least 110, less than 129, between 90 and 129, between 100 and 129, or between 110 and 129 nucleotides of exon 5;
    d) exon 6 or a portion of at least 150, at least 180, at least 200, less than 203, between 150 and 203, between 180 and 203, or between 200 and 203 nucleotides of exon 6;
    e) exon 7 or a portion of at least 70, at least 80, at least 90, at least 100, less than 115, between 70 and 115, between 80 and 115, between 90 and 115, or between 100 and 115 nucleotides of exon 7; and/or
    f) exon 8 or a portion of at least 400, at least 450, at least 500, less than 548, between 400 and 548, between 450 and 548, or between 500 and 548 nucleotides of exon 8.
13. The polynucleotide of aspect 12, wherein the portion of the coding sequence that is codon optimised comprises a), b), c), d), e) and f).
14. The polynucleotide of aspect 12 or aspect 13, wherein the portion of the coding sequence that is codon optimised comprises a portion of at least 20 nucleotides of exon 3, a portion of at least 100 nucleotides of exon 4, a portion of at least 110 nucleotides of exon 5, a portion of at least 180 nucleotides of exon 6, a portion of at least 100 nucleotides of exon 7, and a portion of at least 500 nucleotides of exon 8.
15. The polynucleotide of any one of aspects 12-14, wherein the portion of the coding sequence that is codon optimised comprises exon 3, exon 4, exon 5, exon 6, exon 7, and exon 8.
16. The polynucleotide of any one of aspects 2, 4 or 6-15, wherein the portion of the coding sequence that is codon optimised comprises a portion of exon 2, and the portion of exon 2 is less than 160, less than 150, less than 100, less than 75, less than 60, at least 20, at least 30, at least 40, at least 50, between 20 and 160, between 30 and 150, between 30 and 100, between 40 and 75, or around 56 nucleotides in length.
17. The polynucleotide of any one of aspects 2, 4 or 6-16, wherein the portion of the coding sequence that is codon optimised comprises a portion of exon 2 that is between 30 and 100 nucleotides in length.
18. The polynucleotide of any one of aspects 2, 4 or 6-17, wherein the portion of the coding sequence that is codon optimised comprises a reduced number of CpGs compared to a corresponding portion of a reference wild type Factor IX sequence.
19. The polynucleotide of aspect 18, wherein the portion of the coding sequence that is codon optimised comprises less than less than 40, less than 20, less than 18, less than 10, less than 5, or less than 1 CpG.
20. The polynucleotide of aspect 18 or 19, wherein the portion of the coding sequence that is codon optimised is CpG free.
21. The polynucleotide of any one of aspects 2, 4 or 6-20, wherein, in the portion of the coding sequence that is codon optimised, at least 40%, at least 45%, at least 50%, at least 55%, at least 60%, at least 65%, at least 70%, or at least 73% of the codons are selected from the group consisting of:
    a) TTC;
    b) CTG;
    c) ATC;
    d) GTG;
    e) GTC;
    f) AGC;
    g) CCC;
    h) ACC;
    i) GCC;
    j) TAC;
    k) CAC;
    l) CAG;
    m) AAC;
    n) AAA;
    o) AAG;
    p) GAC;
    q) TGC;
    r) AGG;
    s) GGC; and
    t) GAG.
22. The polynucleotide of any one of aspects 2, 4 or 6-21, wherein, in the portion of the coding sequence that is codon optimised:
    a) at least 1, at least 2, at least 4, or at least 5 codons that encode phenylalanine is/are replaced with TTC compared to a reference wild type Factor IX sequence;
    b) at least 60%, at least 65%, or at least 70% of the codons that encode phenylalanine are TTC;
    c) at least 60%, at least 65%, or at least 70% of the codons that encode phenylalanine are TTC and the remainder are TTT; and/or
    d) the codons that encode phenylalanine are TTC, except where the following codon starts with a G.
23. The polynucleotide of any one of aspects 2, 4 or 6-22, wherein, in the portion of the coding sequence that is codon optimised:
    a) at least 5, at least 10, at least 15, or at least 16 codons that encode leucine is/are replaced with CTG compared to a reference wild type Factor IX sequence;
    b) at least 90%, or at least 94% of the codons that encode leucine are CTG; and/or c) at least 90%, or at least 94% of the codons that encode leucine are CTG and the remainder are CTC.

24. The polynucleotide of any one of aspects 2, 4, 6-23, wherein, in the portion of the coding sequence that is codon optimised:
   a) at least 5, at least 10, at least 11, or at least 12 codons that encode isoleucine is/are replaced with ATC compared to a reference wild type Factor IX sequence;
   b) at least 1 of codon ATC is/are replaced with ATT compared to a reference wild type Factor IX sequence, where the following codon starts with a G;
   c) at least 60%, at least 70%, or at least 75% of the codons that encode isoleucine are ATC;
   d) at least 60%, at least 70%, or at least 75% of the codons that encode isoleucine are ATC and the remainder are ATT; and/or
   e) the codons that encode isoleucine are ATC, except where the following codon starts with a G.

25. The polynucleotide of any one of aspects 2, 4 or 6-24, wherein, in the portion of the coding sequence that is codon optimised:
   a) at least 10, at least 15, at least 20, or at least 25 codons that encode valine is/are replaced with GTG compared to a reference wild type Factor IX sequence;
   b) at least 1 codon that encodes valine is/are replaced with GTC compared to a reference wild type Factor IX sequence;
   c) at least 80%, at least 90%, or at least 95% of the codons that encode valine are GTG; and/or
   d) at least 80%, at least 90%, or at least 95% of the codons that encode valine are GTG and the remainder are GTC.

26. The polynucleotide of any one of aspects 2, 4 or 6-25, wherein, in the portion of the coding sequence that is codon optimised:
   a) at least 5, at least 10, at least 12, or at least 13 codons that encode serine is/are replaced with AGC compared to a reference wild type Factor IX sequence;
   b) at least 1, at least 2, or at least 4 codons that encode serine is/are replaced with TCT compared to a reference wild type Factor IX sequence, where the following codon starts with a G;
   c) at least 60%, at least 65%, or at least 70% of the codons that encode serine are AGC; and/or
   d) at least 60%, at least 65%, or at least 70% of the codons that encode serine are AGC and the remainder are TCT or TCC.

27. The polynucleotide of any one of aspects 2, 4 or 6-26, wherein, in the portion of the coding sequence that is codon optimised:
   a) at least 1, at least 2, or at least 5 codons that encode proline is/are replaced with CCC compared to a reference wild type Factor IX sequence;
   b) at least 1 codons that encode proline is/are replaced with CCT compared to a reference wild type Factor IX sequence, where the following codon starts with a G;
   c) at least 50%, at least 55%, or at least 60% of the codons that encode proline are CCC;
   d) at 50%, at least 55%, or at least 60% of the codons that encode proline are CCC and the remainder are CCA or CCT; and/or
   e) the codons that encode proline are CCC, except where the following codon starts with a G.

28. The polynucleotide of any one of aspects 2, 4 or 6-27, wherein, in the portion of the coding sequence that is codon optimised:
   a) at least 6, at least 7, at least 8, or at least 10 codons that encode threonine is/are replaced with ACC compared to a reference wild type Factor IX sequence;
   b) at least 1, or at least 2, codons that encode threonine is/are replaced with ACT compared to a reference wild type Factor IX sequence, where the following codon starts with a G;
   c) at least 45%, at least 50%, or at least 55% of the codons that encode threonine are ACC;
   d) at least 45%, at least 50%, or at least 55% of the codons that encode threonine are ACC and the remainder are ACT; and/or
   e) the codons that encode threonine are ACC, except where the following codon starts with a G.

29. The polynucleotide of any one of aspects 2, 4 or 6-28, wherein, in the portion of the coding sequence that is codon optimised:
   a) at least 1, at least 2, at least 3, or at least 4 codons that encode alanine is/are replaced with GCC compared to a reference wild type Factor IX sequence;
   b) at least 1, at least 2, or at least 3 codons that encode alanine is/are replaced with GCT compared to a reference wild type Factor IX sequence, where the following codon starts with a G;
   c) at least 35%, at least 40%, or at least 43% of the codons that encode alanine are GCC;
   d) at least 35%, at least 40%, or at least 45% of the codons that encode alanine are GCC and the remainder are GCT; and/or
   e) the codons that encode alanine are GCC, except where the following codon starts with a G.

30. The polynucleotide of any one of aspects 2, 4 or 6-29, wherein, in the portion of the coding sequence that is codon optimised:
   a) at least 1, or at least 2 codons that encode tyrosine is/are replaced with TAC compared to a reference wild type Factor IX sequence;
   b) at least 1 of codon TAC is/are replaced with TAT compared to a reference wild type Factor IX sequence, where the following codon starts with a G;
   c) at least 40%, at least 45%, or at least 48% of the codons that encode tyrosine are TAC;
   d) at least 40%, at least 45%, or at least 48% of the codons that encode tyrosine are TAC and the remainder are TAT; and/or
   e) the codons that encode tyrosine are TAC, except where the following codon starts with a G.

31. The polynucleotide of any one of aspects 2, 4 or 6-30, wherein, in the portion of the coding sequence that is codon optimised:
   a) at least 1 codons that encode histidine is/are replaced with CAC compared to a reference wild type Factor IX sequence;
   b) at least 50%, at least 60%, or at least 65% of the codons that encode histidine are CAC;
   c) at least 50%, at least 60%, or at least 65% of the codons that encode histidine are CAC and the remainder are CAT; and/or
   d) the codons that encode histidine are CAC, except where the following codon starts with a G.

32. The polynucleotide of any one of aspects 2, 4 or 6-31, wherein, in the portion of the coding sequence that is codon optimised:
   a) at least 1, at least 2, at least 4, or at least 5 codons that encode glutamine is/are replaced with CAG compared to a reference wild type Factor IX sequence;

b) at least 1 of codon CAG is/are replaced with CAA compared to a reference wild type Factor IX sequence;
c) at least 80%, at least 85%, or at least 90% of the codons that encode glutamine are CAG; and/or
d) at least 80%, at least 85%, or at least 90% of the codons that encode glutamine are CAG and the remainder are CAA.

33. The polynucleotide of any one of aspects 2, 4 or 6-32, wherein, in the portion of the coding sequence that is codon optimised:
a) at least 1, at least 2, at least 4, or at least 5 codons that encode asparagine is/are replaced with AAC compared to a reference wild type Factor IX sequence;
b) at least 60%, at least 65%, or at least 70% of the codons that encode asparagine are AAC;
c) at least 60%, at least 65%, or at least 70% of the codons that encode asparagine are AAC and the remainder are AAT; and/or
d) the codons that encode asparagine are AAC, except where the following codon starts with a G.

34. The polynucleotide of any one of aspects 2, 4 or 6-33, wherein, in the portion of the coding sequence that is codon optimised:
a) at least 5, at least 7, at least 8, or at least 9 codons that encode lysine is/are replaced with AAG compared to a reference wild type Factor IX sequence;
b) at least 1 of codon AAG is/are replaced with AAA compared to a reference wild type Factor IX sequence;
c) at least 80%, at least 90%, or at least 95% of the codons that encode lysine are AAG; and/or
d) at least 80%, at least 90%, or at least 95% of the codons that encode lysine are AAG and the remainder are AAA.

35. The polynucleotide of any one of aspects 2, 4 or 6-34, wherein, in the portion of the coding sequence that is codon optimised:
a) at least 1, at least 2, at least 3, or at least 4 codons that encode aspartate is/are replaced with GAC compared to a reference wild type Factor IX sequence;
b) at least 1 of codon GAC is/are replaced with GAT compared to a reference wild type Factor IX sequence, where the following codon starts with a G;
c) at least 45%, at least 50%, or at least 60% of the codons that encode aspartate are GAC;
d) at least 45%, at least 50%, or at least 60% of the codons that encode aspartate are GAC and the remainder are GAT; and/or
e) the codons that encode aspartate are GAC, except where the following codon starts with a G.

36. The polynucleotide of any one of aspects 2, 4 or 6-35, wherein, in the portion of the coding sequence that is codon optimised:
a) at least 15, at least 20, at least 25, or at least 26 codons that encode glutamate is/are replaced with GAG compared to a reference wild type Factor IX sequence;
b) at least 80%, at least 90%, or at least 95% of the codons that encode glutamate are GAG; and/or
c) at least 80%, at least 90%, or at least 95% of the codons that encode glutamate are GAG and the remainder are GAA.

37. The polynucleotide of any one of aspects 2, 4 or 6-36, wherein, in the portion of the coding sequence that is codon optimised:
a) at least 5, at least 6, at least 7, or at least 8 codons that encode cysteine is/are replaced with TGC compared to a reference wild type Factor IX sequence;
b) at least 1 of codon TGC is/are replaced with TGT compared to a reference wild type Factor IX sequence, where the following codon starts with a G;
c) at least 40%, at least 50%, or at least 55% of the codons that encode cysteine are TGC;
d) at least 40%, at least 50%, or at least 55% of the codons that encode cysteine are TGC and the remainder are TGT; and/or
e) the codons that encode cysteine are TGC, except where the following codon starts with a G.

38. The polynucleotide of any one of aspects 2, 4, or 6-37, wherein, in the portion of the coding sequence that is codon optimised the codons that encode tryptophan are TGG.

39. The polynucleotide of any one of aspects 2, 4, or 6-38, wherein, in the portion of the coding sequence that is codon optimised:
a) at least 5, at least 8, at least 10, or at least 11 codons that encode arginine is/are replaced with AGG compared to a reference wild type Factor IX sequence;
b) at least 1 codon that encodes arginine is/are replaced with AGA compared to a reference wild type Factor IX sequence;
c) at least 60%, at least 70%, or at least 75% of the codons that encode arginine are AGG; and/or
d) at least 60%, at least 70%, or at least 75% of the codons that encode arginine are AGG and the remainder are AGA.

40. The polynucleotide of any one of aspects 2, 4, or 6-39, wherein, in the portion of the coding sequence that is codon optimised:
a) at least 5, at least 10, at least 12, or at least 13 codons that encode glycine is/are replaced with GGC compared to a reference wild type Factor IX sequence;
b) at least 5, at least 6, at least 7, or at least 8 codons that encode glycine is/are replaced with GGG compared to a reference wild type Factor IX sequence, where the following codon starts with a G;
c) at least 50%, at least 55%, or at least 60% of the codons that encode glycine are GGC;
d) at least 50%, at least 55%, or at least 60% of the codons that encode glycine are GGC and the remainder are GGG; and/or
e) the codons that encode glycine are GGC, except where the following codon starts with a G.

41. The polynucleotide of any one of aspects 2, 4, or 6-40, wherein the portion of the coding sequence that is codon optimised comprises codons that encode phenylalanine, leucine, isoleucine, valine, serine, proline, threonine, alanine, tyrosine, histidine, glutamine, asparagine, lysine, aspartate, glutamate, cysteine, tryptophan, arginine, and glycine.

42. The polynucleotide of any one of aspects 2, 4, or 6-41, wherein the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimised portion:
a) at least 5 codons that encode phenylalanine is/are replaced with TTC compared to a reference wild type Factor IX sequence;
b) at least 16 codons that encode leucine is/are replaced with CTG compared to a reference wild type Factor IX sequence;

c) at least 12 codons that encode isoleucine is/are replaced with ATC compared to a reference wild type Factor IX sequence;
d) at least 25 codons that encode valine is/are replaced with GTG compared to a reference wild type Factor IX sequence;
e) at least 13 codons that encode serine is/are replaced with AGC compared to a reference wild type Factor IX sequence;
f) at least 5 codons that encode proline is/are replaced with CCC compared to a reference wild type Factor IX sequence;
g) at least 10 codons that encode threonine is/are replaced with ACC compared to a reference wild type Factor IX sequence;
h) at least 4 codons that encode alanine is/are replaced with GCC compared to a reference wild type Factor IX sequence;
i) at least 2 codons that encode tyrosine is/are replaced with TAC compared to a reference wild type Factor IX sequence;
j) at least 1 codons that encode histidine is/are replaced with CAC compared to a reference wild type Factor IX sequence;
k) at least 5 codons that encode glutamine is/are replaced with CAG compared to a reference wild type Factor IX sequence;
l) at least 5 codons that encode asparagine is/are replaced with AAC compared to a reference wild type Factor IX sequence;
m) at least 9 codons that encode lysine is/are replaced with AAG compared to a reference wild type Factor IX sequence;
n) at least 4 codons that encode aspartate is/are replaced with GAC compared to a reference wild type Factor IX sequence;
o) at least 26 codons that encode glutamate is/are replaced with GAG compared to a reference wild type Factor IX sequence;
p) at least 8 codons that encode cysteine is/are replaced with TGC compared to a reference wild type Factor IX sequence;
q) the codons that encode tryptophan are TGG;
r) at least 11 codons that encode arginine is/are replaced with AGG compared to a reference wild type Factor IX sequence; and
s) at least 13 codons that encode glycine is/are replaced with GGC compared to a reference wild type Factor IX sequence.

43. The polynucleotide of any one of aspects 2, 4, or 6-42, wherein the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimised portion:
a) at least 70% of the codons that encode phenylalanine are TTC;
b) at least 94% of the codons that encode leucine are CTG;
c) at least 75% of the codons that encode isoleucine are ATC;
d) at least 95% of the codons that encode valine are GTG;
e) at least 70% of the codons that encode serine are AGC;
f) at least 60% of the codons that encode proline are CCC;
g) at least 55% of the codons that encode threonine are ACC;
h) at least 43% of the codons that encode alanine are GCC;
i) at least 48% of the codons that encode tyrosine are TAC;
j) at least 65% of the codons that encode histidine are CAC;
k) at least 90% of the codons that encode glutamine are CAG;
l) at least 70% of the codons that encode asparagine are AAC;
m) at least 95% of the codons that encode lysine are AAG;
n) at least 60% of the codons that encode aspartate are GAC;
o) at least 95% of the codons that encode glutamate are GAG;
p) at least 55% of the codons that encode cysteine are TGC;
q) the codons that encode tryptophan are TGG;
r) at least 75% of the codons that encode arginine are AGG; and
s) at least 60% of the codons that encode glycine are GGC.

44. The polynucleotide of any one of aspects 2, 4, or 6-43, wherein the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimised portion:
a) at least 70% of the codons that encode phenylalanine are TTC and the remainder are TTT;
b) at least 94% of the codons that encode leucine are CTG and the remainder are CTC;
c) at least 75% of the codons that encode isoleucine are ATC and the remainder are ATT;
d) at least 95% of the codons that encode valine are GTG;
e) at least 70% of the codons that encode serine are AGC;
f) at least 60% of the codons that encode proline are CCC and the remainder are CCA or CCT;
g) at least 55% of the codons that encode threonine are ACC and the remainder are ACT;
h) at least 43% of the codons that encode alanine are GCC and the remainder are GCT;
i) at least 48% of the codons that encode tyrosine are TAC and the remainder are TAT;
j) at least 65% of the codons that encode histidine are CAC and the remainder are CAT;
k) at least 90% of the codons that encode glutamine are CAG and the remainder are CAA;
l) at least 70% of the codons that encode asparagine are AAC and the remainder are AAT;
m) at least 95% of the codons that encode lysine are AAG and the remainder are AAA;
n) at least 60% of the codons that encode aspartate are GAC and the remainder are GAT;
o) at least 95% of the codons that encode glutamate are GAG and the remainder are GAA;
p) at least 55% of the codons that encode cysteine are TGC and the remainder are TGT;
q) the codons that encode tryptophan are TGG;
r) at least 75% of the codons that encode arginine are AGG and the remainder are AGA; and
s) at least 60% of the codons that encode glycine are GGC and the remainder are GGG.

45. The polynucleotide of any one of aspects 10-44, wherein the reference wild type Factor IX sequence is SEQ ID NO. 9 or SEQ ID NO. 19.

46. The polynucleotide of any one of aspects 2, 4 or 6-45, wherein the portion of the coding sequence that is codon optimised is at least 80%, at least 85%, at least 90%, at least 95%, at least 98%, at least 99%, at least 99.5%, at least 99.8%, or 100% identical to a fragment of at least 800, at least 900, at least 1100, less than 1191, less than 1100, less than 1000, between 800 and 1191, between 900 and 1191, or around 1191 nucleotides of SEQ ID NO. 1.

47. The polynucleotide of aspect 46, wherein the portion of the coding sequence that is codon optimised is at least 80%, at least 85%, at least 90%, at least 95%, at least 98%, at least 99%, at least 99.5%, at least 99.8%, or 100% identical to SEQ ID NO. 1.

48. The polynucleotide of aspect 46 or 47, wherein the portion of the coding sequence that is codon optimised is at least 95% identical to a fragment of between 900 and 1191 nucleotides of SEQ ID NO. 1.

49. The polynucleotide of any one of aspects 46-48, wherein the portion of the coding sequence that is codon optimised is at least 95%, or at least 98% identical to SEQ ID NO. 1.

50. The polynucleotide of any one of the preceding aspects, wherein the coding sequence comprises a portion that is not codon optimised.

51. The polynucleotide of aspect 50, wherein the portion that is not codon optimised is at least 100, at least 150, at least 170, at least 190, less than 250, less than 225, less than 200, or around 195 nucleotides.

52. The polynucleotide of any one of aspects 50 or 51, wherein the portion that is not codon optimised comprises exon 1 or a portion of at least 60, at least 70, at least 80, between 60 and 88, between 70 and 88, or between 80 and 88 nucleotides of exon 1.

53. The polynucleotide of any one of aspects 50-52, wherein the portion that is not codon optimised comprises a portion of at least 50, at least 75, at least 80, at least 90, at least 100, less than 140, less than 120, between 50 and 140, between 75 and 120, or around 107 nucleotides of exon 2.

54. The polynucleotide of any one of aspects 50-53, wherein the portion that is not codon optimised comprises CpGs.

55. The polynucleotide of aspect 54, wherein the portion that is not codon optimised comprises at least 1 or at least 2 CpGs per 100 nucleotides.

56. The polynucleotide of any one of aspects 50-55, wherein the portion that is not codon optimised comprises less than 50%, less than 45%, less than 40%, or less than 35% codons selected from the group consisting of:
a) TTC;
b) CTG;
c) ATC;
d) GTG;
e) GTC;
f) AGC; CCC;
h) ACC;
i) GCC;
j) TAC;
k) CAC;
l) CAG;
m) AAC;
n) AAA;
o) AAG;
p) GAC;
q) TGC;
r) AGG;
s) GGC; and
t) GAG.

57. The polynucleotide of any one of aspects 50-56, wherein the portion that is not codon optimised is at least 80%, at least 85%, at least 90%, at least 95%, at least 98%, at least 99%, at least 99.5%, at least 99.8%, or 100% identical to a fragment of at least 100, at least 150, at least 175, less than 195, less than 190, or less than 180 nucleotides of SEQ ID NO. 15.

58. The polynucleotide of aspect 57, wherein the portion that is not codon optimised is at least 80%, at least 85%, at least 90%, at least 95%, at least 98%, at least 99%, at least 99.5%, at least 99.8%, or 100% identical to SEQ ID NO. 15.

59. The polynucleotide of any one of aspects 50-58, wherein the portion that is not codon optimised is wild type.

60. The polynucleotide of any one of aspects 50-59, wherein the portion that is not codon optimised is at least 90%, at least 95%, at least 98%, at least 99%, at least 99.5%, at least 99.8%, or 100% identical to SEQ ID NO: 15.

61. The polynucleotide of any one of the preceding aspects, wherein the polynucleotide further comprises an intron or a fragment of an intron that interrupts the coding sequence.

62. The polynucleotide of aspect 61, wherein the intron or the fragment of an intron is a portion of a wild type Factor IX intron.

63. The polynucleotide of aspect 61 or 62, wherein the fragment of an intron is less than 500, less than 400, less than 350, less than 300, at least 100, at least 200, at least 250, at least 290, between 100 and 500, between 200 and 400, between 250 and 350, or around 299 nucleotides.

64. The polynucleotide of any one of aspects 61-63, wherein the fragment of an intron is at least 80%, at least 85%, at least 90%, at least 95%, at least 98%, at least 99%, at least 99.5%, at least 99.8%, or 100% identical to a fragment of at least 100, at least 200, at least 250, or at least 290 nucleotides of SEQ ID NO. 3.

65. The polynucleotide of any one of aspects 61-64, wherein the intron or the fragment of an intron is at least 85%, at least 90%, at least 95%, at least 98%, at least 99%, at least 99.5%, at least 99.8%, or 100% identical to SEQ ID NO.3.

66. The polynucleotide of aspect 65, wherein the intron or the fragment of an intron is at least 95%, or at least 98% identical to SEQ ID NO.3.

67. The polynucleotide of any one of aspects 61-66, wherein the intron or the fragment of an intron interrupts the portion that is not codon optimised.

68. The polynucleotide of aspect 67, wherein the intron or the fragment of an intron is flanked by at least 60, at least 70, at least 80, at least 90, or at least 100 nucleotides that are not codon optimised.

69. The polynucleotide of aspect 68, wherein the intron or the fragment of an intron is flanked by between 110 and 120 nucleotides that are not codon optimised at the 5' end and between 100 and 110 nucleotides that are not codon optimised at the 3' end.

70. The polynucleotide of any one of aspects 61-69, wherein the intron or the fragment of an intron is positioned between exon 1 and exon 2.

71. The polynucleotide of any one of aspects 61-70, wherein the intron or the fragment of the intron is a fragment of native intron 1 (intron 1a).

72. The polynucleotide of any one of the preceding aspects, wherein the polynucleotide further comprises a transcription regulatory element.

73. The polynucleotide of aspect 72, wherein the transcription regulatory element comprises a liver-specific promoter.

74. The polynucleotide of aspect 72 or aspect 73, wherein the transcription regulatory element comprises an A1AT promoter or a fragment of an A1AT promoter.

75. The polynucleotide of aspect 74, wherein the fragment of an A1AT promoter is at least 100, at least 120, at least 150, at least 180, less than 255, between 100 and 255, between 150 and 225, between 150 and 300, or between 180 and 255 nucleotides in length.

76. The polynucleotides of aspect 75, wherein the fragment of an A1AT promoter is between 150 and 300 nucleotides in length.

77. The polynucleotides, of any one of aspects 72-76, wherein the transcription regulatory element comprises an enhancer.

78. The polynucleotide of aspect 77, wherein the enhancer is an HCR enhancer or a fragment of an HCR enhancer.

79. The polynucleotide of aspect 78, wherein the fragment of an HCR enhancer is a fragment of at least 80, at least 90, at least 100, less than 192, between 80 and 192, between 90 and 192, between 100 and 250, or between 117 and 192 nucleotides in length.

80. The polynucleotide of aspect 79, wherein the fragment of an HCR enhancer is between 100 and 250 nucleotides in length.

81. The polynucleotide of any one of aspects 72-80, wherein the transcription regulatory element is at least 80%, at least 85%, at least 90%, at least 95%, at least 98%, at least 99%, at least 99.5%, at least 99.8%, or 100% identical to SEQ ID NO. 6.

82. The polynucleotide of aspect 81, wherein the transcription regulatory element has a sequence of SEQ ID NO. 6.

83. The polynucleotide of any one of the preceding aspects, wherein the polynucleotide comprises an enhancer that is at least 80%, at least 85%, at least 90%, at least 95% at least 98%, at least 99%, at least 99.5%, at least 99.8%, or 100% identical to SEQ ID NO. 13.

84. The polynucleotide of any one of the preceding aspects, wherein the polynucleotide comprises an enhancer that is at least 98%, at least 99%, at least 99.5%, at least 99.8%, or 100% identical to SEQ ID NO. 13.

85. The polynucleotide of any one of the preceding aspects, wherein the polynucleotide comprises an enhancer of SEQ ID NO. 13.

86. The polynucleotide of any one of the preceding aspects, wherein the polynucleotide comprises a promoter that is at least 80%, at least 85%, at least 90%, at least 95% at least 98%, at least 99%, at least 99.5%, at least 99.8%, or 100% identical to SEQ ID NO. 14.

87. The polynucleotide of any one of the preceding aspects, wherein the polynucleotide comprises a promoter that is at least 98%, at least 99%, at least 99.5%, at least 99.8%, or 100% identical to SEQ ID NO. 14.

88. The polynucleotide of any one of the preceding aspects, wherein the polynucleotide comprises a promoter of SEQ ID NO. 14.

89. The polynucleotide of any one of the preceding aspects, wherein the Factor IX nucleotide sequence comprises a codon that encodes an amino acid at a position corresponding to codon 384 of wild type factor IX, and wherein the codon that encodes an amino acid at a position corresponding to position 384 of wild type Factor IX encodes alanine or leucine.

90. The polynucleotide of aspect 89, wherein the codon that encodes an amino acid at a position corresponding to position 384 of wild type Factor IX is CTX, wherein X is any nucleotide.

91. The polynucleotide of any one of the preceding aspects, wherein the polynucleotide comprises a Factor IX nucleotide sequence that is at least 80%, at least 85%, at least 90%, at least 95%, at least 98%, at least 99%, at least 99.5%, at least 99.8%, or 100% identical to a fragment at least 1200, at least 1350, or at least 1650 nucleotides of SEQ ID NO. 5.

92. The polynucleotide of any one of the preceding aspects, wherein the polynucleotide comprises a Factor IX nucleotide sequence that is at least 80%, at least 85%, at least 90%, at least 95%, at least 98%, at least 99%, at least 99.5%, at least 99.8%, or 100% identical to SEQ ID NO.5.

93. The polynucleotide of any one of the preceding aspects, wherein:
   (i) the Factor IX nucleotide sequence comprises a sequence that is at least 95%, at least 98%, at least 99%, at least 99.5%, at least 99.8%, or 100% identical to SEQ ID NO.1; and
   (ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.

94. The polynucleotide of any one of the preceding aspects, wherein:
   (i) the Factor IX nucleotide sequence comprises a coding sequence that is at least 95%, at least 98%, at least 99%, at least 99.5%, at least 99.8%, or 100% identical to SEQ ID NO.1;
   (ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine; and
   (iii) the polynucleotide comprises a promoter element that is at least 98%, at least 99%, at least 99.5%, at least 99.8%, or 100% identical to SEQ ID NO. 14 and/or an enhancer element that is at least 98%, at least 99%, at least 99.5%, at least 99.8% or 100% identical to SEQ ID NO. 13.

95. The polynucleotide of any one of the preceding aspects, wherein:
   (i) the Factor IX nucleotide sequence comprises a sequence that is at least 95%, at least 98%, at least 99%, at least 99.5%, at least 99.8%, or 100% identical to SEQ ID NO.1;
   (ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine; and
   (iii) the polynucleotide comprise a transcription regulatory element that is at least 98%, at least 99%, at least 99.5%, at least 99.8%, or 100% identical to SEQ ID NO. 6.

96. The polynucleotide of any one of the preceding aspects, wherein:
   (i) the Factor IX nucleotide sequence comprises a sequence that is at least 95%, at least 98%, at least 99%, at least 99.5%, at least 99.8%, or 100% identical to SEQ ID NO.1;
   (ii) the Factor IX nucleotide sequence comprises a sequence that is at least 98%, at least 99%, at least 99.5%, at least 99.8%, or 100% identical to a corresponding portion of SEQ ID NO: 2; and
(iii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.
97. The polynucleotide of any one of aspects 95 or 96, wherein the Factor IX nucleotide sequence comprises an intron or a fragment of an intron, and the fragment of an intron is at least 98%, at least 99%, at least 99.5%, at least 99.8%, or 100% identical to SEQ ID NO. 3.
98. The polynucleotide of any one of the preceding aspects, wherein:
(i) the Factor IX nucleotide sequence comprises a coding sequence and a portion of the coding sequence is not codon optimised; and
(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.
99. The polynucleotide of any one of the preceding aspects, wherein a polypeptide encoded by the Factor IX nucleotide sequence is expressed in human liver cells at higher levels compared to a polypeptide encoded by a nucleotide sequence comprising a Factor IX nucleotide sequence of SEQ ID NO. 12 and a transcription regulatory element of SEQ ID NO. 7.
100. The polynucleotide of any one of the preceding aspects, wherein a polypeptide encoded by the Factor IX nucleotide sequence is expressed in human liver cells at higher levels compared to a polypeptide encoded by a nucleotide sequence comprising a Factor IX nucleotide sequence of SEQ ID NO. 18 and a transcription regulatory element of SEQ ID NO. 6.
101. The polynucleotide of any one of the preceding aspects, wherein a polypeptide encoded by the Factor IX nucleotide sequence is expressed in human liver cells at a level at least 2, or at least 3 times greater than a polypeptide encoded by a nucleotide sequence comprising a Factor IX nucleotide sequence of SEQ ID NO. 12 or SEQ ID NO. 18 and a transcription regulatory element of SEQ ID NO. 7 or SEQ ID NO. 6.
102. A viral particle comprising a recombinant genome comprising the polynucleotide of any one of the preceding aspects.
103. The viral particle of aspect 102, which is an AAV, adenoviral, or lentiviral viral particle.
104. The viral particle of aspect 103, which is an AAV viral particle.
105. The viral particle of any one of aspects 102-104, wherein the recombinant genome further comprises:
a) AAV2 ITRs;
b) a poly A sequence;
c) an origin of replication; and/or
d) two resolvable ITRs.
106. The viral particle of aspect 105, wherein the recombinant genome is single-stranded and/or comprises two resolvable ITRs.
107. The viral particle of any one of aspects 102-106, wherein the viral particle comprises a capsid selected from the group consisting of:
(i) a capsid having at least 96%, at least 98%, at least 99%, at least 99.5%, at least 99.8% identity or 100% identity to SEQ ID NO.10;
(ii) a capsid having at least 96%, at least 98%, at least 99%, at 99.5%, at least 99.8%, or 100% identity to SEQ ID NO. 17;
(iii) AAVMutC; and
(iv) AAV5.
108. The viral particle of any one of aspects 102-107, wherein on transduction into Huh7 cells, the viral particle expresses Factor IX protein or a fragment thereof having a Factor IX activity greater than the activity of Factor IX expressed from a viral particle comprising a Factor IX nucleotide sequence of SEQ ID NO: 12 and a transcription regulatory element of SEQ ID NO. 7 and/or a viral particle comprising a Factor IX nucleotide sequence of SEQ ID NO. 18 and a transcription regulatory element of SEQ ID NO. 6.
109. The viral particle of aspect 108, wherein the activity is measured using a chromogenic substrate which is specific for Factor Xa.
110. The polynucleotide or viral particle of any one of the preceding aspects, wherein the Factor IX protein fragment is at least 200, at least 250, at least 300, between 200 and 415, between 250 and 415, or between 300 and 415 amino acids in length.
111. The polynucleotide or viral particle of any one of the preceding aspects, wherein the Factor IX protein or fragment thereof comprises a sequence:
a) at least 95%, at least 98%, at least 99%, at least 99.5%, at least 99.8%, or 100% identical to SEQ ID NO. 8; or
b) at least 95%, at least 98%, at least 99%, at least 99.5%, at least 99.8%, or 100% identical to a fragment of SEQ ID NO. 8 at least 200, at least 250, at least 300, between 200 and 415, between 250 and 415, or between 300 and 415 amino acids in length.
112. A composition comprising the polynucleotide or viral particle of any one of the preceding aspects and a pharmaceutically acceptable excipient.
113. The polynucleotide, viral particle or composition of any one of the preceding aspects for use in a method of treatment.
114. The polynucleotide, viral particle or composition for use of aspect 113, wherein the method of treatment comprises administering an effective amount of the polynucleotide or viral particle of any one of aspects 1-111 to a patient.
115. A method of treatment comprising administering an effective amount of the polynucleotide or viral particle of any one of aspects 1-111 to a patient.
116. Use of the polynucleotide, viral particle or composition of any one of aspects 1-111 in the manufacture of a medicament for use in a method of treatment.
117. The use of aspect 116, wherein the method of treatment comprises administering an effective amount of the polynucleotide or viral particle of any one of aspects 1-111 to a patient.
118. The polynucleotide, viral particle, composition, use or method of any one of aspects 112-117, wherein the method of treatment is a method of treating haemophilia.
119. The polynucleotide, viral particle, composition, use or method of aspect 118, wherein the haemophilia is haemophilia B.
120. The polynucleotide, viral particle, composition, use or method of aspect 119, wherein the patient has antibodies or inhibitors to Factor IX.

BRIEF DESCRIPTION OF THE DRAWINGS

FIG. 1A, FIG. 1B, and FIG. 1C—Schematic of FIX transgene cassettes ssLP1.FIXco (FIG. 1C), ssHLP2.TIcodop-FIX-GoF (HTFG) (FIG. 1B) and ssHLP2.TI-ACNP-FIX-GoF (HTAG) (FIG. 1A). ITR=Inverted Terminal Repeat; HLP2 and LP1 are transcription regulatory elements of SEQ ID NOs: 6 and 7, respectively; E=Exon; T1=Truncated Intron 1A; WT=Wild Type; CO=Codon Optimised; ACNP=a codon optimised sequence of the invention.

FIG. 2A, FIG. 2B, and FIG. 2C show the level of FIX antigen in supernatant. FIG. 2A shows level of FIX antigen after HUH7 transduction with AAV2/MutC vectors at MOI of $1\times10^3$, FIG. 2B shows level of FIX antigen after HUH7 transduction with AAV2/MutC vectors at MOI of $5\times10^3$, FIG. 2C shows level of FIX antigen after HUH7 transduction with AAV2/MutC vectors at MOI of $1\times10^4$; FIG. 2D, FIG. 2E, and FIG. 2F show the level of FIX antigen after normalisation using the number of vector genomes present in cell lysate. FIG. 2D shows the level of FIX antigen after normalisation, for transduction with AAV2/MutC vectors at MOI of $1\times10^3$, FIG. 2E shows the level of FIX antigen after normalisation, for transduction with AAV2/MutC vectors at MOI of $5\times10^3$, FIG. 2F shows the level of FIX antigen after normalisation, for transduction with AAV2/MutC vectors at MOI of $1\times10^4$; Error bars represent mean±SD of n=2. $1e3=1\times10^3$; $5e3=5\times10^3$; $1e4=1\times10^4$; MOI=multiplicity of infection.

FIG. 3A, FIG. 3B, and FIG. 3C—Results from HUH7 transduction with AAV2/Mut C vectors—Experiment 2, showing the level of FIX antigen in supernatant. Error bars represent mean±SD of n=3. $1e3=1\times10^3$; $5e3=5\times10^3$; $1e4=1\times10^4$, MOI=multiplicity of infection. FIG. 3A shows activity of FIX after HUH7 transduction with AAV2/MutC vectors at MOI of $1\times10^3$. FIG. 3B shows activity of FIX after HUH7 transduction with AAV2/MutC vectors at MOI of $5\times10^3$. FIG. 3C shows activity of FIX after HUH7 transduction with AAV2/MutC vectors at MOI of $1\times10^4$.

FIG. 4A, FIG. 4B, FIG. 4C, FIG. 4D, and FIG. 4E—Results from HUH7 transduction with AAV2/Mut C vectors—Experiment 2; FIG. 4A shows the level of FIX antigen in supernatant. FIG. 4A shows level of FIX antigen in the supernatant after HUH7 transduction with AAV2/MutC vectors at MOI of $1\times10^3$, FIG. 4B shows level of FIX antigen in the supernatant after HUH7 transduction with AAV2/MutC vectors at MOI of $5\times10^3$, FIG. 4C shows level of FIX antigen in the supernatant after HUH7 transduction with AAV2/MutC vectors at MOI of $1\times10^4$; FIG. 4D and FIG. 4E show the level of FIX antigen after normalisation using the number of vector genomes present in cell lysate. FIG. 4D shows the level of FIX antigen after normalisation, for transduction with AAV2/MutC vectors at MOI of $5\times10^3$, FIG. 4E shows the level of FIX antigen after normalisation, for transduction with AAV2/MutC vectors at MOI of $1\times10^4$; Error bars represent mean±SD of n=3. $1e3=1\times10^3$; $5e3=5\times10^3$; $1e4=1\times10^4$; MOI=multiplicity of infection.

FIG. 6A shows activity of FIX after HUH7 transduction with AAV2/MutC vectors at MOI of $1\times10^3$. FIG. 6B shows activity of FIX after HUH7 transduction with AAV2/MutC vectors at MOI of $5\times10^3$. FIG. 6C shows activity of FIX after HUH7 transduction with AAV2/MutC vectors at MOI of $1\times10^4$.

FIG. 7A shows activity of FIX after HUH7 transduction with AAV2/MutC vectors at MOI of $1\times10^3$. FIG. 7B shows activity of FIX after HUH7 transduction with AAV2/MutC vectors at MOI of $5\times10^3$. FIG. 7C shows activity of FIX after HUH7 transduction with AAV2/MutC vectors at MOI of $1\times10^4$.

FIG. 8A shows activity of FIX after HUH7 transduction with AAV2/MutC vectors at MOI of $1\times10^3$. FIG. 8B shows activity of FIX after HUH7 transduction with AAV2/MutC vectors at MOI of $5\times10^3$. FIG. 8C shows activity of FIX after HUH7 transduction with AAV2/MutC vectors at MOI of $1\times10^4$.

FIG. 6B and FIG. 7B) showing activity of FIX for MOI $5\times10^3$ shown after HUH7 transduction with AAV2/Mut C vectors. Error bars represent mean±SD of n=12. $5e3=5\times10^3$; MOI=multiplicity of infection. Statistical significance determined using a Student's T-test (p=0.0195).

FIG. 11A shows level of FIX antigen, wherein the level of FIX antigen was assessed 3 weeks post-injection (P=0.0007 between ssHLP2.HTAG and sc.LP1.FIXco and p=0.0198 between ssHLP2.HTAG and ssHLP2.HTFG). FIG. 11B shows level of FIX antigen, wherein antigen levels were normalised to vector genome (p=0.0009 between ssHLP2.HTAG and sc.LP1.FIXco and p=0.0039 between ssHLP2.HTAG and ssHLP2.HTFG). n=4 mice. P-values were determined using one-way ANOVA (multiple comparison).

DETAILED DESCRIPTION

General Definitions

Figure 2A:
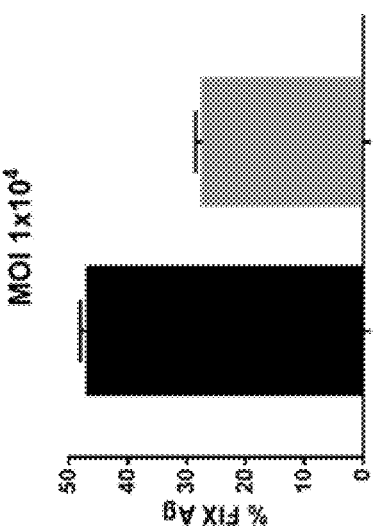
FIG. 2A, FIG. 2B, FIG. 2C, FIG. 2D, FIG. 2E, and FIG. 2F—Results from HUH7 transduction with AAV2/Mut C vectors—Experiment 1.
Figure 2B:
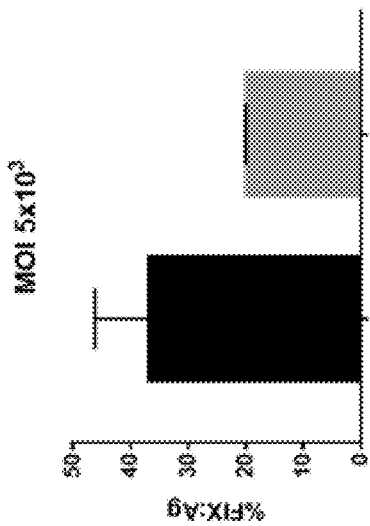
Figure 2C:
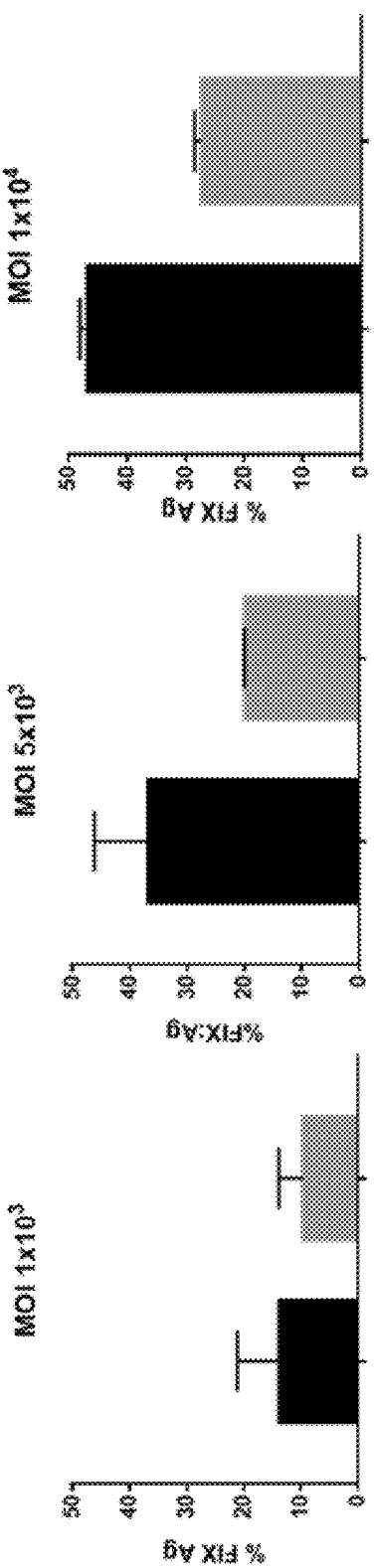
Figure 2D:
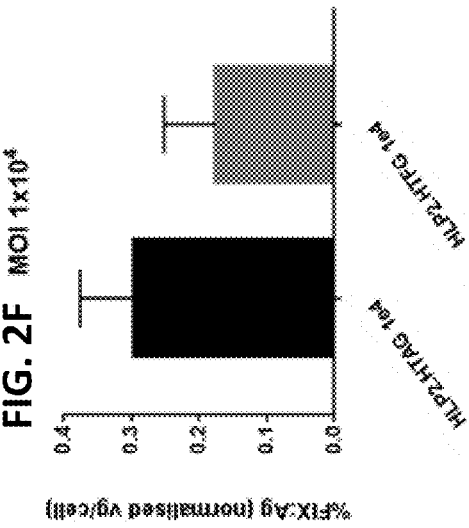
Figure 2E:
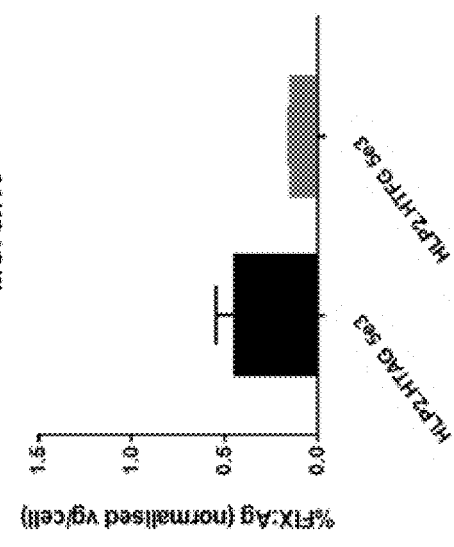
Figure 2F:
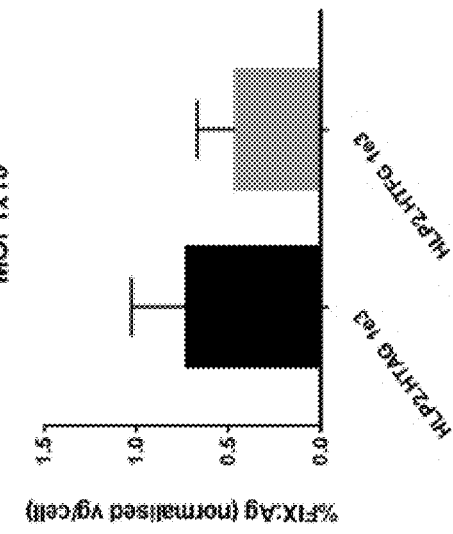

Unless defined otherwise, technical and scientific terms used herein have the same meaning as commonly understood by a person skilled in the art to which this invention belongs.

In general, the term "comprising" is intended to mean including but not limited to. For example, the phrase "a polynucleotide comprising a Factor IX nucleotide sequence" should be interpreted to mean that the polynucleotide has a Factor IX nucleotide sequence, but the polynucleotide may contain additional nucleotides.

In some embodiments of the invention, the word "comprising" is replaced with the phrase "consisting of". The term "consisting of" is intended to be limiting. For example, the phrase "a polynucleotide consisting of a Factor IX nucleotide sequence" should be understood to mean that the polynucleotide has a Factor IX nucleotide sequence and no additional nucleotides.

The terms "protein" and "polypeptide" are used interchangeably herein, and are intended to refer to a polymeric chain of amino acids of any length.

For the purpose of this invention, in order to determine the percent identity of two sequences (such as two polynucleotide or two polypeptide sequences), the sequences are aligned for optimal comparison purposes (e.g., gaps can be introduced in a first sequence for optimal alignment with a second sequence). The nucleotide residues at nucleotide positions are then compared. When a position in the first sequence is occupied by the same nucleotide residue as the corresponding position in the second sequence, then the nucleotides are identical at that position. The percent identity between the two sequences is a function of the number of identical positions shared by the sequences (i.e., % identity=number of identical positions/total number of positions in the reference sequence x 100).

Typically the sequence comparison is carried out over the length of the reference sequence. For example, if the user wished to determine whether a given ("test") sequence is 95% identical to SEQ ID NO. 5, SEQ ID NO. 5 would be the reference sequence. For example, to assess whether a sequence is at least 80% identical to SEQ ID NO. 5 (an example of a reference sequence), the skilled person would carry out an alignment over the length of SEQ ID NO. 5, and identify how many positions in the test sequence were identical to those of SEQ ID NO. 5. If at least 80% of the positions are identical, the test sequence is at least 80% identical to SEQ ID NO. 5. If the sequence is shorter than SEQ ID NO. 5, the gaps or missing positions should be considered to be non-identical positions.

The skilled person is aware of different computer programs that are available to determine the homology or identity between two sequences. For instance, a comparison of sequences and determination of percent identity between two sequences can be accomplished using a mathematical algorithm. In an embodiment, the percent identity between two amino acid or nucleic acid sequences is determined using the Needleman and Wunsch (1970) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6.

For the purposes of the present invention, the term "fragment" refers to a contiguous portion of a sequence. For example, a fragment of SEQ ID NO. 5 of 50 nucleotides refers to 50 contiguous nucleotides of SEQ ID NO. 5.

A Polynucleotide

In one aspect, the present invention provides a polynucleotide comprising a Factor IX nucleotide sequence, wherein the Factor IX nucleotide sequence comprises a coding sequence that encodes a Factor IX protein or fragment thereof and wherein a portion of the Factor IX nucleotide sequence is not wild type.

The polynucleotide may further comprise one or more of the following features. The polynucleotide may comprise a portion that is not codon optimised. The polynucleotide may comprise an intron or a fragment of an intron. The polynucleotide may comprise a mutation in a codon corresponding to codon 384 of wild type Factor IX.

The term "polynucleotide" refers to a polymeric form of nucleotides of any length, deoxyribonucleotides, ribonucleotides, or analogs thereof. For example, the polynucleotide may comprise DNA (deoxyribonucleotides) or RNA (ribonucleotides). The polynucleotide may consist of DNA. The polynucleotide may be mRNA. Since the polynucleotide may comprise RNA or DNA, all references to T (thymine) nucleotides may be replaced with U (uracil).

A Factor IX Nucleotide Sequence

The polynucleotide comprises a Factor IX nucleotide sequence. The Factor IX nucleotide sequence comprises a coding sequence that encodes the Factor IX protein or fragment thereof.

A "coding sequence" is a sequence that encodes a polynucleotide, and excludes non coding regions such as introns. A coding sequence may be interrupted by non-coding nucleotides (e.g. an intron), but only nucleotides that encode the polypeptide should be considered to be part of the coding sequence. For example, a coding sequence that encodes a Factor IX protein will comprise any codons that encode an amino acid forming part of the Factor IX protein that is expressed from that coding sequence, irrespective of whether those codons are contiguous in sequence or separated by one or more non-coding nucleotides. In other words, a polynucleotide which contains stretches of coding nucleotides interrupted by a stretch of non-coding nucleotides will be considered to comprise a "coding sequence" consisting of the non-contiguous coding stretches immediately juxtaposed (i.e. minus the non-coding stretch). However, herein, the stop codon will be considered to be part of the full length coding sequence.

The term "sequence that encodes" refers to a nucleotide sequence comprising codons that encode the encoded polypeptide. For example, a nucleotide sequence that encodes a Factor IX protein or fragment thereof comprises codons that encode the amino acid sequence of the Factor IX protein or fragment thereof. A suitable nucleotide sequence is provided in SEQ ID NO. 5.

The following Table describes codons that encode each amino acid:

| Amino Acid | Codon | Amino Acid | Codon | Amino Acid | Codon |
|---|---|---|---|---|---|
| Phenylalanine | TTC<br>TTT | Proline | CCT<br>CCC<br>CCA<br>CCG | Asparagine | AAT<br>AAC |
| Leucine | TTA<br>TTG<br>CTT<br>CTC<br>CTA<br>CTG | Threonine | ACT<br>ACC<br>ACA<br>ACG | Lysine | AAA<br>AAG |

-continued

| Amino Acid | Codon | Amino Acid | Codon | Amino Acid | Codon |
|---|---|---|---|---|---|
| Isoleucine | ATT | Alanine | GCT | Aspartic Acid | GAT |
|  | ATC |  | GCC |  | GAC |
|  | ATA |  | GCA |  |  |
|  |  |  | GCG |  |  |
| Methionine | ATG | Tyrosine | TAT | Glutamic | GAA |
|  |  |  | TAC | Acid | GAG |
| Valine | GTT | Histidine | CAT | Cysteine | TGT |
|  | GTC |  | CAC |  | TGC |
|  | GTA |  |  |  |  |
|  | GTG |  |  |  |  |
| Serine | TCT | Glutamine | CAA | Tryptophan | TGG |
|  | TCC |  | CAG |  |  |
|  | TCA |  |  |  |  |
|  | TCG |  |  |  |  |
|  | AGT |  |  |  |  |
|  | AGC |  |  |  |  |
| Arginine | CGT | Glycine | GGT |  |  |
|  | CGC |  | GGC |  |  |
|  | CGA |  | GGA |  |  |
|  | CGG |  | GGG |  |  |
|  | AGA |  |  |  |  |
|  | AGG |  |  |  |  |

The corresponding RNA codons will contain Us in place of the Ts in the Table above.

One aspect of the present invention provides a polynucleotide comprising a Factor IX nucleotide sequence, wherein the Factor IX nucleotide sequence encodes a Factor IX protein or fragment thereof and has at least 97%, at least 98%, at least 99%, at least 99.5%, at least 99.8%, or 100% identity to SEQ ID NO. 5. Optionally, the Factor IX nucleotide sequence comprises a coding sequence and a portion of the coding sequence is codon optimised.

In general, the Factor IX nucleotide sequence may be at least 80%, at least 85%, at least 90%, at least 95%, at least 98%, at least 99%, at least 99.5%, at least 99.8%, or 100% identical to a fragment of at least 1200, at least 1350, or at least 1650 nucleotides of SEQ ID NO. 5. The Factor IX nucleotide sequence may be at least 80%, at least 85%, at least 90%, at least 95%, at least 98%, at least 99%, at least 99.5%, at least 99.8%, or 100% identical to a contiguous fragment of at least 1200, at least 1350, or at least 1650 nucleotides of SEQ ID NO. 5. The Factor IX nucleotide sequence may be at least 80%, at least 85%, at least 90%, at least 95%, at least 98%, at least 99%, at least 99.5%, at least 99.8%, or 100% identical to SEQ ID NO.5. For example, the Factor IX nucleotide sequence may be at least 98% identical to SEQ ID NO.5.

Factor IX Protein or Fragment Thereof

The polynucleotide comprises a Factor IX nucleotide sequence comprising a coding sequence that encodes a Factor IX protein or fragment thereof.

Wild type Factor IX is a serine protease, which forms part of the coagulation cascade. Lack of or mutated Factor IX can lead to reduced blood clotting and the disease haemophilia B. A typical wild type Factor IX polypeptide is encoded by SEQ ID NO. 9 (sometimes referred to as Factor IX Malmo B) or SEQ ID NO. 19. An alternative wild type Factor IX polypeptide differs from that encoded by SEQ ID NO. 9 at codon 194, for example codon 194 may encode threonine ("Malmo A") instead of alanine.

Figure 13:
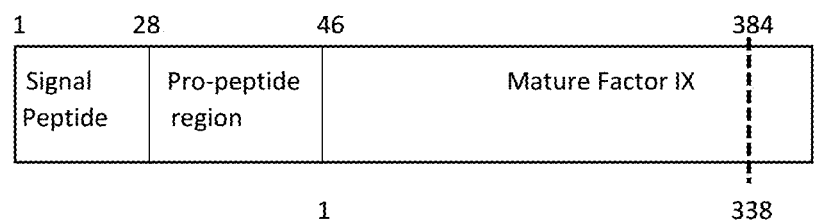
FIG. 13—Schematic of Factor IX structure. The numbers above the schematic represent amino acid positions in the complete Factor IX polypeptide including the signal peptide and the pro-peptide region (encoded by SEQ ID NO. 9). The numbers below the schematic represent equivalent amino acid positions in mature Factor IX (which corresponds to the portion of coding sequence in SEQ ID NO.19).

Factor IX (e.g. a Factor IX of SEQ ID NO. 16) as initially expressed as a precursor "immature" form, comprising a hydrophobic signal peptide (amino acids 1-28 of SEQ ID NO. 16), a pro-peptide region (amino acids 29-46 of SEQ ID NO. 16) and a mature polypeptide region, as set out in FIG. 13. The mature (zymogen) form of Factor IX lacks the hydrophobic signal peptide and the pro-peptide region. The term "mature Factor IX" refers to a Factor IX polypeptide that does not comprise the hydrophobic signal peptide or the pro-peptide region, such as SEQ ID NO. 8.

During clotting the single-chain zymogen form is cleaved by Factor XIa or Factor VIIa to produce an active two-chain form (Factor IXa), with the two chains linked by a disulphide bridge. The activated form can catalyse the hydrolysis of an arginine-isoleucine bond in Factor X to form Factor Xa. Wild type Factor IX is inhibited by thrombin. The wild type Factor IX protein has four protein domains, a Gla domain, two tandem copies of the EGF domain and a C-terminal trypsin-like peptidase domain which is responsible for catalytic cleavage.

The term "Factor IX protein" refers to the single-chain zymogen form of Factor IX, the activated two-chain form and variants thereof, and may refer to the mature Factor IX polypeptide or a Factor IX polypeptide comprising the pro-peptide region and/or the signal peptide region.

Preferably the Factor IX fragment is at least 200, at least 250, at least 300, between 200 and 461, between 250 and 461, or between 300 and 461 amino acids in length. In an embodiment, the Factor IX protein or fragment thereof comprises a sequence:

a) at least 95%, at least 98%, at least 99%, at least 99.5%, at least 99.8%, or 100% identical to SEQ ID NO. 8; or b) at least 95%, at least 98%, at least 99%, at least 99.5%, at least 99.8%, or 100% identical to a fragment of SEQ ID NO. 8 at least 200, at least 250, at least 300, between 200 and 415, between 250 and 415, or between 300 and 415 amino acids in length.

In an embodiment, the Factor IX protein or fragment thereof is at least 95%, at least 98%, at least 99%, at least 99.5%, at least 99.8%, or 100% identical to SEQ ID NO.16; or at least 95%, at least 98%, at least 99%, at least 99.5%, at least 99.8%, or 100% identical to a fragment of SEQ ID NO.16 at least 200, at least 250, at least 300, between 200 and 461, between 250 and 461, or between 300 and 461 amino acids in length. In an embodiment, the Factor IX protein or fragment thereof is at least 95%, at least 98%, at least 99%, at least 99.5%, at least 99.8%, or 100% identical to SEQ ID NO.16; or at least 95%, at least 98%, at least 99%, at least 99.5%, at least 99.8%, or 100% identical to a fragment of SEQ ID NO.16 at least 300, or between 300 and 461 amino acids in length. The Factor IX protein or fragment thereof may have a sequence of SEQ ID NO: 16 or SEQ ID NO: 8.

Preferably the Factor IX protein or fragment thereof is functional. A functional Factor IX protein or fragment is one which carries out hydrolysis of an arginine-isoleucine bond in Factor X to form Factor Xa.

It is within the abilities of the person skilled in the art to determine whether a Factor IX protein or fragment encoded by a Factor IX nucleotide sequence is functional. The skilled person merely needs to express the Factor IX nucleotide sequence, and test whether the expressed protein is active. For example, the skilled person could prepare a viral particle of the invention comprising the Factor IX nucleotide sequence linked to an operable promoter, and transduce cells with the viral particle under conditions suitable for expression of the Factor IX protein or fragment thereof. The activity of the expressed Factor IX protein or fragment thereof can be analysed using a chromogenic assay, such as the activity assay described in Example 3.

For example, a suitable chromogenic assay is as follows. Factor IX is mixed with thrombin, phospholipids, calcium, thrombin activated Factor VIII and Factor XIa. Under these conditions, the Factor XIa activates the Factor IX to form Factor IXa, and the activity of the Factor IXa can catalyse cleavage of a chromogenic substrate (SXa-11) to produce pNA. The level of pNA generated can be measured by determining absorbance at 405 nm, and this is proportional to the activity of the Factor IX in the sample.

The activity can be normalised to compensate for different concentrations of Factor IX in the sample, by measuring the concentration of Factor IX in the sample using a standard ELISA assay, such as the assay described in Example 4, and dividing the activity by the Factor IX concentration. For example, an antibody that binds to Factor IX could be bound to a plate. The sample, comprising the Factor IX at unknown concentration, could be passed over the plate. A second detection antibody that binds to Factor IX could be applied to the plate, and any excess washed off. The detection antibody that remains (i.e. is not washed off) will be bound to Factor IX. The detection antibody could be linked to an enzyme such as horse radish peroxidase. The level of detection antibody that binds to the Factor IX on the plate could be measured by measuring the amount of the detection antibody. For example, if the detection antibody is linked to horse radish peroxidase, the horse radish peroxidase can catalyse the production of a blue reaction product from a substrate such as TMB (3,3',5,5'-tetramethylbenzidine), and the level of the blue product can be detected by absorbance at 450 nm. The level of the blue product is proportional to the amount of detection antibody that remained after the washing step, which is proportional to the amount of Factor IX in the sample.

Optionally, the Factor IX protein or fragment thereof has an activity greater than that of the Factor IX polypeptide encoded by SEQ ID NO. 9, SEQ ID NO. 19, or SEQ ID NO. 12. Optionally, the activity is measured using a chromogenic substrate which is specific for Factor IX, i.e. a substrate which may be altered by Factor IXa to provide a chromogenic signal. A suitable chromogenic substrate is SXa-11.

In an embodiment, the Factor IX protein or fragment thereof comprises a mutation at a position corresponding to position 384 of wild type Factor IX. For example, position 384 (numbering from the start of the signal peptide, i.e. a position corresponding to amino acid 384 of SEQ ID NO. 16) of wild type Factor IX is an arginine residue (R384), but this can be replaced by a different residue. In an embodiment, R384 is replaced with a small, hydrophobic amino acid. For example, the small, hydrophobic amino acid could be alanine, isoleucine, leucine, valine or glycine. Preferably, the Factor IX protein or fragment thereof comprises a leucine at a position corresponding to position 384 in wild type Factor IX, as shown in SEQ ID NO. 16.

A mutation at a position corresponding to position 384 of the wild type sequence may cause a gain-of-function (GoF) mutation, resulting in Factor IX that is hyperfunctional. The advantage of expressing a Factor IX protein containing a mutation at position 384 is that a relatively small increase in protein amount produces a larger increase in overall protein activity.

It is within the abilities of the person skilled in the art to determine whether a given polypeptide has a mutation at a position corresponding to position 384. The person skilled in the art merely needs to align the sequence of the polypeptide sequence with that of a wild type (precursor, immature) Factor IX polypeptide, and determine whether the residue of the former that aligns with the 384$^{th}$ residue of the latter is an arginine. If not, the polypeptide has a mutation at a position corresponding to position 384 in wild type Factor IX. The alignment may be performed using any suitable algorithm such as that of Needleman and Wunsch described above.

A Portion of the Coding Sequence is not Wild Type

A portion of the coding sequence may not be wild type. The wild type Factor IX-encoding nucleotide sequence is represented by SEQ ID NO. 9, and a coding sequence that comprises a portion differing from that of SEQ ID NO. 9 comprises a portion that is not wild type (providing such portion also differs from other Factor IX coding sequences which are regarded also as wild type, for example the Malmo A variant mentioned previously).

In an embodiment, the portion of the coding sequence that is not wild type is codon optimised. To identify whether a coding sequence comprises a portion that is codon optimised, one can align the coding sequence with SEQ ID NO. 9. If any portions of the sequence are not identical to SEQ ID NO. 9, the user should then determine whether they are codon optimised, i.e., whether they comprise at least one codon that has been replaced with a favoured codon, i.e., one of TTC, CTG, ATC, GTG, GTC, AGC, CCC, ACC, GCC, TAC, CAC, CAG, AAC, AAA, AAG, GAC, TGC, AGG, GGC, and GAG. If the portion that is not wild type comprises at least one codon that has been replaced with a favoured codon, then it is codon optimised. Preferably, a contiguous portion of the coding sequence is codon optimised. However, in some embodiments, the portion of the coding sequence which is codon optimised could be split over 2, 3, 4 or 5 regions of the coding sequence. Optionally, the portion of the coding sequence which is not codon optimised is split over less than 3 or less than 2 regions of the coding sequence. A nucleotide sequence can be codon optimised by replacing codons with other codons that are favoured (i.e. reflective of codon bias) in a particular organ or a particular organism (so-called favoured codons). Such a codon optimisation improves expression of the nucleotide sequence in the particular organ or particular organism. For example, if a nucleotide sequence is codon optimised for the human liver, the nucleotide sequence is modified to increase the number of codons that are favoured in the human liver. The skilled person would appreciate that codon-optimising a sequence may not entail changing every codon as at some positions a "favoured codon" may already be present.

Such codon optimisation may be subject to other factors. For example, it can be seen that the presence of CpGs has an adverse effect on expression and so the user may decide not to use favoured codons if their use at certain positions introduces CpGs into the sequence; this will still be considered to be codon optimisation. In an embodiment, a favoured codon that ends with a C nucleotide will not be included in the portion of the coding sequence that is codon optimised, where the next codon in the sequence begins with a G. For example, codon CTC encodes leucine. CTC should not be used for encoding leucine where the next codon in the sequence begins with a G, such as codon GTT.

The present application discloses that certain codons are favoured for expression in the human liver and that reducing the CpG content of a coding sequence, whilst maintaining a high proportion of those favoured codons, improves expression of the coding sequence. The favoured codons are TTC, CTG, ATC, GTG, GTC, AGC, CCC, ACC, GCC, TAC, CAC, CAG, AAC, AAA, AAG, GAC, TGC, AGG, GGC, and GAG.

In one embodiment, the portion of the coding sequence that is codon optimised is codon optimised for expression in the liver, optionally the human liver. A portion of the coding sequence that is codon optimised for expression in the liver may comprise a higher proportion of codons that are favoured in the liver, such as favoured codons TTC, CTG, ATC, GTG, GTC, AGC, CCC, ACC, GCC, TAC, CAC, CAG, AAC, AAA, AAG, GAC, TGC, AGG, GGC, and GAG.

In an embodiment, the following codons are collectively overrepresented in the portion of the coding sequence that is not wild type or is codon optimised: TTC, CTG, ATC, GTG, GTC, AGC, CCC, ACC, GCC, TAC, CAC, CAG, AAC, AAA, AAG, GAC, TGC, AGG, GGC, and GAG. By "collectively overrepresented", is meant that the total number of favoured codons in the portion of the coding sequence which is codon optimised or not wild type is higher than the total number of the favoured codons in the corresponding portion of a wild type Factor IX nucleotide sequence (such as that as SEQ ID NO. 9 or SEQ ID NO. 19).

In a preferred embodiment, in the portion of the coding sequence that is codon optimised there is a greater frequency of the following codons compared to the corresponding portion of a wild type Factor IX nucleotide sequence (such as that of SEQ ID NO.9): TTC, CTG, ATC, GTG, GTC, AGC, CCC, ACC, GCC, TAC, CAC, CAG, AAC, AAA, AAG, GAC, TGC, AGG, GGC, and GAG. Optionally, the following codons are collectively overrepresented in the portion of the coding sequence that is codon optimised, except where their presence results in a CpG: TTC, CTG, ATC, GTG, GTC, AGC, CCC, ACC, GCC, TAC, CAC, CAG, AAC, AAA, AAG, GAC, TGC, AGG, GGC, and GAG. Optionally, the portion of the coding sequence that is codon optimised comprises at least 40%, at least 45%, at least 50%, at least 55%, at least 60%, or at least 65%, at least 70% or at least 73% of codons selected from the group consisting of: TTC, CTG, ATC, GTG, GTC, AGC, CCC, ACC, GCC, TAC, CAC, CAG, AAC, AAA, AAG, GAC, TGC, AGG, GGC, and GAG.

The codon usage in a codon optimised portion of a polynucleotide of the invention (HLP2.T1-ACNP-FIX-GoF) is compared with the codon usage in a corresponding stretch of wild type Factor IX nucleotide sequence (SEQ ID NO.9) in the following table.

TABLE 1

| Amino Acid | Codon | HTAG | % age of codons | Wild type |
|---|---|---|---|---|
| Phe | TTT | 5 | 26 | 12 |
| | TTC | 14 | 74 | 9 |
| Leu | CTT | 0 | | 9 |
| | CTC | 1 | 5 | 5 |
| | CTA | 0 | | 2 |
| | CTG | 19 | 95 | 3 |
| | TTA | 0 | | 6 |
| | TTG | 0 | | 3 |
| Ile | ATT | 5 | 24 | 17 |
| | ATC | 16 | 76 | 7 |
| | ATA | 0 | | 1 |
| Met | TTG | 0 | | 0 |
| | ATG | 2 | 100 | 6 |
| Val | GTT | 0 | | 22 |
| | GTC | 1 | 3 | 3 |
| | GTA | 0 | | 5 |
| | GTG | 33 | 97 | 7 |
| Ser | TCT | 6 | 25 | 6 |
| | TCC | 1 | 4 | 5 |
| | TCA | 0 | | 6 |
| | TCG | 0 | | 0 |
| | AGT | 0 | | 7 |
| | AGC | 17 | 71 | 3 |
| Pro | CCT | 3 | 23 | 4 |
| | CCC | 8 | 62 | 3 |
| | CCA | 2 | 15 | 8 |
| | CCG | 0 | | 0 |

TABLE 1-continued

| Amino Acid | Codon | HTAG | % age of codons | Wild type |
|---|---|---|---|---|
| Thr | ACT | 11 | 39 | 13 |
| | ACC | 17 | 61 | 7 |
| | ACA | 0 | | 10 |
| | ACG | 0 | | 1 |
| Ala | GCT | 11 | 55 | 9 |
| | GCC | 9 | 45 | 5 |
| | GCA | 0 | | 8 |
| | GCG | 0 | | 0 |
| Tyr | TAT | 7 | 50 | 11 |
| | TAC | 7 | 50 | 5 |
| His | CAT | 3 | 33 | 6 |
| | CAC | 6 | 67 | 4 |
| Gln | CAA | 1 | 8 | 7 |
| | CAG | 11 | 92 | 7 |
| Asn | AAT | 7 | 27 | 15 |
| | AAC | 19 | 73 | 17 |
| Lys | AAA | 1 | 4 | 12 |
| | AAG | 24 | 96 | 16 |
| Asp | GAT | 7 | 39 | 12 |
| | GAC | 11 | 61 | 7 |
| Glu | GAA | 1 | 3 | 33 |
| | GAG | 35 | 97 | 10 |
| Cys | TGT | 9 | 43 | 19 |
| | TGC | 12 | 57 | 5 |
| Trp | TGG | 7 | 88 | 7 |
| | TGA | 1 | 13 | 0 |
| Arg | CGT | 0 | | 1 |
| | CGC | 0 | | 1 |
| | CGA | 0 | | 6 |
| | CGG | 0 | | 3 |
| | AGA | 3 | 20 | 8 |
| | AGG | 12 | 80 | 1 |
| Gly | GGT | 0 | | 8 |
| | GGC | 21 | 66 | 9 |
| | GGA | 0 | | 15 |
| | GGG | 11 | 34 | 4 |

The total number of favoured codons in SEQ ID NO. 9 in this region is 120 (30% of the sequence). On the other hand, the total number of favoured codons in the codon optimised portion of HTAG is 293 (73% of the codons).

It is straightforward to determine whether a given portion of a polynucleotide comprises favoured codons. In order to determine the frequency of each codon used in a portion of a nucleotide sequence, the skilled person merely needs to enter the sequence of that portion into one of the readily available algorithms that looks at codon usage and review the results. Alternatively, the user could simply count them.

The codons that are replaced in the codon optimised portion of HTAG compared to the corresponding region of SEQ ID NO.9 are set out in the following table.

TABLE 2

| Amino Acid | Codon replacements | Frequency |
|---|---|---|
| Pro | CCA to CCC | 2 |
| | CCA to CCT | 2 |
| | CCT to CCC | 3 |
| Leu | TTA to CTG | 5 |
| | CTC to CTG | 3 |
| | CTT to CTG | 6 |
| | TTG to CTG | 2 |
| | CTA to CTG | 1 |
| | TTA to TTG | 0 |
| Gly | GGC to GGG | 1 |
| | GGA to GGC | 9 |
| | GGT to GGG | 4 |
| | GGT to GGC | 3 |
| | GGG to GGC | 2 |
| | GGA to GGG | 5 |

TABLE 2-continued

| Amino Acid | Codon replacements | Frequency |
|---|---|---|
| Ile | ATT to ATC | 12 |
| | ATC to ATT | 1 |
| | ATA to ATC | 1 |
| Val | GTA to GTG | 4 |
| | GTC to GTG | 3 |
| | GTG to GTA | |
| | GTT to GTG | 20 |
| | GTA to GTC | 1 |
| Lys | AAA to AAG | 10 |
| | AAC to AAG | |
| | AAG to AAA | 1 |
| Tyr | TAT to TAC | 3 |
| | TAC to TAT | 1 |
| Gln | CAA to CAG | 6 |
| | CAG to CAA | 1 |
| His | CAT to CAC | 2 |
| Glu | GAA to GAG | 27 |
| Cys | TGT to TGC | 9 |
| | TGC to TGT | 1 |
| Ser | AGT to AGC | 3 |
| | TCC to AGC | 4 |
| | AGT to TCT | 3 |
| | TCA to AGC | 3 |
| | TCT to AGC | 4 |
| | TCA to TCT | 1 |
| Ala | GCA to GCC | 3 |
| | GCA to GCT | 4 |
| | GCT to GCC | 2 |
| Arg | CGA to AGG | 5 |
| | AGA to AGG | 5 |
| | CGT to AGG | 1 |
| | CGG to AGG | 1 |
| | CGG to AGA | 1 |
| Thr | ACA to ACC | 6 |
| | ACT to ACC | 4 |
| | ACA to ACT | 3 |
| | ACG to ACC | 1 |
| Phe | TTT to TTC | 5 |
| Asp | GAT to GAC | 5 |
| | GAC to GAT | 1 |
| Asn | AAT to AAC | 6 |
| stop | TAA to TGA | 1 |
| GoF mutation | | 1 |

In an embodiment, in the portion of the coding sequence that is codon optimised:
 a) at least 1, at least 2, at least 4, or at least 5 codons that encode phenylalanine is/are replaced with TTC compared to a reference wild type Factor IX sequence;
 b) at least 60%, at least 65%, or at least 70% of the codons that encode phenylalanine are TTC;
 c) at least 60%, at least 65%, or at least 70% of the codons that encode phenylalanine are TTC and the remainder are TTT; and/or
 d) the codons that encode phenylalanine are TTC, except where the following codon starts with a G.

For example, when we say at least 1 of codon A is replaced with at least 1 of codon B, this refers to replacement of codon A with codon B in at least 1 position compared to a wild type sequence, such as SEQ ID NO. 9. To determine whether such a replacement has taken place, one merely needs to align the test sequence to a wild type Factor IX sequence and see which codons are different. If at least 1 codon in the test sequence corresponding to codon A of wild type Factor IX is codon B in the test sequence, then at least 1 of codon A has been replaced by codon B. For example, if the first codon is TTT in the test sequence and TTC in the wild type Factor IX sequence, the test sequence comprises at least 1 of codon TTC replaced with TTT.

In an embodiment, in the portion of the coding sequence that is codon optimised:
 a) at least 5, at least 10, at least 15, or at least 16 codons that encode leucine is/are replaced with CTG compared to a reference wild type Factor IX sequence;
 b) at least 90%, or at least 94% of the codons that encode leucine are CTG; and/or
 c) at least 90%, or at least 95% of the codons that encode leucine are CTG and the remainder are CTC.

In an embodiment, in the portion of the coding sequence that is codon optimised:
 a) at least 5, at least 10, at least 11, or at least 12 codons that encode isoleucine is/are replaced with ATC compared to a reference wild type Factor IX sequence;
 b) at least 1 of codon ATC is/are replaced with ATT compared to a reference wild type Factor IX sequence, where the following codon starts with a G;
 c) at least 60%, at least 70%, or at least 75% of the codons that encode isoleucine are ATC;
 d) at least 60%, at least 70%, or at least 75% of the codons that encode isoleucine are ATC and the remainder are ATT; and/or
 e) the codons that encode isoleucine are ATC, except where the following codon starts with a G.

In an embodiment, in the portion of the coding sequence that is codon optimised:
 a) at least 10, at least 15, at least 20, or at least 25 codons that encode valine is/are replaced with GTG compared to a reference wild type Factor IX sequence;
 b) at least 1 codon that encodes valine is/are replaced with GTC compared to a reference wild type Factor IX sequence;
 c) at least 80%, at least 90%, or at least 95% of the codons that encode valine are GTG; and/or
 d) at least 80%, at least 90%, or at least 95% of the codons that encode valine are GTG and the remainder are GTC.

In an embodiment, in the portion of the coding sequence that is codon optimised:
 a) at least 5, at least 10, at least 12, or at least 13 codons that encode serine is/are replaced with AGC compared to a reference wild type Factor IX sequence;
 b) at least 1, at least 2, or at least 4 codons that encode serine is/are replaced with TCT compared to a reference wild type Factor IX sequence, where the following codon starts with a G;
 c) at least 60%, at least 65%, or at least 70% of the codons that encode serine are AGC; and/or
 d) at least 60%, at least 65%, or at least 70% of the codons that encode serine are AGC and the remainder are TCT or TCC.

In an embodiment, in the portion of the coding sequence that is codon optimised:
 a) at least 1, at least 2, or at least 5 codons that encode proline is/are replaced with CCC compared to a reference wild type Factor IX sequence;
 b) at least 1 codons that encode proline is/are replaced with CCT compared to a reference wild type Factor IX sequence, where the following codon starts with a G;
 c) at least 50%, at least 55%, or at least 60% of the codons that encode proline are CCC;
 d) at 50%, at least 55%, or at least 60% of the codons that encode proline are CCC and the remainder are CCA or CCT; and/or
 e) the codons that encode proline are CCC, except where the following codon starts with a G.

In an embodiment, in the portion of the coding sequence that is codon optimised:
a) at least 6, at least 7, at least 8, or at least 10 codons that encode threonine is/are replaced with ACC compared to a reference wild type Factor IX sequence;
b) at least 1, or at least 2, codons that encode threonine is/are replaced with ACT compared to a reference wild type Factor IX sequence, where the following codon starts with a G;
c) at least 45%, at least 50%, or at least 55% of the codons that encode threonine are ACC;
d) at least 45%, at least 50%, or at least 55% of the codons that encode threonine are ACC and the remainder are ACT; and/or
e) the codons that encode threonine are ACC, except where the following codon starts with a G.

In an embodiment, in the portion of the coding sequence that is codon optimised:
a) at least 1, at least 2, at least 3, or at least 4 codons that encode alanine is/are replaced with GCC compared to a reference wild type Factor IX sequence;
b) at least 1, at least 2, or at least 3 codons that encode alanine is/are replaced with GCT compared to a reference wild type Factor IX sequence, where the following codon starts with a G;
c) at least 35%, at least 40%, or at least 43% of the codons that encode alanine are GCC;
d) at least 35%, at least 40%, or at least 45% of the codons that encode alanine are GCC and the remainder are GCT; and/or
e) the codons that encode alanine are GCC, except where the following codon starts with a G.

In an embodiment, in the portion of the coding sequence that is codon optimised:
a) at least 1, or at least 2 codons that encode tyrosine is/are replaced with TAC compared to a reference wild type Factor IX sequence;
b) at least 1 of codon TAC is/are replaced with TAT compared to a reference wild type Factor IX sequence, where the following codon starts with a G;
c) at least 40%, at least 45%, or at least 48% of the codons that encode tyrosine are TAC;
d) at least 40%, at least 45%, or at least 48% of the codons that encode tyrosine are TAC and the remainder are TAT; and/or
e) the codons that encode tyrosine are TAC, except where the following codon starts with a G.

In an embodiment, in the portion of the coding sequence that is codon optimised:
a) at least 1 codons that encode histidine is/are replaced with CAC compared to a reference wild type Factor IX sequence;
b) at least 50%, at least 60%, or at least 65% of the codons that encode histidine are CAC;
c) at least 50%, at least 60%, or at least 65% of the codons that encode histidine are CAC and the remainder are CAT; and/or
d) the codons that encode histidine are CAC, except where the following codon starts with a G.

In an embodiment, in the portion of the coding sequence that is codon optimised:
a) at least 1, at least 2, at least 4, or at least 5 codons that encode glutamine is/are replaced with CAG compared to a reference wild type Factor IX sequence;
b) at least 1 of codon CAG is/are replaced with CAA compared to a reference wild type Factor IX sequence;
c) at least 80%, at least 85%, or at least 90% of the codons that encode glutamine are CAG; and/or
d) at least 80%, at least 85%, or at least 90% of the codons that encode glutamine are CAG and the remainder are CAA.

In an embodiment, in the portion of the coding sequence that is codon optimised:
a) at least 1, at least 2, at least 4, or at least 5 codons that encode asparagine is/are replaced with AAC compared to a reference wild type Factor IX sequence;
b) at least 60%, at least 65%, or at least 70% of the codons that encode asparagine are AAC;
c) at least 60%, at least 65%, or at least 70% of the codons that encode asparagine are AAC and the remainder are AAT; and/or
d) the codons that encode asparagine are AAC, except where the following codon starts with a G.

In an embodiment, in the portion of the coding sequence that is codon optimised:
a) at least 5, at least 7, at least 8, or at least 9 codons that encode lysine is/are replaced with AAG compared to a reference wild type Factor IX sequence;
b) at least 1 of codon AAG is/are replaced with AAA compared to a reference wild type Factor IX sequence;
c) at least 80%, at least 90%, or at least 95% of the codons that encode lysine are AAG; and/or
d) at least 80%, at least 90%, or at least 95% of the codons that encode lysine are AAG and the remainder are AAA.

In an embodiment, in the portion of the coding sequence that is codon optimised:
a) at least 1, at least 2, at least 3, or at least 4 codons that encode aspartate is/are replaced with GAC compared to a reference wild type Factor IX sequence;
b) at least 1 of codon GAC is/are replaced with GAT compared to a reference wild type Factor IX sequence, where the following codon starts with a G;
c) at least 45%, at least 50%, or at least 60% of the codons that encode aspartate are GAC;
d) at least 45%, at least 50%, or at least 60% of the codons that encode aspartate are GAC and the remainder are GAT; and/or
e) the codons that encode aspartate are GAC, except where the following codon starts with a G.

In an embodiment, in the portion of the coding sequence that is codon optimised:
a) at least 15, at least 20, at least 25, or at least 26 codons that encode glutamate is/are replaced with GAG compared to a reference wild type Factor IX sequence;
b) at least 80%, at least 90%, or at least 95% of the codons that encode glutamate are GAG; and/or
c) at least 80%, at least 90%, or at least 95% of the codons that encode glutamate are GAG and the remainder are GAA.

In an embodiment, in the portion of the coding sequence that is codon optimised:
a) at least 5, at least 6, at least 7, or at least 8 codons that encode cysteine is/are replaced with TGC compared to a reference wild type Factor IX sequence;
b) at least 1 of codon TGC is/are replaced with TGT compared to a reference wild type Factor IX sequence, where the following codon starts with a G;
c) at least 40%, at least 50%, or at least 55% of the codons that encode cysteine are TGC;
d) at least 40%, at least 50%, or at least 55% of the codons that encode cysteine are TGC and the remainder are TGT; and/or e) the codons that encode cysteine are TGC, except where the following codon starts with a G.

In an embodiment, in the portion of the coding sequence that is codon optimised in the portion of the coding sequence that is codon optimised the codons that encode tryptophan are TGG.

In an embodiment, in the portion of the coding sequence that is codon optimised:
a) at least 5, at least 8, at least 10, or at least 11 codons that encode arginine is/are replaced with AGG compared to a reference wild type Factor IX sequence;
b) at least 1 codon that encodes arginine is/are replaced with AGA compared to a reference wild type Factor IX sequence;
c) at least 60%, at least 70%, or at least 75% of the codons that encode arginine are AGG; and/or
d) at least 60%, at least 70%, or at least 75% of the codons that encode arginine are AGG and the remainder are AGA.

Preferably at least 60%, at least 70%, or at least 75% of the codons that encode arginine are AGG.

In an embodiment, in the portion of the coding sequence that is codon optimised:
a) at least 5, at least 10, at least 12, or at least 13 codons that encode glycine is/are replaced with GGC compared to a reference wild type Factor IX sequence;
b) at least 5, at least 6, at least 7, or at least 8 codons that encode glycine is/are replaced with GGG compared to a reference wild type Factor IX sequence, where the following codon starts with a G;
c) at least 50%, at least 55%, or at least 60% of the codons that encode glycine are GGC;
d) at least 50%, at least 55%, or at least 60% of the codons that encode glycine are GGC and the remainder are GGG; and/or
e) the codons that encode glycine are GGC, except where the following codon starts with a G.

In an embodiment, the portion of the coding sequence that is codon optimised comprises codons that encode phenylalanine, leucine, isoleucine, valine, serine, proline, threonine, alanine, tyrosine, histidine, glutamine, asparagine, lysine, aspartate, glutamate, cysteine, tryptophan, arginine, and glycine.

In an embodiment, the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine and glycine, and in the codon optimised portion:
a) at least 5 codons that encode phenylalanine is/are replaced with TTC compared to a reference wild type Factor IX sequence;
b) at least 16 codons that encode leucine is/are replaced with CTG compared to a reference wild type Factor IX sequence;
c) at least 12 codons that encode isoleucine is/are replaced with ATC compared to a reference wild type Factor IX sequence;
d) at least 25 codons that encode valine is/are replaced with GTG compared to a reference wild type Factor IX sequence;
e) at least 13 codons that encode serine is/are replaced with AGC compared to a reference wild type Factor IX sequence;
f) at least 5 codons that encode proline is/are replaced with CCC compared to a reference wild type Factor IX sequence;
g) at least 10 codons that encode threonine is/are replaced with ACC compared to a reference wild type Factor IX sequence;
h) at least 4 codons that encode alanine is/are replaced with GCC compared to a reference wild type Factor IX sequence;
i) at least 2 codons that encode tyrosine is/are replaced with TAC compared to a reference wild type Factor IX sequence;
j) at least 1 codons that encode histidine is/are replaced with CAC compared to a reference wild type Factor IX sequence;
k) at least 5 codons that encode glutamine is/are replaced with CAG compared to a reference wild type Factor IX sequence;
l) at least 5 codons that encode asparagine is/are replaced with AAC compared to a reference wild type Factor IX sequence;
m) at least 9 codons that encode lysine is/are replaced with AAG compared to a reference wild type Factor IX sequence;
n) at least 4 codons that encode aspartate is/are replaced with GAC compared to a reference wild type Factor IX sequence;
o) at least 26 codons that encode glutamate is/are replaced with GAG compared to a reference wild type Factor IX sequence;
p) at least 8 codons that encode cysteine is/are replaced with TGC compared to a reference wild type Factor IX sequence;
q) the codons that encode tryptophan are TGG;
r) at least 11 codons that encode arginine is/are replaced with AGG compared to a reference wild type Factor IX sequence; and
s) at least 13 codons that encode glycine is/are replaced with GGC compared to a reference wild type Factor IX sequence.

In an embodiment, the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine and glycine, and in the codon optimised portion:
a) at least 70% of the codons that encode phenylalanine are TTC;
b) at least 94% of the codons that encode leucine are CTG;
c) at least 75% of the codons that encode isoleucine are ATC;
d) at least 95% of the codons that encode valine are GTG;
e) at least 70% of the codons that encode serine are AGC;
f) at least 60% of the codons that encode proline are CCC;
g) at least 55% of the codons that encode threonine are ACC;
h) at least 43% of the codons that encode alanine are GCC;
i) at least 48% of the codons that encode tyrosine are TAC;
j) at least 65% of the codons that encode histidine are CAC;
k) at least 90% of the codons that encode glutamine are CAG;
l) at least 70% of the codons that encode asparagine are AAC;
m) at least 95% of the codons that encode lysine are AAG;
n) at least 60% of the codons that encode aspartate are GAC;

o) at least 95% of the codons that encode glutamate are GAG;
p) at least 55% of the codons that encode cysteine are TGC;
q) the codons that encode tryptophan are TGG;
r) at least 75% of the codons that encode arginine are AGG; and
s) at least 60% of the codons that encode glycine are GGC.

In an embodiment, the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine and glycine, and in the codon optimised portion:
a) at least 70% of the codons that encode phenylalanine are TTC and the remainder are TTT;
b) at least 94% of the codons that encode leucine are CTG and the remainder are CTC;
c) at least 75% of the codons that encode isoleucine are ATC and the remainder are ATT;
d) at least 95% of the codons that encode valine are GTG;
e) at least 70% of the codons that encode serine are AGC;
f) at least 60% of the codons that encode proline are CCC and the remainder are CCA or CCT;
g) at least 55% of the codons that encode threonine are ACC and the remainder are ACT;
h) at least 43% of the codons that encode alanine are GCC and the remainder are GCT;
i) at least 48% of the codons that encode tyrosine are TAC and the remainder are TAT;
j) at least 65% of the codons that encode histidine are CAC and the remainder are CAT;
k) at least 90% of the codons that encode glutamine are CAG and the remainder are CAA;
l) at least 70% of the codons that encode asparagine are AAC and the remainder are AAT;
m) at least 95% of the codons that encode lysine are AAG and the remainder are AAA;
n) at least 60% of the codons that encode aspartate are GAC and the remainder are GAT;
o) at least 95% of the codons that encode glutamate are GAG and the remainder are GAA;
p) at least 55% of the codons that encode cysteine are TGC and the remainder are TGT;
q) the codons that encode tryptophan are TGG;
r) at least 75% of the codons that encode arginine are AGG and the remainder are AGA; and
s) at least 60% of the codons that encode glycine are GGC and the remainder are GGG.

The reference wild type Factor IX sequence may be SEQ ID NO. 9 or SEQ ID NO. 19.

The portion that is codon optimised can correspond to a sequence encoding part of or an entire Factor IX protein. For example, the Factor IX protein could be a full length coding sequence (such as a sequence encoding SEQ ID NO. 8 or SEQ ID NO. 16) or a variant thereof, and the entire coding sequence could be codon optimised. Hence, reference herein to "a portion of the coding sequence is codon optimised" should be understood to mean "at least a portion of the coding sequence is codon optimised". In some embodiments, however, a portion of the coding sequence is not codon optimised, for example a portion of the coding sequence is not codon optimised for expression in the liver. In some embodiments, the portion of the coding sequence that is codon optimised is at least 800, at least 900, at least 1100, less than 1500, less than 1300, less than 1200, between 800 and 1500, between 900 and 1300, between 1100 and 1200, or around 1191 nucleotides in length.

In an embodiment, the portion of the coding sequence that is codon optimised comprises exon 3 or a portion of at least 10, at least 15, at least 20, less than 25, between 10 and 25, between 15 and 25, or between 20 and 25 nucleotides of exon 3. In a further embodiment, the portion of the coding sequence that is codon optimised comprises exon 4 or a portion of at least 80, at least 90, at least 100, less than 114, between 80 and 114, between 90 and 114, or between 100 and 114 nucleotides of exon 4. In a further embodiment, the portion of the coding sequence that is codon optimised comprises exon 5 or a portion of at least 90, at least 100, at least 110, less than 129, between 90 and 129, between 100 and 129, or between 110 and 129 nucleotides of exon 5. In a further embodiment, the portion of the coding sequence that is codon optimised comprises exon 6 or a portion of at least 150, at least 180, at least 200, less than 203, between 150 and 203, between 180 and 203, or between 200 and 203 nucleotides of exon 6. In a further embodiment, the portion of the coding sequence that is codon optimised comprises exon 7 or a portion of at least 70, at least 80, at least 90, at least 100, less than 115, between 70 and 115, between 80 and 115, between 90 and 115, or between 100 and 115 nucleotides of exon 7. In a further embodiment, the portion of the coding sequence that is codon optimised comprises exon 8 or a portion of at least 400, at least 450, at least 500, less than 548, between 400 and 548, between 450 and 548, or between 500 and 548 nucleotides of exon 8.

Exon 3 comprises nucleotides 253-277 of wild type Factor IX (such as a Factor IX of SEQ ID NO. 9), or a corresponding sequence in a non-wild-type Factor IX nucleotide sequence. Exon 4 comprises nucleotides 278-391 of wild type Factor IX (such as a Factor IX of SEQ ID NO: 9), or a corresponding sequence in a non-wild-type Factor IX nucleotide sequence. Exon 5 comprises nucleotides 392-520 of wild type Factor IX (such as a Factor IX of SEQ ID NO: 9), or a corresponding sequence in a non-wild-type Factor IX nucleotide sequence. Exon 6 comprises nucleotides 521-723 of wild type Factor IX (such as a Factor IX of SEQ ID NO: 9), or a corresponding sequence in a non-wild-type Factor IX nucleotide sequence. Exon 7 comprises nucleotides 724-838 of wild type Factor IX (such as a Factor IX of SEQ ID NO: 9), or a corresponding sequence in a non-wild-type Factor IX nucleotide sequence. Exon 8 comprises nucleotides 839-1386 of wild type Factor IX (such as a Factor IX of SEQ ID NO: 9), or a corresponding sequence in a non-wild-type Factor IX nucleotide sequence.

Preferably a portion of at least 20 nucleotides of exon 3, a portion of at least 100 nucleotides of exon 4, a portion of at least 110 nucleotides of exon 5, a portion of at least 180 nucleotides of exon 6, a portion of at least 100 nucleotides of exon 7, and a portion of at least 500 nucleotides of exon 8 are codon optimised. The portion of the coding sequence that is codon optimised may comprise exon 3, exon 4, exon 5, exon 6, exon 7 and exon 8. In an embodiment, the portion of the coding sequence that is codon optimised comprises exon 3, exon 4, exon 5, exon 6, exon 7 and exon 8.

In an embodiment, the portion of the coding sequence that is codon optimised comprises a portion of exon 2, and the portion of exon 2 is less than 160, less than 150, less than 100, less than 75, less than 60, at least 20, at least 30, at least 40, at least 50, between 20 and 160, between 30 and 150, between 30 and 100, between 40 and 75, or around 56 nucleotides in length. Exon 2 comprises nucleotides 89-252 of wild type Factor IX (such as a Factor IX of SEQ ID NO: 9), or a corresponding sequence in a non-wild-type Factor IX nucleotide sequence. In a preferred embodiment, the portion of the coding sequence that is codon optimised comprises a portion of exon 2 that is between 30 and 100 nucleotides in length.

It is within the capabilities of the person skilled in the art to determine whether a portion of a sequence encoding a Factor IX protein or fragment thereof corresponds, for example, to exon 8 of wild type Factor IX. The person skilled in the art merely needs to perform a sequence alignment of the sequence encoding the Factor IX protein or fragment thereof with exon 8 using a suitable alignment algorithm such as that of Needleman and Wunsch described above, and determine whether at least part of the nucleotide sequence has greater than 90%, greater than 95%, or greater than 98% identity to exon 8 of SEQ ID NO. 9 (as described above, exon 8 of SEQ ID NO. 9 consists of nucleotides 839-1386 of SEQ ID NO.9).

As discussed above, providing a polynucleotide sequence comprising a coding sequence that is partially or wholly codon optimised can ensure that the encoded polypeptide is expressed at a high level. In one embodiment, a polypeptide encoded by the Factor IX nucleotide sequence is expressed in human liver cells at higher levels compared to the reference wild type Factor IX sequence. The reference wild type Factor IX sequence may be SEQ ID NO: 9. In an embodiment, a polypeptide encoded by the Factor IX nucleotide sequence is expressed in human liver cells at higher levels compared to a polypeptide encoded by a nucleotide sequence comprising a Factor IX nucleotide sequence of SEQ ID NO: 12 and a transcription regulatory element of SEQ ID NO: 7. In an embodiment, a polypeptide encoded by the Factor IX nucleotide sequence is expressed in human liver cells at higher levels compared to a polypeptide encoded by a nucleotide sequence comprising a Factor IX nucleotide sequence of SEQ ID NO: 18 and a transcription regulatory element of SEQ ID NO: 6.

In an embodiment, a polypeptide encoded by the Factor IX nucleotide sequence is expressed in human liver cells at a level at least 1.5, at least 2, at least 2.5, or at least 3 times greater than a polypeptide encoded by a nucleotide sequence comprising a Factor IX nucleotide sequence of SEQ ID NO. 12 or SEQ ID NO. 18 and a transcription regulatory element of SEQ ID NO. 7 or SEQ ID NO. 6. Optionally, a polypeptide encoded by the Factor IX nucleotide sequence is expressed in human liver cells at a level at least 1.5, at least 2, at least 2.5, or at least 3 times greater than a polypeptide encoded by a nucleotide sequence comprising a Factor IX nucleotide sequence of SEQ ID NO. 12 and a transcription regulatory element of SEQ ID NO. 7. Optionally, a polypeptide encoded by the Factor IX nucleotide sequence is expressed in human liver cells at a level at least 1.5, at least 2, at least 2.5, or at least 3 times greater than a polypeptide encoded by a nucleotide sequence comprising a Factor IX nucleotide sequence of SEQ ID NO. 18 and a transcription regulatory element of SEQ ID NO. 6.

The skilled person may determine whether the Factor IX nucleotide sequence is expressed at higher levels compared to a reference sequence by transducing host cells with a viral particle comprising the Factor IX nucleotide sequence, and some cells with a vector comprising the reference sequence. The cells may be cultured under conditions suitable for expressing the Factor IX protein or fragment thereof encoded by the Factor IX nucleotide sequence, and the level of expressed Factor IX protein can be compared. The level of expressed Factor IX protein can be assessed using an ELISA such as that described in the section entitled "Factor IX protein or fragment thereof". Suitable host cells include cultured human liver cells, such as Huh 7 cells.

As discussed above, the presence of CpGs (i.e. CG dinucleotides) may reduce expression efficiency. This is because CpGs may be methylated, and their methylation may lead to gene silencing thereby reducing expression. For this reason, it is preferred that the portion of the coding sequence that is codon optimised comprises a reduced number of CpGs compared to a corresponding portion of a reference wild type Factor IX sequence. In a preferred embodiment, the portion of the coding sequence that is codon optimised comprises than 40, less than 20, less than 10, less than 5, or less than 1 CpG. Preferably, the portion of the coding sequence that is codon optimised is CpG free, i.e. contains no (0) CG dinucleotides.

In an embodiment, the portion of the coding sequence that is codon optimised is at least 80%, at least 85%, at least 90%, at least 95%, at least 98%, at least 99%, at least 99.5%, at least 99.8%, or 100% identical to a fragment of at least 800, at least 900, at least 1100, less than 1191, less than 1100, less than 1000, between 800 and 1191, between 900 and 1191, or around 1191 nucleotides of SEQ ID NO. 1. In an embodiment, the portion of the coding sequence that is codon optimised is at least 80%, at least 85%, at least 90%, at least 95%, at least 98%, at least 99%, at least 99.5%, at least 99.8%, or 100% identical to SEQ ID NO. 1. In an embodiment, the portion of the coding sequence that is codon optimised is at least 95% identical to a fragment of between 900 and 1191 nucleotides of SEQ ID NO. 1. In an embodiment, the portion of the coding sequence that is codon optimised is at least 95%, or at least 98% identical to SEQ ID NO. 1.

The present invention provides a polynucleotide comprising a Factor IX nucleotide sequence, wherein the Factor IX nucleotide sequence comprises a coding sequence that encodes a Factor IX protein or a fragment thereof and the coding sequence comprises a sequence that is at least 95%, at least 98%, at least 99%, at least 99.5%, at least 99.8%, or 100% identical to SEQ ID NO.1 and a sequence that is at least 98%, at least 99%, at least 99.5%, at least 99.8%, or 100% identical to SEQ ID NO. 15. Optionally, the sequence that is at least 95%, at least 98%, at least 99%, at least 99.5%, or at least 99.8% identical to SEQ ID NO. 1 is codon optimised.

Portion of the Coding Sequence that is not Codon Optimised

In an embodiment, the Factor IX nucleotide sequence comprises a portion that is not codon optimised. The portion that is not codon optimised may be a contiguous portion. Including a portion that is not codon optimised may improve expression of the coding sequence, as the portion that is not codon optimised may interact beneficially with other portions of the coding sequence such as an intron or a fragment of an intron. For example, the Factor IX nucleotide sequence may comprise an intron, or a fragment of an intron, and in such cases flanking the intron or the fragment of an intron with wild type Factor IX sequence may help to ensure correct splicing.

The portion that is not codon optimised is not modified to include a greater number of favoured codons compared to the wild type sequence. For example, the portion that is not codon optimised may comprise a similar number of favoured codons to a wild type sequence. The portion that is not codon optimised may comprise less than 50% of codons TTC, CTG, ATC, GTG, GTC, AGC, CCC, ACC, GCC, TAC, CAC, CAG, AAC, AAA, AAG, GAC, TGC, AGG, GGC, and GAG. Optionally, the portion that is not codon optimised comprises less than 50%, less than 45%, or less than 40% codons selected from the group consisting of: TTC, CTG, ATC, GTG, GTC, AGC, CCC, ACC, GCC, TAC, CAC, CAG, AAC, AAA, AAG, GAC, TGC, AGG, GGC, and GAG.

Optionally, the portion that is not codon optimised is not codon optimised for expression in human liver cells. In an embodiment, the portion that is not codon optimised comprises substantially the same number of favoured codons as a corresponding portion of SEQ ID NO. 9. For example, the portion that is not codon optimised may comprise at least 90% of the number of favoured codons as a corresponding portion of SEQ ID NO. 9.

Optionally, the portion that is not codon optimised is at least 100, at least 150, at least 170, at least 190, less than 250, less than 225, less than 200, or around 195 nucleotides in length.

As discussed in more detail below, the Factor IX nucleotide sequence may comprise an intron or a fragment of an intron. In such cases, the intron or the fragment of an intron may be flanked by the portion that is not codon optimised, i.e. some of the portion that is not codon optimised may be adjacent to the 3' end of the intron or the fragment of an intron and some of the portion that is not codon optimised may be adjacent to the 5' end of the intron or the fragment of the intron. The intron or the fragment of an intron may be between exon 1 and exon 2. In such cases, it is advantageous to include a portion that is not codon optimised which portion comprises a portion of exon 1 and a portion of exon 2.

Optionally, the portion that is not codon optimised comprises exon 1 or a portion of at least 60, at least 70, at least 80, between 60 and 88, between 70 and 88, or between 80 and 88 contiguous nucleotides of exon 1. Exon 1 comprises nucleotides 1-88 of wild type Factor IX (such as a Factor IX of SEQ ID NO: 9), or a corresponding sequence in a non-wild-type Factor IX nucleotide sequence. Part of exon 1 may encode the signal peptide region and the pro-peptide region. Optionally, the portion that is not codon optimised comprises or does not comprise the signal peptide and/or pro-peptide regions. Exon 1 may also comprise an additional non-coding stretch of 29 nucleotide at the 5' end. If the Factor IX nucleotide sequence comprises an intron or a fragment of an intron, it is preferable that the portion that is not codon optimised comprises a portion of exon 1 that is adjacent to the intron or the fragment of an intron. For example, if the intron or the fragment of an intron is between exon 1 and exon 2, it is preferable that the portion that is not codon optimised comprises a portion of exon 1 that corresponds to nucleotides 80-88, 70-88, 60-88, 40-88, or 20-88 of SEQ ID NO.9.

Optionally, the portion that is not codon optimised comprises a portion of at least 50, at least 75, at least 80, at least 90, at least 100, less than 140, less than 120, between 50 and 140, between 75 and 120, or around 107 nucleotides of exon 2. For example, if the intron or the fragment of an intron is between exon 1 and exon 2, it is preferable that the portion that is not codon optimised comprises a portion of exon 2 that corresponds to nucleotides 89-100, 89-120, 89-140, 89-160, 89-180, or 89-196 of SEQ ID NO.9.

The portion that is not codon optimised may comprise CpGs, For example, the portion that is not codon optimised may comprise the same number of CpGs as a corresponding portion of SEQ ID NO. 9. The portion that is not codon optimised may comprise at least 1, at least 1.5, or at least 2 CpGs per 100 nucleotides. The portion that is not codon optimised may comprise at least 1, at least 2, at least 3, between 1 and 5, between 2 and 5, or around 5 CpGs.

The portion that is not codon optimised may be at least 80%, at least 85%, at least 90%, at least 95%, at least 98%, at least 99%, at least 99.5%, at least 99.8%, or 100% identical to a fragment of at least 100, at least 150, at least 175, less than 195, less than 190, or less than 180 of SEQ ID NO. 15 or SEQ ID NO: 2. The portion that is not codon optimised may be at least 80%, at least 85%, at least 90%, at least 95%, at least 98%, at least 99%, at least 99.5%, at least 99.8%, or 100% identical to SEQ ID NO. 15 or SEQ ID NO: 2. For example, the portion that is not codon optimised may be at least 98% identical to SEQ ID NO. 15 or SEQ ID NO: 2.

The portion that is not codon optimised may be wild type. SEQ ID NO. 9 is an example of a wild type Factor IX nucleotide coding sequence. Thus, the portion that is not codon optimised may be at least 90%, at least 95%, at least 98%, at least 99%, at least 99.5%, at least 99.8%, or 100% identical to a corresponding portion of SEQ ID NO: 9.

The Factor IX Nucleotide Sequence May Comprise an Intron or a Fragment of an Intron The Factor IX nucleotide sequence may comprise an intron or a fragment of an intron that interrupts the coding sequence. An intron is a sequence of nucleotides that is excised during the process of expression, and does not form part of the coding sequence.

A genomic wild type Factor IX nucleotide sequence comprises introns, that interrupt the Factor IX coding sequence. The presence of an intron may assist in maintaining a high level of expression of wild type Factor IX. Thus, it may be advantageous to include an intron, or at least a fragment of an intron, in a Factor IX nucleotide sequence of the invention. For example, the Factor IX nucleotide sequence may comprise an intron or a fragment of an intron that corresponds to intron 1 in wild type Factor IX. Suitably, the intron is a fragment of intron 1A of wild type Factor IX, such as SEQ ID NO: 3. It has been found that truncating the sequence of intron 1 causes expression of the Factor IX nucleotide sequence to be increased. It is thought that the truncation of intron 1 to form intron 1A may delete a repressor element in the intron. Truncation of the intron 1 sequence also results in the Factor IX nucleotide sequence being shorter which allows more efficient packaging of the Factor IX nucleotide sequence into a viral delivery system in gene therapy embodiments.

The fragment of an intron may be less than 500, less than 400, less than 350, less than 300, at least 100, at least 200, at least 250, at least 290, between 100 and 500, between 200 and 400, between 250 and 350, or around 299 nucleotides. The fragment of an intron may be at least 80%, at least 85%, at least 90%, at least 95%, at least 98%, at least 99%, at least 99.5%, at least 99.8%, or 100% identical to a fragment of at least 100, at least 200, at least 250, or at least 290 nucleotides of SEQ ID NO. 3. The intron or fragment of an intron may be at least 85%, at least 90%, at least 95%, at least 98%, at least 99%, at least 99.5%, at least 99.8%, or 100% identical to SEQ ID NO.3. For example, the intron or the fragment of an intron may be at least 95%, or at least 98% identical to SEQ ID NO.3.

Preferably, the intron or the fragment of an intron interrupts the portion that is not codon optimised i.e. the intron is 5' to a portion that is not codon optimised and 3' to a portion that is not codon optimised in the Factor IX nucleotide sequence. An intron is "flanked by" a sequence that is not codon optimised if the nucleotides immediately 3' and 5' of the intron or close to the 3' and 5' sections of the intron are not codon optimised. "Close to the intron" refers to within 1, within 2, within 3, within 4, within 5, within 6, within 7, within 8, within 8 or within 10 nucleotides of the intron. As discussed above, flanking the intron or the fragment of an intron with a nucleotide sequence that is not codon optimised may help to ensure correct splicing. Optionally, the intron or the fragment of an intron is flanked by at least 60, at least 70, at least 80, at least 90, or at least 100 nucleotides that are not codon optimised. For example, an intron is flanked by 60 nucleotides that are not codon optimised if 40 nucleotides that are immediately 3' of the intron and 20 nucleotides that are immediately 5' of the intron are not codon optimised, or if 30 nucleotides that are immediately 3' of the intron and 30 nucleotides that are immediately 5' of the intron are not codon optimised. Optionally, the intron or the fragment of an intron is flanked by between 110 and 120 nucleotides that are not codon optimised at the 5' end (e.g. immediately 5' of the intron) and between 100 and 110 nucleotides that are not codon optimised at the 3' end (e.g. immediately 3' of the intron).

The intron or the fragment of an intron may be positioned between portions of the coding sequence corresponding to exon 1 and exon 2 of a Factor IX nucleotide sequence. If the intron or the fragment of an intron corresponds to a fragment of intron 1 in wild type Factor IX, it is preferable that the intron or the fragment of an intron is between portions of the coding sequence corresponding to exon 1 and exon 2 of a Factor IX nucleotide sequence.

The Polynucleotide May Further Comprise a Transcription Regulatory Element

The polynucleotide may comprise a transcription regulatory element.

In one embodiment, the transcription regulatory element is at least 80%, at least 85%, at least 90%, at least 95%, at least 98%, at least 99%, at least 99.5%, at least 99.8%, or 100% identical to SEQ ID NO. 6. In an embodiment, the polynucleotide comprises a transcription regulatory element that is at least 98%, at least 99%, at least 99.5%, at least 99.8%, or 100% identical to SEQ ID NO: 6. Optionally, the polynucleotide comprises a transcription regulatory element of SEQ ID NO: 6.

Any appropriate transcription regulatory element may be used, such as HLP2, HLP1, LP1, HCR-hAAT, ApoE-hAAT, and LSP, which are all liver specific transcription regulatory elements. These transcription regulatory elements are described in more detail in the following references: HLP1: McIntosh J. et al., Blood 2013 Apr. 25, 121(17):3335-44; LP1: Nathwani et al., Blood. 2006 Apr. 1, 107(7): 2653-2661; HCR-hAAT: Miao et al., Mol Ther. 2000; 1: 522-532; ApoE-hAAT: Okuyama et al., Human Gene Therapy, 7, 637-645 (1996); and LSP: Wang et al., Proc Natl Acad Sci USA. 1999 Mar. 30, 96(7): 3906-3910. The HLP2 transcription regulatory element has a sequence of SEQ ID NO: 6.

The transcription regulatory element may comprise a promoter and/or an enhancer, such as the promoter element and/or enhancer element from HLP2, HLP1, LP1, HCR-hAAT, ApoE-hAAT, and LSP. Each of these transcription regulatory elements comprises a promoter, an enhancer, and optionally other nucleotides.

In an embodiment, the transcription regulatory element comprises an enhancer which is the human apolipoprotein E (ApoE) hepatic locus control region (HCR; Miao et al (2000), Molecular Therapy 1(6):522), or a fragment thereof. In an embodiment, the transcription regulatory element comprises a fragment of the HCR enhancer which is a fragment of at least 80, at least 90, at least 100, less than 192, between 80 and 192, between 90 and 192, between 100 and 250, or between 117 and 192 nucleotides in length. Optionally, the fragment of the HCR enhancer is between 100 and 250 nucleotides in length.

A suitable HCR enhancer element fragment is described in SEQ ID NO. 13. Optionally, the transcription regulatory element comprises an enhancer that is at least 80, at least 90, at least 100, less than 192, between 80 and 192, between 90 and 192, between 100 and 250, or between 117 and 192 nucleotides in length and the enhancer comprises a polynucleotide sequence that is at least 80%, at least 85%, at least 90%, at least 95%, at least 98%, at least 99%, at least 99.5%, at least 99.8%, or 100% identical SEQ ID NO. 13. Optionally, the transcription regulatory element comprises an enhancer that is between 117 and 192 nucleotides in length and the enhancer comprises a polynucleotide sequence that is at least 98%, at least 99%, at least 99.5%, at least 99.8%, or 100% identical SEQ ID NO. 13. Optionally, the transcription regulatory element comprises an enhancer that is at least 80%, at least 85%, at least 90%, at least 95%, at least 98%, at least 99%, at least 99.5%, at least 99.8%, or 100% identical to a fragment of at least 90, at least 100, or at least 110 nucleotides of SEQ ID NO. 13. Optionally, the polynucleotide comprises an enhancer that is at least 80%, at least 85%, at least 90%, at least 95% at least 98%, at least 99%, at least 99.5%, at least 99.8%, or 100% identical to SEQ ID NO. 13. Optionally, the polynucleotide comprises an enhancer that is at least 98%, at least 99%, at least 99.5%, at least 99.8%, or 100% identical to SEQ ID NO. 13. Optionally, the polynucleotide comprises an enhancer of SEQ ID NO. 13.

In an embodiment, the transcription regulatory element comprises a promoter which is a human alpha-1 anti-trypsin promoter (A1AT; Miao et al (2000), Molecular Therapy 1(6):522), or a fragment thereof. Optionally, a fragment of an A1AT promoter which is at least 100, at least 120, at least 150, at least 180, less than 255, between 100 and 255, between 150 and 225, between 150 and 300, or between 180 and 255 nucleotides in length. Optionally, the fragment of an A1AT promoter is between 150 and 300 nucleotides in length.

A suitable A1AT promoter fragment is described in SEQ ID NO. 14. Optionally, the transcription regulatory element comprises a promoter that is at least 100, at least 120, at least 150, at least 180, less than 255, between 100 and 255, between 150 and 300, or between 180 and 255 nucleotides in length and the promoter comprises a polynucleotide sequence that is at least 80%, at least 85%, at least 90%, at least 95%, at least 98%, at least 99%, at least 99.5%, at least 99.8%, or 100% identical to SEQ ID NO. 14. Optionally, the transcription regulatory element comprises a promoter that is between 180 and 255 nucleotides in length and the promoter comprises a polynucleotide sequence that is at least 98%, at least 99%, at least 99.5%, at least 99.8%, or 100% identical to SEQ ID NO. 14. Optionally, the polynucleotide comprises a promoter that is at least 80%, at least 85%, at least 90%, at least 95%, at least 98%, at least 99%, at least 99.5%, at least 99.8%, or 100% identical to a fragment of at least 100, at least 120, or at least 150 nucleotides of SEQ ID NO. 14. Optionally, the polynucleotide comprises a promoter that is at least 80%, at least 85%, at least 90%, at least 95%, at least 98%, at least 99%, at least 99.5%, at least 99.8%, or 100% identical to SEQ ID NO. 14. Optionally, the polynucleotide comprises a promoter that is at least 98%, at least 99%, at least 99.5%, at least 99.8%, or 100% identical to SEQ ID NO. 14. Optionally, the polynucleotide comprises a promoter of SEQ ID NO. 14.

If the polynucleotide is intended for expression in the liver, the promoter may be a liver-specific promoter. Optionally, the promoter is a human liver-specific promoter.

A "liver-specific promoter" is a promoter that provides a higher level of expression in liver cells compared to other cells in general. For example, the skilled person can determine whether a promoter is a liver-specific promoter by comparing expression of the polynucleotide in liver cells (such as Huh 7 cells) with expression of the polynucleotide in cells from other tissues. If the level of expression is higher in the liver cells, compared to the cells from other tissues, the promoter is a liver-specific promoter.

Gain of Function Mutation

The Factor IX protein or fragment thereof may comprise a gain of function mutation. A gain of function mutation is a mutation that increases the activity of the Factor IX protein or fragment thereof. For example, the gain of function mutation may result in a Factor IX protein or fragment thereof that has an activity at least 1.5-fold, at least 2-fold, at least 2.5-fold, at least 3-fold, at least 4-fold, at least 5-fold, at least 6-fold, at least 6.5-fold, at least 7-fold, at least 7.5-fold, or at least 8-fold or more greater than wild type Factor IX (such as the Factor IX encoded by SEQ ID NO. 9 or SEQ ID NO. 19).

The Factor IX protein or fragment thereof may comprise a mutation at a position corresponding to position 384 of wild type Factor IX (corresponding to codon 384 of SEQ ID NO. 9 or amino acid 384 of the immature polypeptide encoded by SEQ ID NO. 9). A mutation at a position corresponding to position 384 of wild type Factor IX may be a gain of function mutation. For example, replacement of arginine 384 with leucine can lead to a substantial increase in activity.

Whether or not a Factor IX protein comprises a mutation at a position corresponding to position 384 in Factor IX can be determined by aligning the Factor IX protein with SEQ ID NO. 16 using a suitable algorithm such as that of Needleman and Wunsch described above, and determining whether the amino acid that aligns to amino acid 384 (which is leucine in SEQ ID NO. 16) is an arginine residue. If the amino acid that aligns to amino acid 384 of SEQ ID NO. 16 is not an arginine residue then the Factor IX protein has a mutation at a position corresponding to position 384 of wild type Factor IX.

Whether or not a mutation is a gain of function mutation can be determined by comparing the activity of a Factor IX protein comprising the mutation with the activity of a reference Factor IX protein that is identical except for the putative gain of function mutation. The relative activities of these two proteins can be determined using a chromogenic assay such as that discussed under the heading "Factor IX protein or fragment thereof". If the activity of the Factor IX protein comprising the mutation is higher than the activity of the reference protein, the mutation is a gain of function mutation.

Accordingly, the Factor IX nucleotide sequence may comprise a codon that encodes a mutation at a position corresponding to position 384 in Factor IX. For example, the Factor IX nucleotide sequence may comprise a codon that encodes an amino acid at a position corresponding to position 384 of wild type Factor IX that is a small, hydrophobic amino acid. The small, hydrophobic amino acid may be alanine, leucine, isoleucine, glycine, or valine. For example, the small, hydrophobic amino acid may be alanine or leucine. Preferably the small, hydrophobic amino acid is leucine.

The codon that encodes a mutation at a position corresponding to position 384 in wild type Factor IX can be a codon that encodes leucine such as CTX, where X is any nucleotide. Preferably, X is C or G. The codon that encodes an amino acid at a position corresponding to position 384 of wild type Factor IX may be CTC, such as in SEQ ID NO. 4. In alternative embodiments, the codon that encodes an amino acid at a position corresponding to position 384 of wild type Factor IX is TTG or CTG, such as in SEQ ID NO. 11 or SEQ ID NO. 26. For example, reference to SEQ ID NO: 1 herein may be replaced by reference to the corresponding portions of SEQ ID NOs: 26 or 11. In other words, SEQ ID NO:1 may be substituted at nucleotide 957 (C) with G, or at nucleotides 955 (C) and 957 (C) with T and G respectively.

The polynucleotide may comprise a Factor IX sequence that is at least 80%, at least 85%, at least 90%, at least 95%, at least 98%, at least 99%, at least 99.5%, at least 99.8%, or 100% identical to a fragment of at least 1200, at least 1350, or at least 1650 nucleotides of SEQ ID NO. 5. For example, the Factor IX nucleotide sequence may be at least 80%, at least 85%, at least 90%, at least 95%, at least 98%, at least 99%, at least 99.5%, at least 99.8%, or 100% identical to SEQ ID NO. 5.

Suitably, (i) the Factor IX nucleotide sequence comprises a sequence that is at least 95%, at least 98%, at least 99%, at least 99.5%, at least 99.8%, or 100% identical to SEQ ID NO.1; and (ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.

Suitably, (i) the Factor IX nucleotide sequence comprises a coding sequence that is at least 95%, at least 98%, at least 99%, at least 99.5%, at least 99.8%, or 100% identical to SEQ ID NO.1;

(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine; and (iii) the polynucleotide comprises an enhancer element that is at least 98%, at least 99%, at least 99.5%, at least 99.8%, or 100% identical to SEQ ID NO. 13.

Suitably, (i) the Factor IX nucleotide sequence comprises a coding sequence that is at least 95%, at least 98%, at least 99%, at least 99.5%, at least 99.8%, or 100% identical to SEQ ID NO.1;

(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine; and (iii) the polynucleotide comprises a promoter element that is at least 98%, at least 99%, at least 99.5%, at least 99.8%, or 100% identical to SEQ ID NO. 14.

Suitably,
(i) the Factor IX nucleotide sequence comprises a sequence that is at least 95%, at least 98%, at least 99%, at least 99.5%, at least 99.8%, or 100% identical to SEQ ID NO.1;
(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine; and
(iii) the polynucleotide comprises a transcription regulatory element that is at least 98%, at least 99%, at least 99.5%, at least 99.8%, or 100% identical to SEQ ID NO. 6.

Suitably,
(i) the Factor IX nucleotide sequence comprises a sequence that is at least 95%, at least 98%, at least 99%, at least 99.5%, at least 99.8%, or 100% identical to SEQ ID NO.1;
(ii) the Factor IX nucleotide sequence comprises a sequence that is at least 98%, at least 99%, at least 99.5%, at least 99.8%, or 100% identical to SEQ ID NO: 2; and
(iii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.

Suitably, the Factor IX nucleotide sequence comprises an intron or a fragment of an intron, and the fragment of an intron is at least 98%, at least 99%, at least 99.5%, at least 99.8%, or 100% identical to SEQ ID NO. 3.

A Viral Particle Comprising the Polynucleotide

The invention further provides a viral particle comprising a recombinant genome comprising polynucleotides of the invention. For the purposes of the present invention, the term "viral particle" refers to all or part of a virion. For example, the viral particle comprises a recombinant genome and may further comprise a capsid. The viral particle may be a gene therapy vector. Herein, the terms "viral particle" and "vector" are used interchangeably. For the purpose of the present application, a "gene therapy" vector is a viral particle that can be used in gene therapy, i.e. a viral particle that comprises all the required functional elements to express a transgene, such as a Factor IX nucleotide sequence, in a host cell after administration.

Suitable viral particles include a parvovirus, a retrovirus, a lentivirus or a herpes simplex virus. The parvovirus may be an adeno-associated virus (AAV). The viral particle is preferably a recombinant adeno-associated viral (AAV) vector or a lentiviral vector. More preferably, the viral particle is an AAV viral particle. The terms AAV and rAAV are used interchangeably herein.

The genomic organization of all known AAV serotypes is very similar. The genome of AAV is a linear, single-stranded DNA molecule that is less than about 5,000 nucleotides in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

The recombinant viral genome of the invention may comprise ITRs. It is possible for an AAV vector of the invention to function with only one ITR. Thus, the viral genome comprises at least one ITR, but, more typically, two ITRs (generally with one either end of the viral genome, i.e. one at the 5' end and one at the 3' end). There may be intervening sequences between the polynucleotide and one or more of the ITRs. The polynucleotide of the invention may be incorporated into a viral particle located between two regular ITRs or located on either side of an ITR engineered with two D regions.

AAV sequences that may be used in the present invention for the production of AAV vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al, 1997; Srivastava et al, 1983; Chiorini et al, 1999; Rutledge et al, 1998; and Wu et al, 2000. AAV serotype 1, 2, 3, 3B, 4, 5, 6, 7, 8, 9, 10, 11 or 12 may be used in the present invention. The sequences from the AAV serotypes may be mutated or engineered when being used in the production of gene therapy vectors.

Optionally, an AAV vector comprises ITR sequences which are derived from AAV1, AAV2, AAV4 and/or AAV6. Preferably the ITR sequences are AAV2 ITR sequences. Herein, the term AAVx/y refers to a viral particle that comprises some components from AAVx (wherein x is a AAV serotype number) and some components from AAVy (wherein y is the number of the same or different serotype). For example, an AAV2/8 vector may comprise a portion of a viral genome, including the ITRs, from an AAV2 strain, and a capsid derived from an AAV8 strain.

In an embodiment, the viral particle is an AAV viral particle comprising a capsid. AAV capsids are generally formed from three proteins, VP1, VP2 and VP3. The amino acid sequence of VP1 comprises the sequence of VP2. The portion of VP1 which does not form part of VP2 is referred to as VP1 unique or VP1U. The amino acid sequence of VP2 comprises the sequence of VP3. The portion of VP2 which does not form part of VP3 is referred to as VP2 unique or VP2U. Preferably the capsid is an AAV5 capsid or a Mut C capsid. The Mut C capsid may have at least 96%, at least 98%, at least 99%, at least 99.5%, at least 99.8% identity or 100% identity to SEQ ID NO.10. The AAV capsid may have at least 96%, at least 98%, at least 99%, at 99.5%, at least 99.8%, or 100% identity to SEQ ID NO. 17. In an alternative embodiment, the capsid has a VP2U and/or VP3 of SEQ ID NO. 17 and a VP1U sequence having at least 96%, at least 98%, at least 99%, at least 99.5%, at least 99.8%, or 100% identity to SEQ ID NO: 20, SEQ ID NO: 21, SEQ ID NO: 22, SEQ ID NO: 23, SEQ ID NO: 24 or SEQ ID NO: 25.

A viral particle of the invention may be a "hybrid" particle in which the viral ITRs and viral capsid are from different parvoviruses, such as different AAV serotypes. Preferably, the viral ITRs and capsid are from different serotypes of AAV, in which case such viral particles are known as transcapsidated or pseudotyped. Likewise, the parvovirus may have a "chimeric" capsid (e.g., containing sequences from different parvoviruses, preferably different AAV serotypes) or a "targeted" capsid (e.g., a directed tropism). In some embodiments, the recombinant AAV genome comprises intact ITRs, comprising functional terminal resolution sites (TRS). Such an AAV genome may contain one or two resolvable ITRs, i.e. ITRs containing a functional TRS at which site-specific nicking can take place to create a free 3' hydroxyl group which can serve as a substrate for DNA polymerase to unwind and copy the ITR. Preferably, the recombinant genome is single-stranded (i.e., it is packaged into the viral particle in a single-stranded form). Optionally, the recombinant genome is not packaged in self-complementary configuration, i.e. the genome does not comprise a single covalently-linked polynucleotide strand with substantial self-complementary portions that anneal in the viral particle. Alternatively, the recombinant genome may be packaged in "monomeric duplex" form. "Monomeric duplexes" are described in WO 2011/122950. The genome may be packaged as two substantially complementary but non-covalently linked polynucleotides which anneal in the viral particle.

The viral particle may further comprise a poly A sequence. The poly A sequence may be positioned downstream of the nucleotide sequence encoding a functional Factor IX protein. The poly A sequence may be a bovine growth hormone poly A sequence (bGHpA). The poly A sequence may be between 250 and 270 nucleotides in length.

The viral particle of the invention optionally expresses highly in host cells. For example, on transduction in Huh7 cells, the viral particle expresses Factor IX protein or a fragment thereof having a Factor IX activity greater than the activity of Factor IX protein expressed from a viral particle comprising a Factor IX nucleotide sequence of SEQ ID NO: 12 and a transcription regulatory element of SEQ ID NO. 7 and/or a viral particle comprising a Factor IX nucleotide sequence of SEQ ID NO. 18 and a transcription regulatory element of SEQ ID NO. 6. Optionally, after transduction into a population of Huh7 cells, the viral particle expresses Factor IX protein, or a fragment thereof, having a Factor IX activity greater than the activity of Factor IX expressed from a comparable viral particle comprising a Factor IX nucleotide sequence of SEQ ID NO: 12 and a transcription regulatory element of SEQ ID NO. 7 transduced into a comparable population of Huh7 cells. Optionally, after transduction into a population of Huh7 cells, the viral particle expresses Factor IX protein, or a fragment thereof, having a Factor IX activity greater than the activity of Factor IX expressed from a comparable viral particle comprising a Factor IX nucleotide sequence of SEQ ID NO: 18 and a transcription regulatory element of SEQ ID NO. 6 transduced into a comparable population of Huh7 cells. In such embodiments, the term "comparable viral particle" refers to a viral particle that is the same as an AAV viral particle of the invention, except the comparable viral particle comprises a different Factor IX nucleotide sequence and a different transcription regulatory element (those of SEQ ID NO: 12 and SEQ ID NO: 7 or SEQ ID NO: 18 and SEQ ID NO: 6). Optionally, the activity is assessed using a chromogenic assay such as the chromogenic assay discussed above. In this case, however, the activity is not normalised for the Factor IX concentration, so the activity is a function of the level of expression as well as the inherent activity of the Factor IX protein.

Compositions, Methods and Uses

In a further aspect of the invention, there is provided a composition comprising the polynucleotide or vector/viral particle of the invention and a pharmaceutically acceptable excipient.

The pharmaceutically acceptable excipients may comprise carriers, diluents and/or other medicinal agents, pharmaceutical agents or adjuvants, etc. Optionally, the pharmaceutically acceptable excipients comprise saline solution. Optionally, the pharmaceutically acceptable excipients comprise human serum albumin.

The invention further provides a polynucleotide, vector/viral particle or composition of the invention for use in a method of treatment. Optionally the method of treatment comprises administering an effective amount of the polynucleotide or vector/viral particle of the invention to a patient.

The invention further provides a method of treatment comprising administering an effective amount of the polynucleotide or vector/viral particle of the invention to a patient.

The invention further provides use of the polynucleotide, vector/viral particle or composition of the invention in the manufacture of a medicament for use in a method of treatment. Optionally the method of treatment comprises administering an effective amount of the polynucleotide or vector/viral particle of the invention to a patient. Optionally the method of treatment is a gene therapy. A "gene therapy" involves administering a vector/viral particle of the invention that is capable of expressing a transgene (such as a Factor IX nucleotide sequence) in the host to which it is administered.

Optionally, the method of treatment is a method of treating a coagulopathy such as haemophilia (for example haemophilia A or B) or Van Willebrands' disease. Preferably, the coagulopathy is characterised by increased bleeding and/or reduced clotting. Optionally, the method of treatment is a method of treating haemophilia, for example haemophilia B. In some embodiments, the patient is a patient suffering from haemophilia B. Optionally the patient has antibodies or inhibitors to Factor IX. Optionally, the polynucleotide and/or vector/viral particle is administered intravenously. Optionally, the polynucleotide and/or vector/viral particle is for administration only once (i.e. a single dose) to a patient.

When haemophilia B is "treated" in the above method, this means that one or more symptoms of haemophilia are ameliorated. It does not mean that the symptoms of haemophilia are completely remedied so that they are no longer present in the patient, although in some methods, this may be the case. The method of treatment may result in one or more of the symptoms of haemophilia B being less severe than before treatment. Optionally, relative to the situation pre-administration, the method of treatment results in an increase in the amount/concentration of circulating Factor IX in the blood of the patient, and/or the overall level of Factor IX activity detectable within a given volume of blood of the patient, and/or the specific activity (activity per amount of Factor IX protein) of the Factor IX in the blood of the patient.

A "therapeutically effective amount" refers to an amount effective, at dosages and for periods of time necessary, to achieve the desired therapeutic result, such as raising the level of functional factor IX in a subject (so as to lead to functional factor IX production at a level sufficient to ameliorate the symptoms of haemophilia B).

Optionally, the vector/viral particle is administered at a dose of less than $1\times10^{11}$, less than $1\times10^{12}$, less than $5\times10^{12}$, less than $2\times10^{12}$, less than $1.5\times10^{12}$, less than $3\times10^{12}$, less than $1\times10^{13}$, less than $2\times10^{13}$, or less than $3\times10^{13}$ vector genomes per kg of weight of patient. Optionally, the dose of vector/viral particle that is administered is selected such that the subject expresses Factor IX at an activity of 10%-90%, 20%-80%, 30%-70%, 25%-50%, 20%-150%, 30%-140%, 40%-130%, 50%-120%, 60%-110% or 70%-100% of the Factor IX activity of a non-haemophilic healthy subject.

SEQUENCE LISTING

TABLE 3

| Sequence identity number | Sequence description | Nucleotide or Amino Acid Sequence |
|---|---|---|
| 1 | Codon optimised portion of TI-ACNP-FIX-GoF coding sequence | GAGGAGAAGTGCAGCTTTGAGGAGGCCAGGGAGGTGTTTGAGAACACT GAGAGGACCACTGAGTTCTGGAAGCAGTATGTGGATGGGGACCAGTGT GAGAGCAACCCCTGCCTGAATGGGGGCAGCTGCAAGGATGACATCAAC AGCTATGAGTGCTGGTGCCCCTTTGGCTTTGAGGGCAAGAACTGTGAG CTGGATGTGACCTGCAACATCAAGAATGGCAGATGTGAGCAGTTCTGC AAGAACTCTGCTGACAACAAGGTGGTGTGCAGCTGCACTGAGGGCTAC AGGCTGGCTGAGAACCAGAAGAGCTGTGAGCCTGCTGTGCCATTCCCA TGTGGCAGAGTGTCTGTGAGCCAGACCAGCAAGCTGACCAGGGCTGAG GCTGTGTTCCCTGATGTGGACTATGTGAACAGCACTGAGGCTGAAACC ATCCTGGACAACATCACCCAGAGCACCCAGAGCTTCAATGACTTCACC AGGGTGGTGGGGGGGGAGGATGCCAAGCCTGGCCAGTTCCCCTGGCAA GTGGTGCTGAATGGCAAGGTGGATGCCTTCTGTGGGGGCAGCATTGTG AATGAGAAGTGGATTGTGACTGCTGCCCACTGTGTGGAGACTGGGGTG AAGATCACTGTGGTGGCTGGGGAGCACAACATTGAGGAGACTGAGCAC ACTGAGCAGAAGAGGAATGTGATCAGGATCATCCCCCACCACAACTAC AATGCTGCCATCAACAAGTACAACCATGACATTGCCCTGCTGGAGCTG GATGAGCCCCTGGTGCTGAACAGCTATGTGACCCCCATCTGCATTGCT GACAAGGAGTACACCAACATCTTCCTGAAGTTTGGCTCTGGCTATGTG TCTGGCTGGGGCAGGGTGTTCCACAAGGGCAGGTCTGCCCTGGTGCTG CAGTACCTGAGGGTGCCCCTGGTGGACAGGGCCACCTGCCTGCTCAGC ACCAAGTTCACCATCTACAACAACATGTTCTGTGCTGGCTTCCATGAG GGGGGCAGGGACAGCTGCCAGGGGGACTCTGGGGGACCCCCATGTGACT GAGGTGGAGGGCACCAGCTTCCTGACTGGCATCATCAGCTGGGGGGAG GAGTGTGCCATGAAGGGCAAGTATGGCATCTACACCAAAGTCTCCAGA TATGTGAACTGGATCAAGGAGAAGACCAAGCTGACCTGA |
| 2 | Wild type portion of TI-ACNP-FIX-GoF coding sequence, including intron | ATGCAGCGCGTGAACATGATCATGGCAGAATCACCAGGCCTCATCACC ATCTGCCTTTTAGGATATCTACTCAGTGCTGAATGTACAGGTTTGTTT CCTTTTTTAAAATACATTGAGTATGCTTGCCTTTTAGATATAGAAATA TCTGATGCTGTCTTCTTCACTAAATTTTGATTACATGATTTGACAGCA ATATTGAAGAGTCTAACAGCCAGCACGCAGGTTGGTAAGTACTGTGGG AACATCACAGATTTTGGCTCCATGCCCTAAAGAGAAATTGGCTTTCAG ATTATTTGGATTAAAAACAAAGACTTTCTTAAGAGATGTAAAATTTTC ATGATGTTTTCTTTTTTGCTAAAACTAAAGAATTATTCTTTTACATTT CAGTTTTTCTTGATCATGAAAACGCCAACAAAATTCTGAATCGGCCAA AGAGGTATAATTCAGGTAAATTGGAAGAGTTTGTTCAAGGGAACCTTG AGAGAGAATGTATG |
| 3 | Truncated FIX intron 1A | GTTTGTTTCCTTTTTTAAAATACATTGAGTATGCTTGCCTTTTAGATA TAGAAATATCTGATGCTGTCTTCTTCACTAAATTTTGATTACATGATT TGACAGCAATATTGAAGAGTCTAACAGCCAGCACGCAGGTTGGTAAGT ACTGTGGGAACATCACAGATTTTGGCTCCATGCCCTAAAGAGAAATTG GCTTTCAGATTATTTGGATTAAAAACAAAGACTTTCTTAAGAGATGTA AAATTTTCATGATGTTTTCTTTTTTGCTAAAACTAAAGAATTATTCTT TTACATTTCAG |
| 4 | Coding sequence of TI-ACNP-FIX-GoF | ATGCAGCGCGTGAACATGATCATGGCAGAATCACCAGGCCTCATCACC ATCTGCCTTTTAGGATATCTACTCAGTGCTGAATGTACAGTTTTTCTT GATCATGAAAACGCCAACAAAATTCTGAATCGGCCAAAGAGGTATAAT TCAGGTAAATTGGAAGAGTTTGTTCAAGGGAACCTTGAGAGAGAATGT ATGGAGGAGAAGTGCAGCTTTGAGGAGGCCAGGGAGGTGTTTGAGAAC ACTGAGAGGACCACTGAGTTCTGGAAGCAGTATGTGGATGGGGACCAG TGTGAGAGCAACCCCTGCCTGAATGGGGGCAGCTGCAAGGATGACATC AACAGCTATGAGTGCTGGTGCCCCTTTGGCTTTGAGGGCAAGAACTGT GAGCTGGATGTGACCTGCAACATCAAGAATGGCAGATGTGAGCAGTTC TGCAAGAACTCTGCTGACAACAAGGTGGTGTGCAGCTGCACTGAGGGC TACAGGCTGGCTGAGAACCAGAAGAGCTGTGAGCCTGCTGTGCCATTC CCATGTGGCAGAGTGTCTGTGAGCCAGACCAGCAAGCTGACCAGGGCT GAGGCTGTGTTCCCTGATGTGGACTATGTGAACAGCACTGAGGCTGAA ACCATCCTGGACAACATCACCCAGAGCACCCAGAGCTTCAATGACTTC ACCAGGGTGGTGGGGGGGAGGATGCCAAGCCTGGCCAGTTCCCCTGG CAAGTGGTGCTGAATGGCAAGGTGGATGCCTTCTGTGGGGGCAGCATT GTGAATGAGAAGTGGATTGTGACTGCTGCCCACTGTGTGGAGACTGGG GTGAAGATCACTGTGGTGGCTGGGGAGCACAACATTGAGGAGACTGAG |

TABLE 3-continued

| Sequence identity number | Sequence description | Nucleotide or Amino Acid Sequence |
|---|---|---|
| | | CACACTGAGCAGAAGAGGAATGTGATCAGGATCATCCCCCACCACAAC<br>TACAATGCTGCCATCAACAAGTACAACCATGACATTGCCCTGCTGGAG<br>CTGGATGAGCCCCTGGTGCTGAACAGCTATGTGACCCCCATCTGCATT<br>GCTGACAAGGAGTACACCAACATCTTCCTGAAGTTTGGCTCTGGCTAT<br>GTGTCTGGCTGGGGCAGGGTGTTCCACAAGGGCAGGTCTGCCCTGGTG<br>CTGCAGTACCTGAGGGTGCCCCTGGTGGACAGGGCCACCTGCCTGCTC<br>AGCACCAAGTTCACCATCTACAACAACATGTTCTGTGCTGGCTTCCAT<br>GAGGGGGGCAGGGACAGCTGCCAGGGGGACTCTGGGGGCCCCCATGTG<br>ACTGAGGTGGAGGGCACCCAGCTTCCTGACTGGCATCATCAGCTGGGG<br>GAGGAGTGTGCCATGAAGGGCAAGTATGGCATCTACACCAAAGTCTCC<br>AGATATGTGAACTGGATCAAGGAGAAGACCAAGCTGACCTGA |
| 5 | Coding sequence of TI-ACNP-FIX-GoF Factor IX sequence, including intron | ATGCAGCGCGTGAACATGATCATGGCAGAATCACCAGGCCTCATCACC<br>ATCTGCCTTTTAGGATATCTACTCAGTGCTGAATGTACAGGTTTGTTT<br>CCTTTTTTAAAATACATTGAGTATGCTTGCCTTTTAGATATAGAAATA<br>TCTGATGCTGTCTTCTTCACTAAATTTTGATTACATGATTTGACAGCA<br>ATATTGAAGAGTCTAACAGCCAGCACGCAGGTTGGTAAGTACTGTGGG<br>AACATCACAGATTTTGGCTCCATGCCCTAAAGAGAAATTGGCTTTCAG<br>ATTATTTGGATTAAAAACAAAGACTTTCTTAAGAGATGTAAAATTTTC<br>ATGATGTTTCTTTTTTGCTAAAACTAAAGAATTATTCTTTTACATTT<br>CAGTTTTTCTTGATCATGAAAACGCCAACAAAATTCTGAATCGGCTAA<br>AGAGGTATAATTCAGGTAAATTGGAAGAGTTTGTTCAAGGGAACCTTG<br>AGAGAGAATGTATGGAGGAGAAGTGCAGCTTTGAGGAGGCCAGGGAGG<br>TGTTTGAGAACACTGAGAGGACCACTGAGTTCTGGAAGCAGTATGTGG<br>ATGGGGACCAGTGTGAGAGCAACCCCTGCCTGAATGGGGGCAGCTGCA<br>AGGATGACATCAACAGCTATGAGTGCTGGTGCCCCTTTGGCTTTGAGG<br>GCAAGAACTGTGAGCTGGATGTGACCTGCAACATCAAGAATGGCAGAT<br>GTGAGCAGTTCTGCAAGAACTCTGCTGACAACAAGGTGGTGTGCAGCT<br>GCACTGAGGGCTACAGGCTGGCTGAGAACCAGAAGAGCTGTGAGCCTG<br>CTGTGCCATTCCCATGTGGCAGAGTGTCTGTGAGCCAGACCAGCAAGC<br>TGACCAGGGCTGAGGCTGTGTTCCCTGATGTGGACTATGTGAACAGCA<br>CTGAGGCTGAAACCATCCTGGACAACATCACCCAGAGCACCCAGAGCT<br>TCAATGACTTCACCAGGGTGGTGGGGGGGAGGATGCCAAGCCTGGCC<br>AGTTCCCCTGGCAAGTGGTGCTGAATGGCAAGGTGGATGCCTTCTGTG<br>GGGGCAGCATTGTGAATGAGAAGTGGATTGTGACTGCTGCCCACTGTG<br>TGGAGACTGGGGTGAAGATCACTGTGGTGGCTGGGGAGCACAACATTG<br>AGGAGACTGAGCACACTGAGCAGAAGAGGAATGTGATCAGGATCATCC<br>CCCACCACAACTACAATGCTGCCATCAACAAGTACAACCATGACATTG<br>CCCTGCTGGAGCTGGATGAGCCCCTGGTGCTGAACAGCTATGTGACCC<br>CCATCTGCATTGCTGACAAGGAGTACACCAACATCTTCCTGAAGTTTG<br>GCTCTGGCTATGTGTCTGGCTGGGGCAGGGTGTTCCACAAGGGCAGGT<br>CTGCCCTGGTGCTGCAGTACCTGAGGGTGCCCCTGGTGGACAGGGCCA<br>CCTGCCTGCTCAGCACCAAGTTCACCATCTACAACAACATGTTCTGTG<br>CTGGCTTCCATGAGGGGGGCAGGGACAGCTGCCAGGGGGACTCTGGGG<br>GCCCCCATGTGACTGAGGTGGAGGGCACCCAGCTTCCTGACTGGCATCA<br>TCAGCTGGGGGAGGAGTGTGCCATGAAGGGCAAGTATGGCATCTACA<br>CCAAAGTCTCCAGATATGTGAACTGGATCAAGGAGAAGACCAAGCTGA<br>CCTGA |
| 6 | HLP2 transcription regulatory element sequence | CCCTAAAATGGGCAAACATTGCAAGCAGCAAACAGCAAACACACAGCC<br>CTCCCTGCCTGCTGACCTTGGAGCTGGGGCAGAGGTCAGACACCTCTC<br>TGGGCCCATGCCACCTCCAACTGGACACAGGACGCTGTGGTTTCTGAG<br>CCAGGGGGCGACTCAGATCCCAGCCAGTGGACTTAGCCCCTGTTTGCT<br>CCTCCGATAACTGGGGTGACCTTGGTTAATATTCACCAGCAGCCTCCC<br>CCGTTGCCCCTCTGGATCCACTGCTTAAATACGGACGAGGACAGGGCC<br>CTGTCTCCTCAGCTTCAGGCACCACCACTGACCTGGGACAGTGAAT |
| 7 | LP1 transcription regulatory element sequence | CCCTAAAATGGGCAAACATTGCAAGCAGCAAACAGCAAACACACAGCC<br>CTCCCTGCCTGCTGACCTTGGAGCTGGGGCAGAGGTCAGAGACCTCTC<br>TGGGCCCATGCCACCTCCAACATCCACTCGACCCCTTGGAATTTCGGT<br>GGAGAGGAGCAGAGGTTGTCCTGGCGTGGTTTAGGT AGTGTGAGAG<br>GGGAATGACT CCTTTCGGTA AGTGCAGTGG AAGCTGTACA<br>CTGCCCAGGC AAAGCGTCCG GGCAGCGTAG GCGGGCGACT<br>CAGATCCCAG CCAGTGGACT TAGCCCCTGT TTGCTCCTCC<br>GATAACTGGG GTGACCTTGG TTAATATTCA CCAGCAGCCT<br>CCCCCGTTGC CCCTCTGGAT CCACTGCTTA AATACGGACG<br>AGGACAGGGC CCTGTCTCCT CAGCTTCAGG CACCACCACT<br>GACCTGGGAC AGTGAAT |
| 8 | "Mature" Factor IX amino acid sequence encoded by SEQ ID NO: 4 | YNSGKLEEFVQGNLERECMEEKCSFEEAREVFENTERTTEFWKQYVDG<br>DQCESNPCLNGGSCKDDINSYECWCPFGFEGKNCELDVTCNIKNGRCE<br>QFCKNSADNKVVCSCTEGYRLAENQKSCEPAVPFPCGRVSVSQTSKLT<br>RAEAVFPDVDYVNSTEAETILDNITQSTQSFNDFTRVVGGEDAKPGQF<br>PWQVVLNGKVDAFCGGSIVNEKWIVTAAHCVETGVKITVVAGEHNIEE<br>TEHTEQKRNVIRIIPHHNYNAAINKYNHDIALLELDEPLVLNSYVTPI<br>CIADKEYTNIFLKEGSGYVSGWGRVFHKGRSALVLQYLRVPLVDRATC |

TABLE 3-continued

| Sequence identity number | Sequence description | Nucleotide or Amino Acid Sequence |
|---|---|---|
| | | LLSTKFTIYNNMFCAGFHEGGRDSCQGDSGGPHVTEVGTSFLTGIIS<br>WGEECAMKGKYGIYTKVSRYVNWIKEKTKLT |
| 9 | Wild type Factor IX (Malmo B variant) coding sequence | ATGCAGCGCGTGAACATGATCATGGCAGAATCACCAGGCCTCATCACC<br>ATCTGCCTTTTAGGATATCTACTCAGTGCTGAATGTACAGTTTTTCTT<br>GATCATGAAAACGCCAACAAAATTCTGAATCGGCCAAAGAGGTATAAT<br>TCAGGTAAATTGGAAGAGTTTGTTCAAGGGAACCTTGAGAGAGAATGT<br>ATGGAAGAAAAGTGTAGTTTTGAAGAAGCACGAGAAGTTTTTGAAAAC<br>ACTGAAAGAACAACTGAATTTTGGAAGCAGTATGTTGATGGAGATCAG<br>TGTGAGTCCAATCCATGTTTAAATGGCGGCAGTTGCAAGGATGACATT<br>AATTCCTATGAATGTTGGTGTCCCTTTGGATTTGAAGGAAAGAACTGT<br>GAATTAGATGTAACATGTAACATTAAGAATGGCAGATGCGAGCAGTTT<br>TGTAAAAATAGTGCTGATAACAAGGTGGTTTGCTCCTGTACTGAGGGA<br>TATCGACTTGCAGAAAACCAGAAGTCCTGTGAACCAGCAGTGCCATTT<br>CCATGTGGAAGAGTTTCTGTTTCACAAACTTCTAAGCTCACCCGTGCT<br>GAGGCTGTTTTTCCTGATGTGGACTATGTAAATTCTACTGAAGCTGAA<br>ACCATTTTGGATAACATCACTCAAAGCACCCAATCATTTAATGACTTC<br>ACTCGGGTTGTTGGTGGAGAAGATGCCAAACCAGGTCAATTCCCTTGG<br>CAGGTTGTTTTGAATGGTAAAGTTGATGCATTCTGTGGAGGCTCTATC<br>GTTAATGAAAAATGGATTGTAACTGCTGCCCACTGTGTTGAAACTGGT<br>GTTAAAATTACAGTTGTCGCAGGTGAACATAATATTGAGGAGACAGAA<br>CATACAGAGCAAAAGCGAAATGTGATTCGAATTATTCCTCACCACAAC<br>TACAATGCAGCTATTAATAAGTACAACCATGACATTGCCCTTCTGGAA<br>CTGGACGAACCCTTAGTGCTAAACAGCTACGTTACACCTATTTGCATT<br>GCTGACAAGGAATACACGAACATCTTCCTCAAATTTGGATCTGGCTAT<br>GTAAGTGGCTGGGGAAGAGTCTTCCACAAAGGGAGATCAGCTTTAGTT<br>CTTCAGTACCTTAGAGTTCCACTTGTTGACCGAGCCACATGTCTTCGA<br>TCTACAAAGTTCACCATCTATAACAACATGTTCTGTGCTGGCTTCCAT<br>GAAGGAGGTAGAGATTCATGTCAAGGAGATAGTGGGGGACCCCATGTT<br>ACTGAAGTGGAAGGGACCAGTTTCTTAACTGGAATTATTAGCTGGGGT<br>GAAGAGTGTGCAATGAAAGGCAAATATGGAATATATACCAAGGTATCC<br>CGGTATGTCAACTGGATTAAGGAAAAAACAAAGCTCACTTAA |
| 10 | Mut C capsid polypeptide sequence | MAADGYLPDWLEDNLSEGIREWWALKPGAPKPKANQQKQDDGRGLVLP<br>GYKYLGPFNGLDKGEPVNAADAAALEHDKAYDQQLQAGDNPYLRYNHA<br>DAEFQERLQEDTSFGGNLGRAVFQAKKRVLEPLGLVEEGAKTAPGKKR<br>PVDQSPQEPDSSSGVGKSGKQPARKRLNFGQTGDSESVPDPQPLGEPP<br>AAPTSLGSNTMASGGGAPMADNNEGADGVGNSSGNWHCDSQWLGDRVI<br>TTSTRTWALPTYNNHLYKQISSQSGASNDNHYFGYSTPWGYFDFNRFH<br>CHFSPRDWQRLINNNWGFRPKKLSFKLFNIQVKEVTQNDGTTTIANNL<br>TSTVQVFTDSEYQLPYVLGSAHQGCLPPFPADVFMVPQYGYLTLNNGS<br>QAVGRSSFYCLEYFPSQMLRTGNNFQFSYTFEDVPFHSSYAHSQSLDR<br>LMNPLIDQYLYYLNRTQGTTSGTTNQSRLLFSQAGPQSMSLQARNWLP<br>GPCYRQQRLSKTANDNNNSNFPWTAASKYHLNGRDSLVNPGPAMASHK<br>DDEEKFFPMHGNLIFGKEGTTASNAELDNVMITDEEEIRTTNPVATEQ<br>YGTVANNLQSSNTAPTTRTVNDQGALPGMVWQDRDVYLQGPIWAKIPH<br>TDGHFHPSPLMGGFGLKHPPPQIMIKNTPVPANPPTTFSPAKFASFIT<br>QYSTGQVSVEIEWELQKENSKRWNPEIQYTSNYNKSVNVDFTVDTNGV<br>YSEPRPIGTRYLTRNL |
| 11 | FIXco coding sequence with TTG GoF codon | ATGCAGAGGGTGAACATGATCATGGCTGAGAGCCCTGGCCTGATCACC<br>ATCTGCCTGCTGGGCTACCTGCTGTCTGCTGAGTGCACTGTGTTCCTG<br>GACCATGAGAATGCCAACAAGATCCTGAACAGGCCCAAGAGATACAAC<br>TCTGGCAAGCTGGAGGAGTTTGTGCAGGGCAACCTGGAGAGAGAATGC<br>ATGGAGGAGAAGTGCAGCTTTGAGGAGGCCAGGGAGGTGTTTGAGAAC<br>ACTGAGAGGACCACTGAGTTCTGGAAGCAGTATGTGGATGGGGACCAG<br>TGTGAGAGCAACCCCTGCCTGAATGGGGGCAGCTGCAAGGATGACATC<br>AACAGCTATGAGTGCTGGTGCCCCTTTGGCTTTGAGGGCAAGAACTGT<br>GAGCTGGATGTGACCTGCAACATCAAGAATGGCAGATGTGAGCAGTTC<br>TGCAAGAACTCTGCTGACAACAAGGTGGTGTGCAGCTGCACTGAGGGC<br>TACAGGCTGGCTGAGAACCAGAAGAGCTGTGAGCCTGCTGTGCCATTC<br>CCATGTGGCAGAGTGTCTGTGAGCCAGACCAGCAAGCTGACCAGGGCT<br>GAGGCTGTGTTCCCTGATGTGGACTATGTGAACAGCACTGAGGCTGAA<br>ACCATCCTGGACAACATCACCCAGAGCACCCAGAGCTTCAATGACTTC<br>ACCAGGGTGGTGGGGGGGGAGGATGCCAAGCCTGGCCAGTTCCCCTGG<br>CAAGTGGTGCTGAATGGCAAGGTGGATGCCTTCTGTGGGGGCAGCATT<br>GTGAATGAGAAGTGGATTGTGACTGCTGCCCACTGTGTGGAGACTGGG<br>GTGAAGATCACTGTGGTGGCTGGGGAGCACAACATTGAGGAGACTGAG<br>CACACTGAGCAGAAGAGGAATGTGATCAGGATCATCCCCCACCACAAC<br>TACAATGCTGCCATCAACAAGTACAACCATGACATTGCCCTGCTGGAG<br>CTGGATGAGCCCCTGGTGCTGAACAGCTATGTGACCCCCATCTGCATT<br>GCTGACAAGGAGTACACCAACATCTTCCTGAAGTTTGGCTCTGGCTAT<br>GTGTCTGGCTGGGGCAGGGTGTTCCACAAGGGCAGGTCTGCCCTGGTG<br>CTGCAGTACCTGAGGGTGCCCCTGGTGGACAGGGCCACCTGCCTGTTG<br>AGCACCAAGTTCACCATCTACAACAACATGTTCTGTGCTGGCTTCCAT<br>GAGGGGGGCAGGGACAGCTGCCAGGGGGACTCTGGGGGCCCCCATGTG |

TABLE 3-continued

| Sequence identity number | Sequence description | Nucleotide or Amino Acid Sequence |
|---|---|---|
| | | ACTGAGGTGGAGGGCACCAGCTTCCTGACTGGCATCATCAGCTGGGGG GAGGAGTGTGCCATGAAGGGCAAGTATGGCATCTACACCAAAGTCTCC AGATATGTGAACTGGATCAAGGAGAAGACCAAGCTGACCTGA |
| 12 | FIXco coding sequence | ATGCAGAGGGTGAACATGATCATGGCTGAGAGCCCTGGCCTGATCACC ATCTGCCTGCTGGGCTACCTGCTGTCTGCTGAGTGCACTGTGTTCCTG GACCATGAGAATGCCAACAAGATCCTGAACAGGCCCAAGAGATACAAC TCTGGCAAGCTGGAGGAGTTTGTGCAGGGCAACCTGGAGAGGGAGTGC ATGGAGGAGAAGTGCAGCTTTGAGGAGGCCAGGGAGGTGTTTGAGAAC ACTGAGAGGACCACTGAGTTCTGGAAGCAGTATGTGGATGGGGACCAG TGTGAGAGCAACCCCTGCCTGAATGGGGGCAGCTGCAAGGATGACATC AACAGCTATGAGTGCTGGTGCCCCTTTGGCTTTGAGGGCAAGAACTGT GAGCTGGATGTGACCTGCAACATCAAGAATGGCAGATGTGAGCAGTTC TGCAAGAACTCTGCTGACAACAAGGTGGTGTGCAGCTGCACTGAGGGC TACAGGCTGGCTGAGAACCAGAAGAGCTGTGAGCCTGCTGTGCCATTC CCATGTGGCAGAGTGTCTGTGAGCCAGACCAGCAAGCTGACCAGGGCT GAGGCTGTGTTCCCTGATGTGGACTATGTGAACAGCACTGAGGCTGAA ACCATCCTGGACAACATCACCCAGAGCACCCAGAGCTTCAATGACTTC ACCAGGGTGGTGGGGGGGGAGGATGCCAAGCCTGGCCAGTTCCCCTGG CAAGTGGTGCTGAATGGCAAGGTGGATGCCTTCTGTGGGGGCAGCATT GTGAATGAGAAGTGGATTGTGACTGCTGCCCACTGTGTGGAGACTGGG GTGAAGATCACTGTGGTGGCTGGGGAGCACAACATTGAGGAGACTGAG CACACTGAGCAGAAGAGGAATGTGATCAGGATCATCCCCCACCACAAC TACAATGCTGCCATCAACAAGTACAACCATGACATTGCCCTGCTGGAG CTGGATGAGCCCCTGGTGCTGAACAGCTATGTGACCCCCATCTGCATT GCTGACAAGGAGTACACCAACATCTTCCTGAAGTTTGGCTCTGGCTAT GTGTCTGGCTGGGGCAGGGTGTTCCACAAGGGCAGGTCTGCCCTGGTG CTGCAGTACCTGAGGGTGCCCCTGGTGGACAGGGCCACCTGCCTGAGG AGCACCAAGTTCACCATCTACAACAACATGTTCTGTGCTGGCTTCCAT GAGGGGGGCAGGGACAGCTGCCAGGGGGACTCTGGGGGCCCCCATGTG ACTGAGGTGGAGGGCACCAGCTTCCTGACTGGCATCATCAGCTGGGGG GAGGAGTGTGCCATGAAGGGCAAGTATGGCATCTACACCAAAGTCTCC AGATATGTGAACTGGATCAAGGAGAAGACCAAGCTGACCTGA |
| 13 | Enhancer element from HLP2 | CCCTAAAATGGGCAAACATTGCAAGCAGCAAACAGCAAACACACAGCC CTCCCTGCCTGCTGACCTTGGAGCTGGGGCAGAGGTCAGACACCTCTC TGGGCCCATGCCACCTCCAAC |
| 14 | Promoter element from HLP2 | GGGCGACTCAGATCCCAGCCAGTGGACTTAGCCCCTGTTTGCTCCTCC GATAACTGGGGTGACCTTGGTTAATATTCACCAGCAGCCTCCCCCGTT GCCCCTCTGGATCCACTGCTTAAATACGGACGAGGACAGGGCCCTGTC TCCTCAGCTTCAGGCACCACCACTGACCTGGGACAGTGAAT |
| 15 | Wild type portion of TI-ACNP-FIX-GoF coding sequence, excluding the intron | ATGCAGCGCGTGAACATGATCATGGCAGAATCACCAGGCCTCATCACC ATCTGCCTTTTAGGATATCTACTCAGTGCTGAATGTACAGTTTTCTT GATCATGAAAACGCCAACAAATTTCTGAATCGGCCAAAGAGGTATAAT TCAGGTAAATTGGAAGAGTTTGTTCAAGGGAACCTTGAGAGAGAATGT ATG |
| 16 | "Immature" Factor IX amino acid sequence encoded by SEQ ID NO. 4 | MQRVNMIMAESPGLITICLLGYLLSAECTVFLDHENANKILNRPKRYN SGKLEEFVQGNLERECMEEKCSFEEAREVFENTERTTEFWKQYVDGDQ CESNPCLNGGSCKDDINSYECWCPFGFEGKNCELDVTCNIKNGRCEQF CKNSADNKVVCSCTEGYRLAENQKSCEPAVPFPCGRVSVSQTSKLTRA EAVFPDVDYVNSTEAETILDNITQSTQSFNDFTRVVGGEDAKPGQFPW QVVLNGKVDAFCGGSIVNEKWIVTAAHCVETGVKITVVAGEHNIEETE HTEQKRNVIRIIPHHNYNAAINKYNHDIALLELDEPLVLNSYVTPICI ADKEYTNIFLKFGSGYVSGWGRVFHKGRSALVLQYLRVPLVDRATCLL STKFTIYNNMECAGFHEGGRDSCQGDSGGPHVTEVEGTSFLTGIISWG EECAMKGKYGIYTKVSRYVNWIKEKTKLT |
| 17 | AAV5 capsid polypeptide sequence | MSFVDHPPDWLEEVGEGLREFLGLEAGPPKPKPNQQHQDQARGLVLPG YNYLGPGNGLDRGEPVNRADEVAREHDISYNEQLEAGDNPYLKYNHAD AEFQEKLADDTSFGGNLGKAVFQAKKRVLEPFGLVEEGAKTAPTGKRI DDHFPKRKKARTEEDSKPSTSSDAEAGPSGSQQLQIPAQPASSLGADT MSAGGGGPLGDNNQGADGVGNASGDWHCDSTWMGDRVVTKSTRTWVLP SYNNHQYREIKSGSVDGSNANAYFGYSTPWGYFDFNRFHSHWSPRDWQ RLINNYWGFRPRSLRVKIFNIQVKEVTVQDSTTTIANNLTSTVQVFTD DDYQLPYVVGNGTEGCLPAFPPQVFTLPQYGYATLNRDNTENPTERSS FFCLEYFPSKMLRTGNNFEFTYNFEEVPFHSSFAPSQNLFKLANPLVD QYLYRFVSTNNTGGVQFNKNLAGRYANTYKNWFPGPMGRTQGWNLGSG VNRASVSAFATTNRMELEGASYQVPPQPNGMTNNLQGSNTYALENTMI FNSQPANPGTTATYLEGNMLITSESETQPVNRVAYNVGGQMATNNQSS TTAPATGTYNLQEIVPGSVWMERDVYLQGPIWAKIPETGAHFHPSPAM GGFGLKHPPPMMLIKNTPVPGNITSFSDVPVSSFITQYSTGQVTVEME |

TABLE 3-continued

| Sequence identity number | Sequence description | Nucleotide or Amino Acid Sequence |
|---|---|---|
| | | WELKKENSKRWNPEIQYTNNYNDPQFVDFAPDSTGEYRTTRPIGTRYL<br>TRPL |
| 18 | Coding sequence of TI-codop-FIX GoF Factor IX sequence, including intron | ATGCAGCGCGTGAACATGATCATGGCAGAATCACCAGGCCTCATCACC<br>ATCTGCCTTTTAGGATATCTACTCAGTGCTGAATGTACAGGTTTGTTT<br>CCTTTTTTAAAATACATTGAGTATGCTTGCCTTTTAGATATAGAAATA<br>TCTGATGCTGTCTTCTTCACTAAATTTTGATTACATGATTTGACAGCA<br>ATATTGAAGAGTCTAACAGCCAGCACGCAGGTTGGTAAGTACTGTGGG<br>AACATCACAGATTTTGGCTCCATGCCCTAAAGAGAAATTGGCTTTCAG<br>ATTATTTGGATTAAAAACAAAGACTTTCTTAAGAGATGTAAAATTTTC<br>ATGATGTTTTCTTTTTTGCTAAAACTAAAGAATTATTCTTTTACATTT<br>CAGTTTTTCTTGATCATGAAAACGCCAACAAAATTCTGAATCGGCCAA<br>AGAGGTATAATTCAGGTAAATTGGAAGAGTTTGTTCAAGGGAACCTTG<br>AGAGAGAATGTATGGAGGAGAAGTGTTCTTTCGAGGAGGCGAGAGAGG<br>TTTTCGAGAATACTGAGCGAACAACCGAATTCTGGAAACAATATGTGG<br>ATGGCGACCAATGTGAATCTAATCCCTGCCTCAACGGTGGCTCATGCA<br>AAGACGATATCAACAGCTACGAGTGTTGGTGCCCCTTTGGTTTCGAGG<br>GAAAGAATTGCGAGCTTGATGTAACCTGTAACATTAAGAATGGGCGCT<br>GCGAACAGTTTTGCAAGAACAGCGCCGACAATAAGGTCGTCTGCAGTT<br>GTACCGAAGGCTATAGGCTTGCAGAGAATCAGAAGAGTTGCGAGCCTG<br>CTGTGCCGTTCCCATGTGGCAGAGTCAGTGTGTCCCAAACTAGCAAGC<br>TGACAAGAGCAGAAGCCGTTTTCCCCGATGTGGACTACGTGAATTCCA<br>CTGAAGCCGAAACGATCCTGGACAATATCACACAGAGCACTCAGTCTT<br>TCAACGACTTCACACGGGTTGTGGGAGGAGAGGACGCCAAACCCGGCC<br>AGTTTCCTTGGCAAGTCGTTCTTAACGGCAAGGTCGACGCCTTTTGTG<br>GAGGGAGTATTGTGAACGAGAAATGGATTGTCACCGCTGCTCATTGTG<br>TTGAAACTGGGGTGAAAATCACTGTTGTCGCAGGAGAGCACAATATCG<br>AAGAGACAGAACACACCGAGCAGAAACGCAACGTTATTCGGATCATTC<br>CACATCACAACTACAATGCTGCCATCAACAAGTACAACCACGACATTG<br>CGCTGCTGGAGTTGGATGAACCTCTCGTGCTCAACTCCTATGTGACCC<br>CAATCTGCATAGCAGATAAGGAGTATACCAACATCTTCCTGAAGTTTG<br>GGTCAGGTTATGTGTCAGGCTGGGGACGAGTGTTTCATAAAGGGAGAT<br>CAGCACTGGTGTTGCAGTATCTGCGCGTACCACTGGTGGATCGGGCTA<br>CTTGCCTGCTAAGCACAAAATTCACCATCTACAACAACATGTTTTGTG<br>CCGGTTTTCACGAAGGCGGCAGGGACAGCTGTCAGGGAGATTCCGGAG<br>GGCCTCATGTCACAGAGGTCGAGGGCACCTCCTTTCTCACTGGGATTA<br>TAAGCTGGGGAGAAGAATGCGCCATGAAAGGGAAGTACGGCATATACA<br>CGAAAGTGTCTAGATACGTGAATTGGATTAAGGAAAAGACCAAACTGA<br>CGTGA |
| 19 | Wild type Factor IX (Malmo B variant) coding sequence corresponding to mature FIX polypeptide | TATAATTCAGGTAAATTGGAAGAGTTTGTTCAAGGGAACCTTGAGAGA<br>GAATGTATGGAAGAAAAGTGTAGTTTTGAAGAAGCACGAGAGTTTTT<br>GAAAACACTGAAAGAACAACTGAATTTTGGAAGCAGTATGTTGATGGA<br>GATCAGTGTGAGTCCAATCCATGTTTAAATGGCGGCAGTTGCAAGGAT<br>GACATTAATTCCTATGAATGTTGGTGTCCCTTTGGATTTGAAGGAAAG<br>AACTGTGAATTAGATGTAACATGTAACATTAAGAATGGCAGATGCGAG<br>CAGTTTTGTAAAAATAGTGCTGATAACAAGGTGGTTTGCTCCTGTACT<br>GAGGGATATCGACTTGCAGAAAACCAGAAGTCCTGTGAACCAGCAGTG<br>CCATTTCCATGTGGAAGAGTTTCTGTTTCACAAACTTCTAAGCTCACC<br>CGTGCTGAGGCTGTTTTTCCTGATGTGGACTATGTAAATTCTACTGAA<br>GCTGAAACCATTTTGGATAACATCACTCAAAGCACCCAATCATTTAAT<br>GACTTCACTCGGGTTGTTGGTGGAGAAGATGCCAAACCAGGTCAATTC<br>CCTTGGCAGGTTGTTTTGAATGGTAAAGTTGATGCATTCTGTGGAGGC<br>TCTATCGTTAATGAAAAATGGATTGTAACTGCTGCCCACTGTGTTGAA<br>ACTGGTGTTAAAATTACAGTTGTCGCAGGTGAACATAATATTGAGGAG<br>ACAGAACATACAGAGCAAAAGCGAAATGTGATTCGAATTATTCCTCAC<br>CACAACTACAATGCAGCTATTAATAAGTACAACCATGACATTGCCCTT<br>CTGGAACTGGACGAACCCTTAGTGCTAAACAGCTACGTTACACCTATT<br>TGCATTGCTGACAAGGAATACACGAACATCTTCCTCAAATTTGGATCT<br>GGCTATGTAAGTGGCTGGGGAAGAGTCTTCCACAAAGGGAGATCAGCT<br>TTAGTTCTTCAGTACCTTAGAGTTCCACTTGTTGACCGAGCCACATGT<br>CTTCGATCTACAAAGTTCACCATCTATAACAACATGTTCTGTGCTGGC<br>TTCCATGAAGGAGGTAGAGATTCATGTCAAGGAGATAGTGGGGGACCC<br>CATGTTACTGAAGTGGAAGGGACCAGTTTCTTAACTGGAATTATTAGC<br>TGGGGTGAAGAGTGTGCAATGAAAGGCAAATATGGAATATATACCAAG<br>GTATCCCGGTATGTCAACTGGATTAAGGAAAAAACAAAGCTCACTTAA |
| 20 | AAV2-5 hybrid VP1u variant 1 | MAADGYLPDWLEEVGEGLREFLGLEAGPPKPKPNQQHQDQARGLVLPG<br>YNYLGPGNGLDRGEPVNRADEVAREHDISYNEQLEAGDNPYLKYNHAD<br>AEFQEKLADDTSFGGNLGKAVFQAKKRVLEPFGVEEGAKTAPTGKRI<br>DDHFPKRKKARTEEDSKPSTSSDAEAGPSGSQQLQIPAQPASSLGADT<br>MSAGGGGPLGDNNQGADGVGNASGDWHCDSTWMGDRVVTKSTRTWVLP<br>SYNNHQYREIKSGSVDGSNANAYFGYSTPWGYFDFNRFHSHWSPRDWQ<br>RLINNYWGFRPRSLRVKIFNIQVKEVTVQDSTTTTANNLTSTVQVFTD<br>DDYQLPYVVGNGTEGCLPAFPPQVFTLPQYGYATLNRDNTENPTERSS<br>FFCLEYFPSKMLRTGNNFEFTYNFEEVPFHSSFAPSQNLFKLANPLVD |

TABLE 3-continued

| Sequence identity number | Sequence description | Nucleotide or Amino Acid Sequence |
|---|---|---|
| | | QYLYRFVSTNNTGGVQFNKNLAGRYANTYKNWFPGPMGRTQGWNLGSG<br>VNRASVSAFATTNRMELEGASYQVPPQPNGMTNNLQGSNTYALENTMI<br>FNSQPANPGTTATYLEGNMLITSESETQPVNRVAYNVGGQMATNNQSS<br>TTAPATGTYNLQEIVPGSVWMERDVYLQGPIWAKIPETGAHFHPSPAM<br>GGFGLKHPPPMMLIKNTPVPGNITSFSDVPVSSFITQYSTGQVTVEME<br>WELKKENSKRWNPEIQYTNNYNDPQFVDFAPDSTGEYRTTRPIGTRYL<br>TRPL |
| 21 | AAV2-5 hybrid VP1u variant 2 | MAADGYLPDWLEDTLSEGIRQWWKLKPGPPPPKPAERHKDDSRGLVLP<br>GYNYLGPGNGLDRGEPVNRADEVAREHDISYNEQLEAGDNPYLKYNHA<br>DAEFQEKLADDTSFGGNLGKAVFQAKKRVLEPFGLVEEGAKTAPTGKR<br>IDDHFPKRKKARTEEDSKPSTSSDAEAGPSGSQQLQIPAQPASSLGAD<br>TMSAGGGGPLGDNNQGADGVGNASGDWHCDSTWMGDRVVTKSTRTWVL<br>PSYNNHQYREIKSGSVDGSNANAYEGYSTPWGYFDFNRFHSHWSPRDW<br>QRLINNYWGFRPRSLRVKIFNIQVKEVTVQDSTTTIANNLTSTVQVFT<br>DDDYQLPYVVGNGTEGCLPAFPPQVFTLPQYGYATLNRDNTENPTERS<br>SFFCLEYFPSKMLRTGNNFEFTYNFEEVPFHSSFAPSQNLFKLANPLV<br>DQYLYRFVSTNNTGGVQFNKNLAGRYANTYKNWFPGPMGRTQGWNLGS<br>GVNRASVSAFATTNRMELEGASYQVPPQPNGMTNNLQGSNTYALENTM<br>IFNSQPANPGTTATYLEGNMLITSESETQPVNRVAYNVGGQMATNNQS<br>STTAPATGTYNLQEIVPGSVWMERDVYLQGPIWAKIPETGAHFHPSPA<br>MGGFGLKHPPPMMLIKNTPVPGNITSFSDVPVSSFITQYSTGQVTVEM<br>EWELKKENSKRWNPEIQYTNNYNDPQFVDFAPDSTGEYRTTRPIGTRY<br>LTRPL |
| 22 | AAV2-5 hybrid VP1u variant 3 | MAADGYLPDWLEDTLSEGIRQWWKLKPGPPPPKPAERHKDDSRGLVLP<br>GYKYLGPFNGLDKGEPVNRADEVAREHDISYNEQLEAGDNPYLKYNHA<br>DAEFQEKLADDTSFGGNLGKAVFQAKKRVLEPFGLVEEGAKTAPTGKR<br>IDDHFPKRKKARTEEDSKPSTSSDAEAGPSGSQQLQIPAQPASSLGAD<br>TMSAGGGGPLGDNNQGADGVGNASGDWHCDSTWMGDRVVTKSTRTWVL<br>PSYNNHQYREIKSGSVDGSNANAYFGYSTPWGYFDFNRFHSHWSPRDW<br>QRLINNYWGFRPRSLRVKIFNIQVKEVTVQDSTTTIANNLTSTVQVFT<br>DDDYQLPYVVGNGTEGCLPAFPPQVFTLPQYGYATLNRDNTENPTERS<br>SFFCLEYFPSKMLRTGNNFEFTYNFEEVPFHSSFAPSQNLFKLANPLV<br>DQYLYRFVSTNNTGGVQFNKNLAGRYANTYKNWFPGPMGRTQGWNLGS<br>GVNRASVSAFATTNRMELEGASYQVPPQPNGMTNNLQGSNTYALENTM<br>IFNSQPANPGTTATYLEGNMLITSESETQPVNRVAYNVGGQMATNNQS<br>STTAPATGTYNLQEIVPGSVWMERDVYLQGPIWAKIPETGAHFHPSPA<br>MGGFGLKHPPPMMLIKNTPVPGNITSFSDVPVSSFITQYSTGQVTVEM<br>EWELKKENSKRWNPEIQYTNNYNDPQFVDFAPDSTGEYRTTRPIGTRY<br>LTRPL |
| 23 | AAV2-5 hybrid VP1u variant 4 | MAADGYLPDWLEDTLSEGIRQWWKLKPGPPPPKPAERHKDDSRGLVLP<br>GYKYLGPFNGLDKGEPVNEADAAALEHDKAYDRQLDSGDNPYLKYNHA<br>DAEFQEKLADDTSFGGNLGKAVFQAKKRVLEPFGLVEEGAKTAPTGKR<br>IDDHFPKRKKARTEEDSKPSTSSDAEAGPSGSQQLQIPAQPASSLGAD<br>TMSAGGGGPLGDNNQGADGVGNASGDWHCDSTWMGDRVVTKSTRTWVL<br>PSYNNHQYREIKSGSVDGSNANAYEGYSTPWGYFDFNRFHSHWSPRDW<br>QRLINNYWGFRPRSLRVKIFNIQVKEVTVQDSTTTIANNLTSTVQVFT<br>DDDYQLPYVVGNGTEGCLPAFPPQVFTLPQYGYATLNRDNTENPTERS<br>SFFCLEYFPSKMLRTGNNFEFTYNFEEVPFHSSFAPSQNLFKLANPLV<br>DQYLYRFVSTNNTGGVQFNKNLAGRYANTYKNWFPGPMGRTQGWNLGS<br>GVNRASVSAFATTNRMELEGASYQVPPQPNGMTNNLQGSNTYALENTM<br>IFNSQPANPGTTATYLEGNMLITSESETQPVNRVAYNVGGQMATNNQS<br>STTAPATGTYNLQEIVPGSVWMERDVYLQGPIWAKIPETGAHFHPSPA<br>MGGFGLKHPPPMMLIKNTPVPGNITSFSDVPVSSFITQYSTGQVTVEM<br>EWELKKENSKRWNPEIQYTNNYNDPQFVDFAPDSTGEYRTTRPIGTRY<br>LTRPL |
| 24 | AAV2-5 hybridVP1u variavt 5 | MAADGYLPDWLEDTLSEGIRQWWKLKPGPPPPKPAERHKDDSRGLVLP<br>GYKYLGPFNGLDKGEPVNEADAAALEHDKAYDRQLDSGDNPYLKYNHA<br>DAEFQERLKEDTSFGGNLGRAVFQAKKRVLEPFGLVEEGAKTAPTGKR<br>IDDHFPKRKKARTEEDSKPSTSSDAEAGPSGSQQLQIPAQPASSLGAD<br>TMSAGGGGPLGDNNQGADGVGNASGDWHCDSTWMGDRVVTKSTRTWVL<br>PSYNNHQYREIKSGSVDGSNANAYFGYSTPWGYFDFNRFHSHWSPRDW<br>QRLINNYWGFRPRSLRVKIFNIQVKEVTVQDSTTTIANNLTSTVQVFT<br>DDDYQLPYVVGNGTEGCLPAFPPQVFTLPQYGYATLNRDNTENPTERS<br>SFFCLEYFPSKMLRTGNNFEFTYNFEEVPFHSSFAPSQNLFKLANPLV<br>DQYLYRFVSTNNTGGVQFNKNLAGRYANTYKNWFPGPMGRTQGWNLGS<br>GVNRASVSAFATTNRMELEGASYQVPPQPNGMTNNLQGSNTYALENTM<br>IFNSQPANPGTTATYLEGNMLITSESETQPVNRVAYNVGGQMATNNQS<br>STTAPATGTYNLQEIVPGSVWMERDVYLQGPIWAKIPETGAHFHPSPA<br>MGGFGLKHPPPMMLIKNTPVPGNITSFSDVPVSSFITQYSTGQVTVEM<br>EWELKKENSKRWNPEIQYTNNYNDPQFVDFAPDSTGEYRTTRPIGTRY<br>LTRPL |

TABLE 3-continued

| Sequence identity number | Sequence description | Nucleotide or Amino Acid Sequence |
|---|---|---|
| 25 | AAV2-5 hybrid VP1u variant 6 | MAADGYLPDWLEDTLSEGIRQWWKLKPGPPPPKPAERHKDDSRGLVLP GYKYLGPFNGLDKGEPVNEADAAALEHDKAYDRQLDSGDNPYLKYNHA DAEFQERLKEDTSFGGNLGRAVFQAKKRVLEPLGLVEEPVKTAPTGKR IDDHFPKRKKARTEEDSKPSTSSDAEAGPSGSQQLQIPAQPASSLGAD TMSAGGGGPLGDNNQGADGVGNASGDWHCDSTWMGDRVVTKSTRTWVL PSYNNHQYREIKSGSVDGSNANAYFGYSTPWGYFDFNRFHSHWSPRDW QRLINNYWGFRPRSLRVKIFNIQVKEVTVQDSTTTIANNLTSTVQVFT DDDYQLPYVVGNGTEGCLPAFPPQVFTLPQYGYATLNRDNTENPTERS SFFCLEYFPSKMLRTGNNFEFTYNFEEVPFHSSFAPSQNLFKLANPLV DQYLYRFVSTNNTGGVQFNKNLAGRYANTYKNWFPGPMGRTQGWNLGS GVNRASVSAFATTNRMELEGASYQVPPQPNGMTNNLQGSNTYALENTM IFNSQPANPGTTATYLEGNMLITSESETQPVNRVAYNVGGQMATNNQS STTAPATGTYNLQEIVPGSVWMERDVYLQGPIWAKIPETGAHFHPSPA MGGFGLKHPPPMMLIKNTPVPGNITSFSDVPVSSFITQYSTGQVTVEM EWELKKENSKRWNPEIQYTNNYNDPQFVDFAPDSTGEYRTTRPIGTRY LTRPL |
| 26 | FIXco coding sequence with CTG GoF codon | ATGCAGAGGGTGAACATGATCATGGCTGAGAGCCCTGGCCTGATCACC ATCTGCCTGCTGGGCTACCTGCTGTCTGCTGAGTGCACTGTGTTCCTG GACCATGAGAATGCCAACAAGATCCTGAACAGGCCCAAGAGATACAAC TCTGGCAAGCTGGAGGAGTTTGTGCAGGGCAACCTGGAGAGGGAGTGC ATGGAGGAGAAGTGCAGCTTTGAGGAGGCCAGGGAGGTGTTTGAGAAC ACTGAGAGGACCACTGAGTTCTGGAAGCAGTATGTGGATGGGGACCAG TGTGAGAGCAACCCCTGCCTGAATGGGGGCAGCTGCAAGGATGACATC AACAGCTATGAGTGCTGGTGCCCCTTTGGCTTTGAGGGCAAGAACTGT GAGCTGGATGTGACCTGCAACATCAAGAATGGCAGATGTGAGCAGTTC TGCAAGAACTCTGCTGACAACAAGGTGGTGCAGCTGCACTGAGGGC TACAGGCTGGCTGAGAACCAGAAGAGCTGTGAGCCTGCTGTGCCATTC CCATGTGGCAGAGTGTCTGTGAGCCAGACCAGCAAGCTGACCAGGGCT GAGGCTGTGTTCCCTGATGTGGACTATGTGAACAGCACTGAGGCTGAA ACCATCCTGGACAACATCACCCAGAGCACCCAGAGCTTCAATGACTTC ACCAGGGTGGTGGGGGGGAGGATGCCAAGCCTGGCCAGTTCCCCTGG CAAGTGGTGCTGAATGGCAAGGTGGATGCCTTCTGTGGGGGCAGCATT GTGAATGAGAAGTGGATTGTGACTGCTGCCCACTGTGTGGAGACTGGG GTGAAGATCACTGTGGTGGCTGGGGAGCACAACATTGAGGAGACTGAG CACACTGAGCAGAAGAGGAATGTGATCAGGATCATCCCCCACCACAAC TACAATGCTGCCATCAACAAGTACAACCATGACATTGCCCTGCTGGAG CTGGATGAGCCCCTGGTGCTGAACAGCTATGTGACCCCCATCTGCATT GCTGACAAGGAGTACACCAACATCTTCCTGAAGTTTGGCTCTGGCTAT GTGTCTGGCTGGGCAGGGTGTTCCACAAGGGCAGGTCTGCCCTGGTG CTGCAGTACCTGAGGGTGCCCCTGGTGGACAGGGCCACCTGCCTGCTG AGCACCAAGTTCACCATCTACAACAACATGTTCTGTGCTGGCTTCCAT GAGGGGGGCAGGGACAGCTGCCAGGGGGACTCTGGGGGCCCCCATGTG ACTGAGGTGGAGGGCACCAGCTTCCTGACTGGCATCATCAGCTGGGGG GAGGAGTGTGCCATGAAGGGCAAGTATGGCATCTACACCAAAGTCTCC AGATATGTGAACTGGATCAAGGAGAAGACCAAGCTGACCTGA |

EXAMPLES

In the following examples, experiments were performed with recombinant AAV carrying the FIX transgene cassettes ssLP1.FIXco (FIXco herein), ssHLP2.TI-codop-FIX-GoF (HTFG herein) and ssHLP2.TI-ACNP-FIX-GoF (HTAG herein). SsHLP2.TI-codop-FIX-GoF is a version of the ssHLP2.TI-codop-FIX construct disclosed in WO2016/075473 modified to encode leucine (L) instead of arginine (R) at position 384 of the encoded FIX polypeptide. These cassettes are shown in FIG. 1A, FIG. 1B, and FIG. 1C. ssLP1.FIXco contains a fully codon-optimised FIX coding sequence (SEQ ID NO: 12) preceded 5' by an SV40 intron, with expression driven by the LP1 promoter (SEQ ID NO: 7). ssHLP2.TI-codop-FIX-GoF and ssHLP2.TI-ACNP-FIX-GoF share the structure of having the shorter HLP2 transcription regulatory element (SEQ ID NO: 6) 5' to a FIX coding sequence which is interrupted by a truncated version of the native intron 1A and in which the exon 1 and part of the exon 2 nucleotide sequence is wild type (non-codon-optimised), with the remainder of the coding sequence codon-optimised (SEQ ID NO: 18 for HTFG and SEQ ID NO: 5 for HTAG). The nucleotide sequence of the codon-optimised portions is what differs between the respective two constructs. Unlike the wild type FIX protein encoded by ssLP1.FIXco, ssHLP2.TI-codop-FIX-GoF and ssHLP2.TI-ACNP-FIX-GoF encode a hyper-active FIX having an arginine (R) to leucine (L) substitution at position 384 of the FIX polypeptide.

Example 1—Methods

AAV Vector Production and Quantification

1. AAV vector stocks were prepared by standard triple plasmid transfection of human embryonic kidney (HEK293) cells with a combination of plasmids consisting of a vector genome plasmid, an adenoviral helper plasmid, and a packaging plasmid containing AAV Rep and Cap (AAV8 or AAVMut C) functions. As the recombinant AAV particles contained a genome based on AAV2, and a capsid from serotype 8 or a synthetic capsid comprising portions from two serotypes (Mut C'; SEQ ID NO: 10), they are referred to as 'pseudotyped'.

2. Vectors were purified by density gradient centrifugation with iodixanol.

3. Vector genomes were titred by qPCR with primers directed to the promoter region. In vitro transduction and detection of FIX expression 1. HUH7 cells were plated at $5\times10^5$ cells per well in 12-well plates.
2. Cells were then stimulated with mitomycin C for 1 hour before transduction with AAV particles carrying a FIX-encoding transgene cassette.
3. Five days after transduction, supernatant was collected and analysed for the level of FIX using a commercially available ELISA kit (Stago Asserachrom IX:Ag kit Ref #00943). Activity of FIX was analysed using the commercially available chromogenic kit from Quadratech (Biophen FIX (6) kit Ref #221806).
4. Vector genome DNA was extracted using the Qiagen DNeasy Blood and Tissue kit (Ref #69506) according to the manufacturer's instructions, and quantified by qPCR.

Detection of FIX In Vivo

1. Adult C57BL/6 mice were injected with $5\times10^{10}$ vector genomes (vg) of AAV particles carrying a FIX-encoding transgene cassette via the tail vein (n=4 per group).
2. Two weeks after injection mice were anaesthetised and blood collected via cardiac puncture, added to sodium citrate (1/10 dilution), and centrifuged at 3000×g for 15 minutes at 4° C. to collect the plasma, which was frozen at −80° C. for analysis.
3. Liver was harvested and snap frozen in liquid nitrogen before storage at −80° C. for DNA extraction (Qiagen DNeasy Blood and Tissue kit, Ref #69506) for vector genome analysis.
4. The level of FIX present in murine plasma was determined using a FIX ELISA kit (Stago Asserachrom IX:Ag kit REF 00943). The activity of human FIX was determined using the commercially available chromogenic kit from Quadratech (Biophen FIX (6) kit Ref #221806).

Example 2—Analysis of In Vitro FIX Trans Gene Expression Using ELISA

HUH7 (human hepatocyte) cells were cultured in standard cell culture conditions. FIX transgenes were expressed by treating HUH7 cells with mitomycin C for 1 hour then subsequently transducing with pseudotyped ssAAV2/Mut C. AAV particles were first generated by transfection of HEK293 cells with recombinant vector genome plasmid, in addition to AAV helper and packaging plasmids, and culturing for a further 48 hours. ssAAV2/Mut C vectors were purified from the HEK293 cells by density gradient centrifugation and iodixanol. Vector genomes were titred by qPCR utilizing primers directed towards the promoter region of the transgene expression cassette. FIX expression cassettes were compared to determine their relative ability to express a FIX transgene in vitro by measuring FIX levels 5 days post-transduction. Vectors being evaluated were ssAAV2/Mut C.HLP2.TI-codop-FIX-GoF and ssAAV2/Mut C.HLP2.TI-ACNP-FIX-GoF. FIX levels in the culture supernatant were analysed through the use of a commercially available ELISA kit (Stago Asserachrom IX:Ag kit Ref #00943). In two separate experiments (see FIG. 2D, FIG. 2E, and FIG. 2F and FIG. 4D and FIG. 4E) FIX expression levels—as derived from ELISA assays utilizing the supernatant of HUH7 cultured cells—were normalised against copies of the vector genome per cell following the harvesting of HUH7 cell DNA using the Qiagen DNeasy Blood and Tissue kit (Ref #69506).

Figure 5:
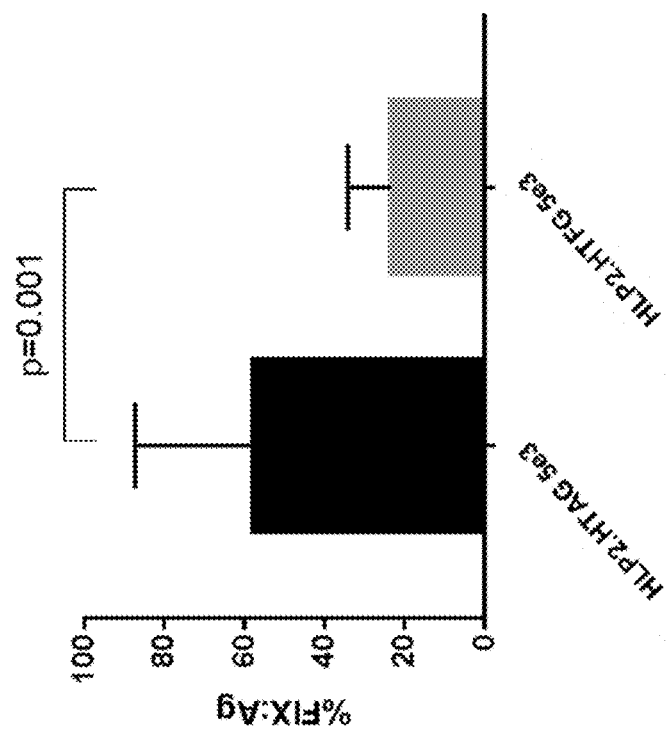
FIG. 5—Combined data (from Experiments 1 and 2) for AAV2/Mut C transduction of HUH7 cells at MOI $5\times10^3$. Error bars represent mean±SD of n=12. P=0.001 by Student's T-test. $5e3=5\times10^3$; MOI=multiplicity of infection.
Figure 6:
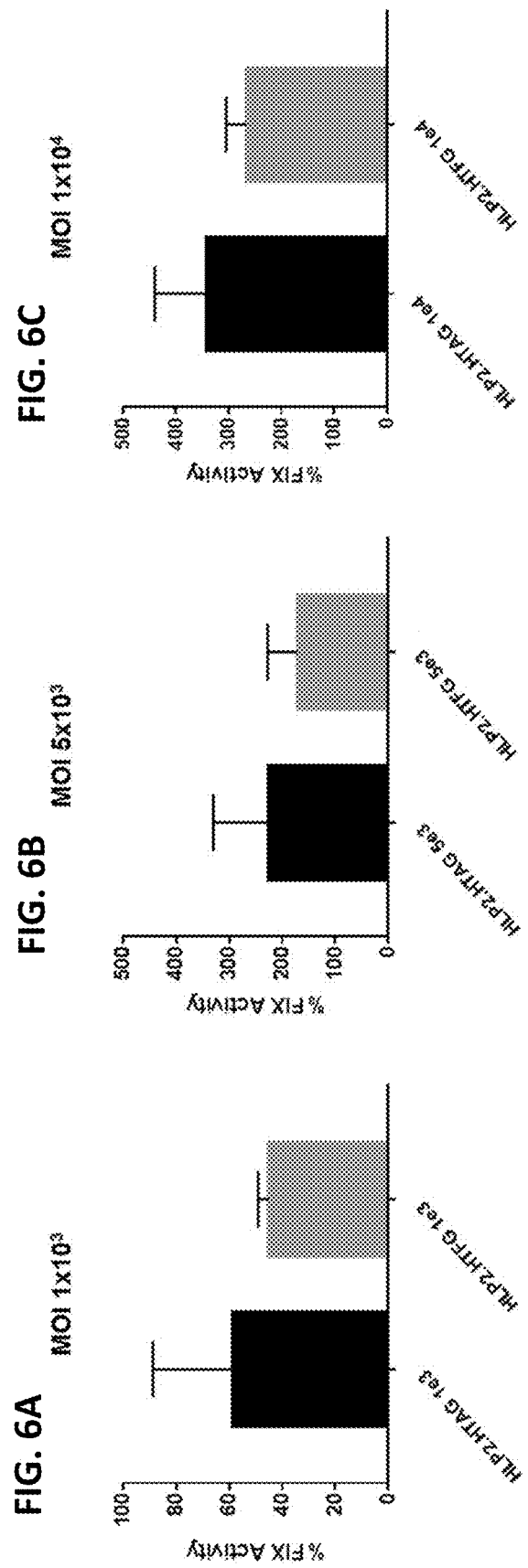
FIG. 6A, FIG. 6B, and FIG. 6C—The activity of FIX for MOI $1\times10^3$, $5\times10^3$ and $1\times10^4$ is shown after HUH7 transduction with AAV2/Mut C vectors (Experiment 1). Error bars represent mean±SD of n=2 duplicate wells. $1e3=1\times10^3$; $5e3=5\times10^3$; $1e4=1\times10^4$; MOI=multiplicity of infection.
Figure 7:
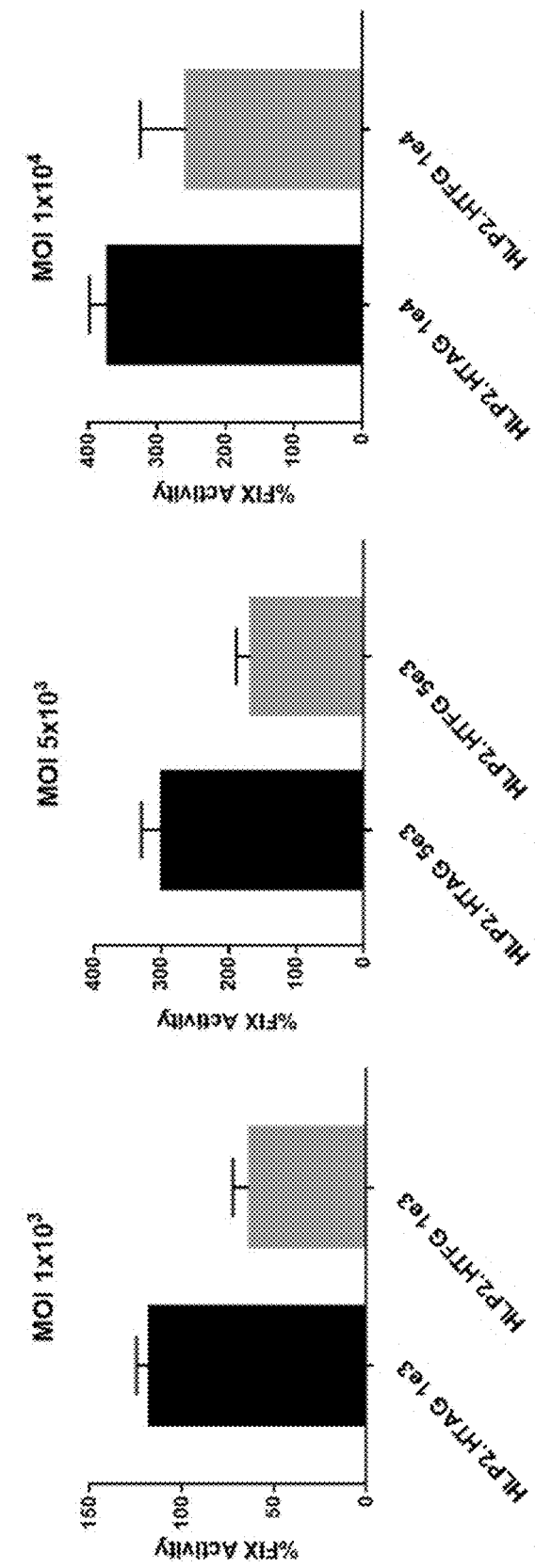
FIG. 7A, FIG. 7B, and FIG. 7C—The activity of FIX is shown after HUH7 transduction with AAV2/Mut C vectors (Experiment 2). Error bars represent mean±SD of n=3. $1e3=1\times10^3$; $5e3=5\times10^3$; $1e4=1\times10^4$, MOI=multiplicity of infection.
Figure 8:
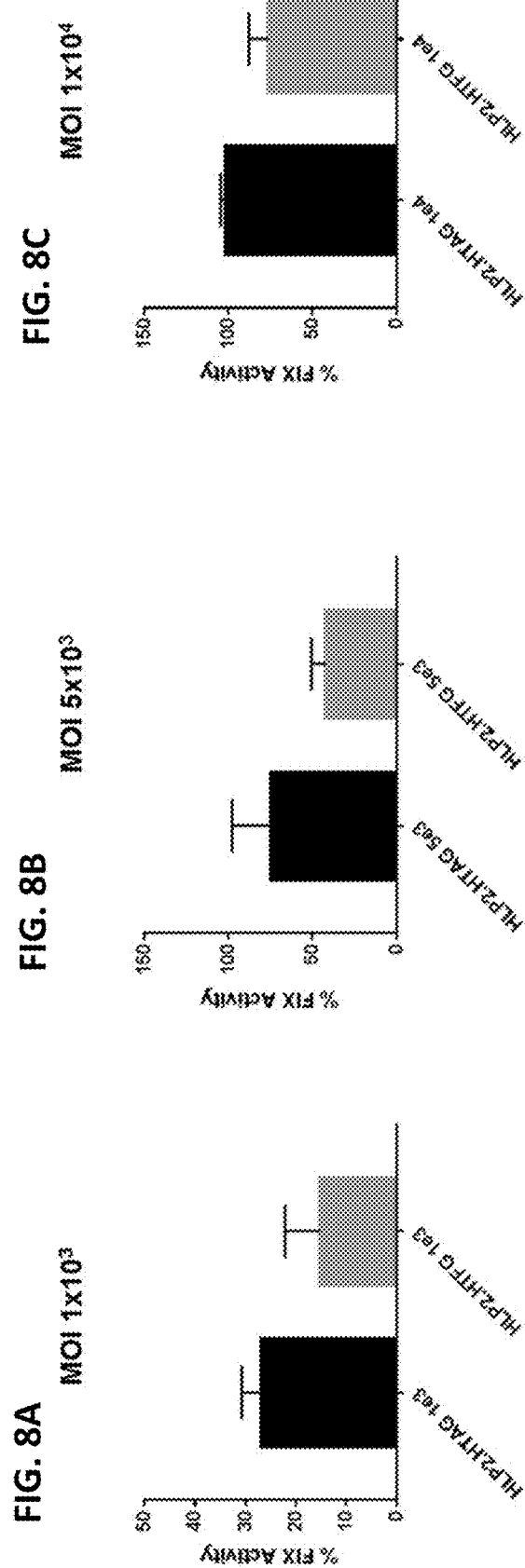
FIG. 8A, FIG. 8B, and FIG. 8C—The activity of FIX is shown after HUH7 transduction with AAV2/Mut C vectors (Experiment 2). Error bars represent mean±SD of n=3. $1e3=1\times10^3$; $5e3=5\times10^3$; $1e4=1\times10^4$, MOI=multiplicity of infection.

5 days post-transduction with ssAAV2/Mut C.HLP2.TI-codop-FIX-GoF and ssAAV2/Mut C.HLP2.TI-ACNP-FIX-GoF at a MOI of $1\times10^3$ vector genomes (vg), FIX levels were greater in HUH7 cells transduced with ssAAV2/Mut C.HLP2.TI-ACNP-FIX-GoF than in HUH7 cells transduced with ssAAV2/Mut C.HLP2.TI-codop-FIX-GoF (n=2; FIG. 2A, FIG. 2B, and FIG. 2C, FIG. 3A, FIG. 3B, and FIG. 3C, and FIG. 4A, FIG. 4B, and FIG. 4C). Similarly, when identical FIX expression assays were performed in HUH7 cells with increased MOI ($5\times10^3$ and $1\times10^4$), FIX levels were greater in cells transduced with ssAAV2/Mut C.HLP2.TI-ACNP-FIX-GoF than in cells transduced with ssAAV2/Mut C.HLP2.TI-codop-FIX-GoF (n=2; FIG. 2A, FIG. 2B, FIG. 2C, FIG. 3A, FIG. 3B, FIG. 3C and FIG. 4A, FIG. 4B, and FIG. 4C). When FIX expression levels were normalised against viral vector genome copies per cell, at each of the three MOIs tested ($1\times10^3$, $5\times10^3$ and $1\times10^4$) FIX levels were consistently higher in HUH7 cells transduced with ssAAV2/Mut C.HLP2.TI-ACNP-FIX-GoF relative to ssAAV2/MutC.HLP2.TI-codop-FIX-GoF (n=2; FIG. 2D, FIG. 2E, and FIG. 2F and FIG. 4D and FIG. 4E). When the $5\times10^3$ transduction data from the experiments FIG. 2A, FIG. 2B, FIG. 2C, FIG. 2D, FIG. 2E, and FIG. 2F, FIG. 3A, FIG. 3B, and FIG. 3C, and FIG. 4A, FIG. 4B, FIG. 4C, FIG. 4D, and FIG. 4E is combined, it shows significantly superior expression from ssAAV2/Mut C.HLP2.TI-ACNP-FIX-GoF relative to ssAAV2/Mut C.HLP2.TI-codop-FIX-GoF (FIG. 5).

Example 3—Analysis of In Vitro FIX Trans Gene Activity

Figure 9:
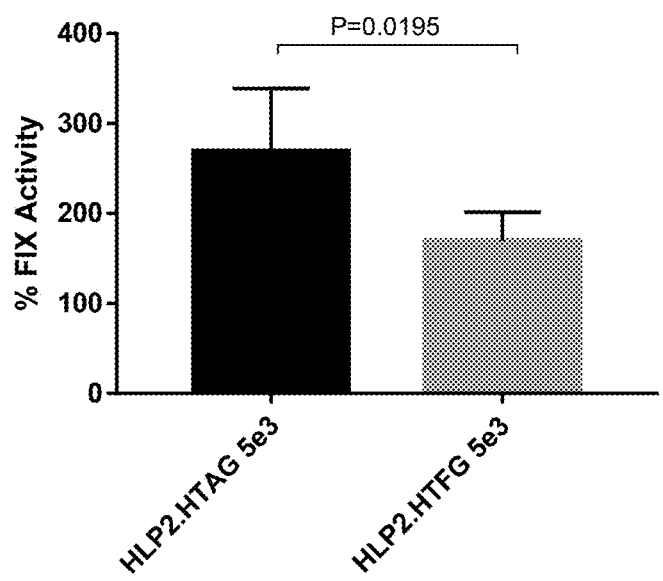
FIG. 9—Combined data (from Experiments 1 and 2.

FIX activity was assessed by harvesting HUH7 cell supernatant and using the BIOPHEN Factor IX kit (Quadratech #221806, #222101, #223201). Partially codon-optimised FIX transgenes (HLP2.TI-codop-FIX-GoF and HLP2.TI-ACNP-FIX-GoF) were compared in vitro to determine relative FIX activity following ssAAV2/Mut C transduction (at a MOI of $1\times10^3$, $5\times10^3$ and $1\times10^4$) of HUH7 cells. Supernatant was isolated from the HUH7 cells 5 days post-transduction, and FIX activity was determined using the BIOPHEN Factor IX kit. Regardless of the MOI, greater mean FIX activity was observed in supernatant derived from cells transduced with ssAAV2/Mut C.HLP2.TI-ACNP-FIX-GoF (FIG. 6A, FIG. 6B, and FIG. 6C, FIG. 7A, FIG. 7B, and FIG. 7C, and FIG. 8A, FIG. 8B, and FIG. 8C). When the $5\times10^3$ transduction data from the experiments of FIG. 6A, FIG. 6B, and FIG. 6C and FIG. 7A, FIG. 7B, and FIG. 7C is combined, it shows significantly superior expression from ssAAV2/Mut C.HLP2.TI-ACNP-FIX-GoF relative to ssAAV2/Mut C.HLP2.TI-codop-FIX-GoF (FIG. 9).

Example 4—Analysis of In Vivo FIX Transgene Expression Using ELISA

FIX transgenes were expressed in C57Bl/6 mice following transduction by tail-vein injection with $5\times10^{10}$ vector genomes (vg) of pseudotyped ssAAV2/8 vectors. AAV particles were first generated by transfection of HEK293 cells with recombinant vector genome plasmid, in addition to AAV helper and packaging plasmids, and culturing for a further 48 hours. ssAAV2/8 vectors were purified from the HEK293 cells by density gradient centrifugation and iodixanol. Vector genomes were titred by qPCR utilizing primers directed towards the promoter region of the transgene expression cassette. FIX expression cassettes LP1.FIXco, HLP2.TI-codop-FIX-GoF and HLP2.TI-ACNP-FIX-GoF were compared to determine their relative ability to express a FIX transgene.

In a first experiment involving ssAAV2/8.HLP2.TI-codop-FIX-GoF and ssAAV2/8.LP1.FIXco, 2 weeks post-dosing blood was collected from anaesthetised mice via cardiac puncture. Subsequently, plasma was isolated via the addition of sodium citrate (1/10 dilution) and centrifugation at 3000×g for 15 minutes at 4° C. Circulating levels of FIX were determined using a FIX ELISA kit (Stago Asserachrom IX:Ag kit Ref #00943).

Figure 10:
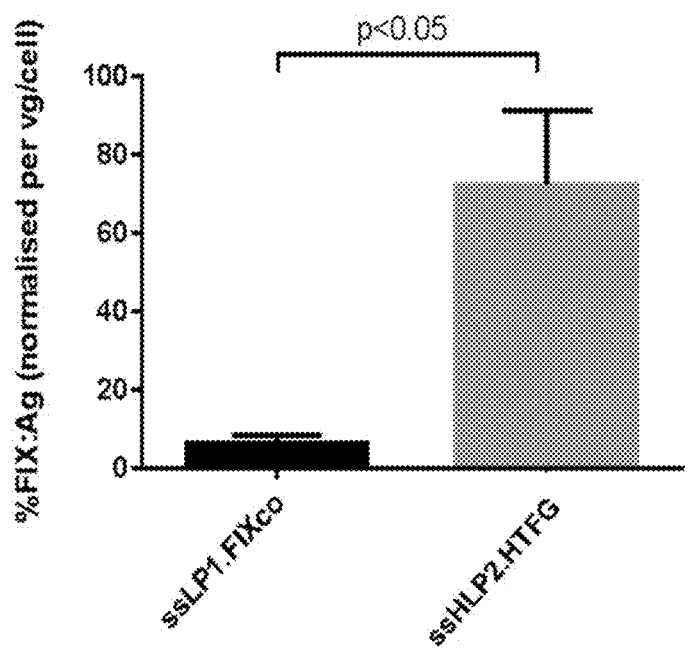
FIG. 10—Normalised level of human FIX in murine plasma after administration of AAV2/8.LP1.FIXco and AAV2/8.HLP2.HTFG (Experiment 3). FIX:Ag levels were normalised to vector copies/cell. Error bars represent mean±SD of n=4 mice. P-value <0.05 (Student's T-test)

FIX expression levels were normalised against copies of vector genome per cell following the harvesting of mouse liver. Normalised FIX expression levels were determined as being significantly higher (p<0.05) after transduction with ssAAV2/8.HLP2.TI-codop-FIX-GoF relative to ssAAV2/8.LP1.FIXco (n=4 mice; FIG. 10).

Figure 11A:
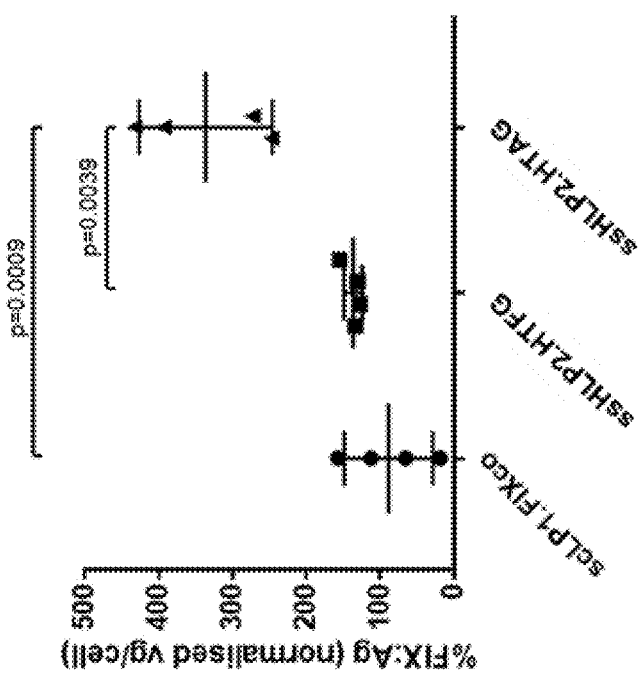
FIG. 11A and FIG. 11B—Comparison of alternate codon optimisation of FIX in C57BL/6 mice (Experiment 4). Mice were injected with AAV2/8 vectors containing ssHLP2.HTFG, ssHLP2.HTAG or scLP1.FIXco (control).
Figure 11B:
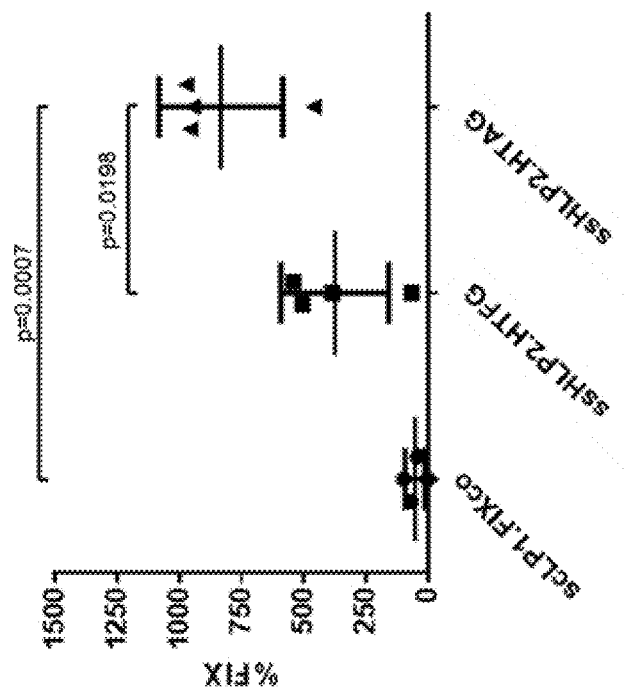

In a further experiment the partially codon-optimised FIX transgenes (HLP2.TI-codop-FIX-GoF and HLP2.TI-ACNP-FIX-GoF) were compared in vivo to determine relative FIX expression following C57Bl/6 mouse transduction with ssAAV2/8. Concurrently, FIX expression was determined following transduction of C57Bl/6 mice with the scAAV2/8.LP1.FIXco vector. Plasma was isolated from the mice 3 weeks post-dosing, and FIX antigen levels were determined using the ELISA assay. Mean FIX expression levels were lowest in mice transduced with scAAV2/8.LP1.FIXco, whilst levels were greater in mice transduced with ssAAV2/8.HLP2.TI-codop-FIX-GoF (n=4 mice; FIG. 11A). Mice transduced with ssAAV2/8.HLP2.TI-ACNP-FIX-GoF had significantly greater FIX expression than mice transduced with ssAAV2/8.HLP2.TI-codop-FIX-GoF (n=4 mice; FIG. 11A). When FIX expression levels were normalised against viral vector genome copies per cell the trend in FIX expression was maintained, whereby ssAAV2/8.HLP2.TI-ACNP-FIX-GoF produces significantly more FIX than both ssAAV2/8.HLP2.TI-codop-FIX-GoF and scAAV2/8.LP1.FIXco (n=4; FIG. 11B). Furthermore, ssAAV2/8.HLP2.TI-codop-FIX-GoF exhibited greater FIX expression than scAAV2/8.LP1.FIXco (n=4 mice; FIG. 11B).

Example 5—Analysis of In Vivo FIX Transgene Activity

BIOPHEN Factor IX kit (Quadratech #221806, #222101, #223201) is a chromogenic assay for measuring Factor IX activity in human citrated plasma or in Factor IX concentrates, using a manual chromogenic method.

In the presence of thrombin, phospholipids and calcium, first Factor XIa, supplied in the assay at a constant concentration and in excess, activates FIX, present in the tested sample, into FIXa, which forms an enzymatic complex with thrombin activated factor VIII:C, also supplied in the assay at a constant concentration and in excess, phospholipids (PLPs) and Calcium, that activates Factor X, present in the assay system, into Factor Xa. This activity is directly related to the amount of Factor IX, which is the limiting factor. Generated Factor Xa is then exactly measured by its specific activity on Factor Xa chromogenic substrate (SXa-11). Factor Xa cleaves the substrate and releases pNA. The amount of pNA generated is directly proportional to the Factor IXa activity. Finally, there is a direct relationship between the amount of Factor IX in the assayed sample and the Factor Xa activity generated, measured by the amount of pNA released, determined by colour development at 405 nm.

Figure 12:
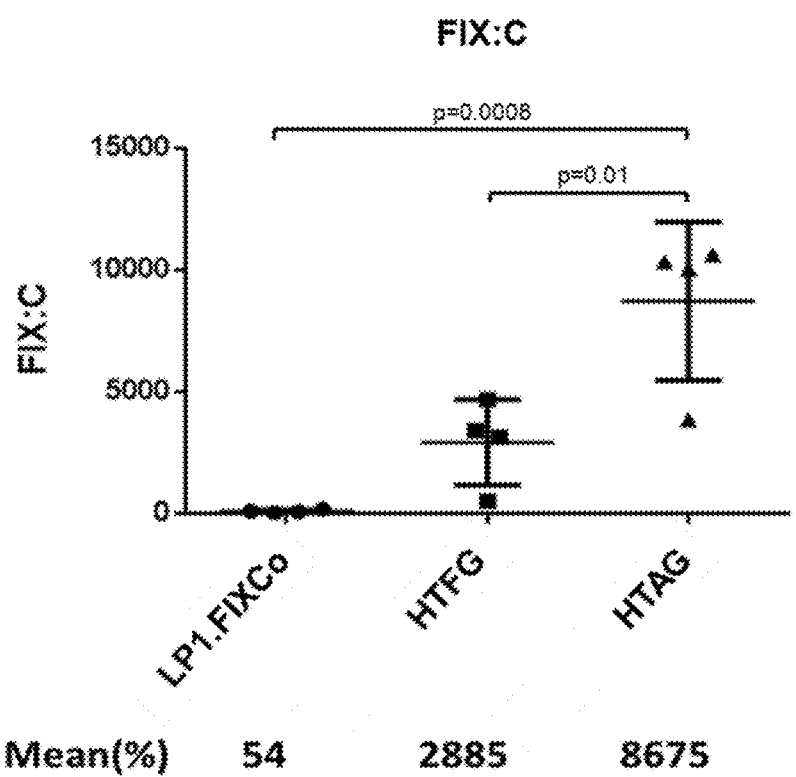
FIG. 12—Comparison of alternate codon optimisation of FIX in C57BL/6 mice (Experiment 4). Mice were injected with AAV2/8 vectors containing ssHLP2.HTFG, ssHLP2.HTAG or scLP1.FIXco (control). The level of FIX activity was assessed 3 weeks post-injection. n=4 mice. P=0.0008 between ssHLP2.HTAG and scLP1.FIXco and p=0.01 between ssHLP2.HTAG and ssHLP2.HTFG; p values were determined using one-way ANOVA (multiple comparison).

The partially codon-optimised FIX transgenes (HLP2.TI-codop-FIX-GoF and HLP2.TI-ACNP-FIX-GoF) were compared in vivo to determine relative FIX activity following C57Bl/6 mouse transduction with ssAAV2/8. Concurrently, FIX activity was determined following transduction of C57Bl/6 mice with scAAV2/8.LP1.FIXco. Plasma was isolated from the mice 3 weeks post-dosing, and FIX activity was determined using the BIOPHEN Factor IX kit. Mean FIX activity was lowest in mice transduced with scAAV2/8.LP1.FIXco, whilst activity was greater in mice transduced with ssAAV2/8.HLP2.TI-codop-FIX-GoF (n=4 mice; FIG. 12). Mice transduced with ssAAV2/8.HLP2.TI-ACNP-FIX-GoF had significantly greater FIX activity than mice transduced with ssAAV2/8.HLP2.TI-codop-FIX-GoF (n=4 mice; FIG. 12).

EMBODIMENTS

The invention described herein also relates to the following aspects:

1. A polynucleotide comprising a Factor IX nucleotide sequence, wherein the Factor IX nucleotide sequence comprises a coding sequence that encodes a Factor IX protein or fragment thereof and wherein a portion of the coding sequence is not wild type.
2. The polynucleotide of aspect 1, wherein the portion of the coding sequence that is not wild type is codon optimised.
3. A polynucleotide comprising a Factor IX nucleotide sequence, wherein the Factor IX nucleotide sequence comprises a coding sequence that encodes a Factor IX protein or a fragment thereof and the coding sequence comprises:
   (i) a sequence that is at least 95%, at least 98%, at least 99%, at least 99.5%, at least 99.8%, or 100% identical to SEQ ID NO.1; and
   (ii) a sequence that is at least 98%, at least 99%, at least 99.5%, at least 99.8%, or 100% identical to SEQ ID NO. 15.
4. The polynucleotide of aspect 3, wherein the sequence that is at least 95%, at least 98%, at least 99%, at least 99.5%, or at least 99.8% identical to SEQ ID NO. 1 is codon optimised.
5. A polynucleotide comprising a Factor IX nucleotide sequence, wherein the Factor IX nucleotide sequence encodes a Factor IX protein or fragment thereof and has at least 97%, at least 98%, at least 99%, at least 99.5%, at least 99.8%, or 100% identity to SEQ ID NO. 5.
6. The polynucleotide of aspect 5, wherein the Factor IX nucleotide sequence comprises a coding sequence and a portion of the coding sequence is codon optimised.
7. The polynucleotide of any one of the preceding aspects, wherein the polynucleotide comprises DNA or RNA.
8. The polynucleotide of any one of aspects 2, 4, 6 or 7, wherein the portion of the coding sequence that is codon optimised is a contiguous portion.
9. The polynucleotide of aspect 2, 4, 6, 7 or 8, wherein the portion of the coding sequence that is codon optimised is codon optimised for expression in the human liver.
10. The polynucleotide of any one of the preceding aspects, wherein a polypeptide encoded by the Factor IX nucleotide sequence is expressed in human liver cells at higher levels compared to a reference wild type Factor IX nucleotide sequence.
11. The polynucleotide of any one of aspects 2, 4, 6 or 7, wherein the portion of the coding sequence that is codon optimised is at least 800, at least 900, at least 1100, less than 1500, less than 1300, less than 1200, between 800 and 1500, between 900 and 1300, between 1100 and 1200, or around 1191 nucleotides in length.
12. The polynucleotide of any one of aspects 2, 4 or 6-11, wherein the portion of the coding sequence that is codon optimised comprises 1, 2, 3, 4, 5 or all of:

a) exon 3 or a portion of at least 10, at least 15, at least 20, less than 25, between 10 and 25, between 15 and 25, or between 20 and 25 nucleotides of exon 3;
b) exon 4 or a portion of at least 80, at least 90, at least 100, less than 114, between 80 and 114, between 90 and 114, or between 100 and 114 nucleotides of exon 4;
c) exon 5 or a portion of at least 90, at least 100, at least 110, less than 129, between 90 and 129, between 100 and 129, or between 110 and 129 nucleotides of exon 5;
d) exon 6 or a portion of at least 150, at least 180, at least 200, less than 203, between 150 and 203, between 180 and 203, or between 200 and 203 nucleotides of exon 6;
e) exon 7 or a portion of at least 70, at least 80, at least 90, at least 100, less than 115, between 70 and 115, between 80 and 115, between 90 and 115, or between 100 and 115 nucleotides of exon 7; and/or
f) exon 8 or a portion of at least 400, at least 450, at least 500, less than 548, between 400 and 548, between 450 and 548, or between 500 and 548 nucleotides of exon 8.

13. The polynucleotide of aspect 12, wherein the portion of the coding sequence that is codon optimised comprises a), b), c), d), e) and f).

14. The polynucleotide of aspect 12 or aspect 13, wherein the portion of the coding sequence that is codon optimised comprises a portion of at least 20 nucleotides of exon 3, a portion of at least 100 nucleotides of exon 4, a portion of at least 110 nucleotides of exon 5, a portion of at least 180 nucleotides of exon 6, a portion of at least 100 nucleotides of exon 7, and a portion of at least 500 nucleotides of exon 8.

15. The polynucleotide of any one of aspects 12-14, wherein the portion of the coding sequence that is codon optimised comprises exon 3, exon 4, exon 5, exon 6, exon 7, and exon 8.

16. The polynucleotide of any one of aspects 2, 4 or 6-15, wherein the portion of the coding sequence that is codon optimised comprises a portion of exon 2, and the portion of exon 2 is less than 160, less than 150, less than 100, less than 75, less than 60, at least 20, at least 30, at least 40, at least 50, between 20 and 160, between 30 and 150, between 30 and 100, between 40 and 75, or around 56 nucleotides in length.

17. The polynucleotide of any one of aspects 2, 4 or 6-16, wherein the portion of the coding sequence that is codon optimised comprises a portion of exon 2 that is between 30 and 100 nucleotides in length.

18. The polynucleotide of any one of aspects 2, 4 or 6-17, wherein the portion of the coding sequence that is codon optimised comprises a reduced number of CpGs compared to a corresponding portion of a reference wild type Factor IX sequence.

19. The polynucleotide of aspect 18, wherein the portion of the coding sequence that is codon optimised comprises less than less than 40, less than 20, less than 18, less than 10, less than 5, or less than 1 CpG.

20. The polynucleotide of aspect 18 or 19, wherein the portion of the coding sequence that is codon optimised is CpG free.

21. The polynucleotide of any one of aspects 2, 4 or 6-20, wherein, in the portion of the coding sequence that is codon optimised, at least 40%, at least 45%, at least 50%, at least 55%, at least 60%, at least 65%, at least 70%, or at least 73% of the codons are selected from the group consisting of:

a) TTC;
b) CTG;
c) ATC;
d) GTG;
e) GTC;
f) AGC;
g) CCC;
h) ACC;
i) GCC;
j) TAC;
k) CAC;
l) CAG;
m) AAC;
n) AAA;
o) AAG;
p) GAC;
q) TGC;
r) AGG;
s) GGC; and
t) GAG.

22. The polynucleotide of any one of aspects 2, 4 or 6-21, wherein, in the portion of the coding sequence that is codon optimised:
a) at least 1, at least 2, at least 4, or at least 5 codons that encode phenylalanine is/are replaced with TTC compared to a reference wild type Factor IX sequence;
b) at least 60%, at least 65%, or at least 70% of the codons that encode phenylalanine are TTC;
c) at least 60%, at least 65%, or at least 70% of the codons that encode phenylalanine are TTC and the remainder are TTT; and/or
d) the codons that encode phenylalanine are TTC, except where the following codon starts with a G.

23. The polynucleotide of any one of aspects 2, 4 or 6-22, wherein, in the portion of the coding sequence that is codon optimised:
a) at least 5, at least 10, at least 15, or at least 16 codons that encode leucine is/are replaced with CTG compared to a reference wild type Factor IX sequence;
b) at least 90%, or at least 94% of the codons that encode leucine are CTG; and/or
c) at least 90%, or at least 94% of the codons that encode leucine are CTG and the remainder are CTC.

24. The polynucleotide of any one of aspects 2, 4, 6-23, wherein, in the portion of the coding sequence that is codon optimised:
a) at least 5, at least 10, at least 11, or at least 12 codons that encode isoleucine is/are replaced with ATC compared to a reference wild type Factor IX sequence;
b) at least 1 of codon ATC is/are replaced with ATT compared to a reference wild type Factor IX sequence, where the following codon starts with a G;
c) at least 60%, at least 70%, or at least 75% of the codons that encode isoleucine are ATC;
d) at least 60%, at least 70%, or at least 75% of the codons that encode isoleucine are ATC and the remainder are ATT; and/or
e) the codons that encode isoleucine are ATC, except where the following codon starts with a G.

25. The polynucleotide of any one of aspects 2, 4 or 6-24, wherein, in the portion of the coding sequence that is codon optimised:
a) at least 10, at least 15, at least 20, or at least 25 codons that encode valine is/are replaced with GTG compared to a reference wild type Factor IX sequence;

b) at least 1 codon that encodes valine is/are replaced with GTC compared to a reference wild type Factor IX sequence;
c) at least 80%, at least 90%, or at least 95% of the codons that encode valine are GTG; and/or
d) at least 80%, at least 90%, or at least 95% of the codons that encode valine are GTG and the remainder are GTC.

26. The polynucleotide of any one of aspects 2, 4 or 6-25, wherein, in the portion of the coding sequence that is codon optimised:
a) at least 5, at least 10, at least 12, or at least 13 codons that encode serine is/are replaced with AGC compared to a reference wild type Factor IX sequence;
b) at least 1, at least 2, or at least 4 codons that encode serine is/are replaced with TCT compared to a reference wild type Factor IX sequence, where the following codon starts with a G;
c) at least 60%, at least 65%, or at least 70% of the codons that encode serine are AGC; and/or
d) at least 60%, at least 65%, or at least 70% of the codons that encode serine are AGC and the remainder are TCT or TCC.

27. The polynucleotide of any one of aspects 2, 4 or 6-26, wherein, in the portion of the coding sequence that is codon optimised:
a) at least 1, at least 2, or at least 5 codons that encode proline is/are replaced with CCC compared to a reference wild type Factor IX sequence;
b) at least 1 codons that encode proline is/are replaced with CCT compared to a reference wild type Factor IX sequence, where the following codon starts with a G;
c) at least 50%, at least 55%, or at least 60% of the codons that encode proline are CCC;
d) at 50%, at least 55%, or at least 60% of the codons that encode proline are CCC and the remainder are CCA or CCT; and/or
e) the codons that encode proline are CCC, except where the following codon starts with a G.

28. The polynucleotide of any one of aspects 2, 4 or 6-27, wherein, in the portion of the coding sequence that is codon optimised:
a) at least 6, at least 7, at least 8, or at least 10 codons that encode threonine is/are replaced with ACC compared to a reference wild type Factor IX sequence;
b) at least 1, or at least 2, codons that encode threonine is/are replaced with ACT compared to a reference wild type Factor IX sequence, where the following codon starts with a G;
c) at least 45%, at least 50%, or at least 55% of the codons that encode threonine are ACC;
d) at least 45%, at least 50%, or at least 55% of the codons that encode threonine are ACC and the remainder are ACT; and/or
e) the codons that encode threonine are ACC, except where the following codon starts with a G.

29. The polynucleotide of any one of aspects 2, 4 or 6-28, wherein, in the portion of the coding sequence that is codon optimised:
a) at least 1, at least 2, at least 3, or at least 4 codons that encode alanine is/are replaced with GCC compared to a reference wild type Factor IX sequence;
b) at least 1, at least 2, or at least 3 codons that encode alanine is/are replaced with GCT compared to a reference wild type Factor IX sequence, where the following codon starts with a G;
c) at least 35%, at least 40%, or at least 43% of the codons that encode alanine are GCC;
d) at least 35%, at least 40%, or at least 45% of the codons that encode alanine are GCC and the remainder are GCT; and/or
e) the codons that encode alanine are GCC, except where the following codon starts with a G.

30. The polynucleotide of any one of aspects 2, 4 or 6-29, wherein, in the portion of the coding sequence that is codon optimised:
a) at least 1, or at least 2 codons that encode tyrosine is/are replaced with TAC compared to a reference wild type Factor IX sequence;
b) at least 1 of codon TAC is/are replaced with TAT compared to a reference wild type Factor IX sequence, where the following codon starts with a G;
c) at least 40%, at least 45%, or at least 48% of the codons that encode tyrosine are TAC;
d) at least 40%, at least 45%, or at least 48% of the codons that encode tyrosine are TAC and the remainder are TAT; and/or
e) the codons that encode tyrosine are TAC, except where the following codon starts with a G.

31. The polynucleotide of any one of aspects 2, 4 or 6-30, wherein, in the portion of the coding sequence that is codon optimised:
a) at least 1 codons that encode histidine is/are replaced with CAC compared to a reference wild type Factor IX sequence;
b) at least 50%, at least 60%, or at least 65% of the codons that encode histidine are CAC;
c) at least 50%, at least 60%, or at least 65% of the codons that encode histidine are CAC and the remainder are CAT; and/or
d) the codons that encode histidine are CAC, except where the following codon starts with a G.

32. The polynucleotide of any one of aspects 2, 4 or 6-31, wherein, in the portion of the coding sequence that is codon optimised:
a) at least 1, at least 2, at least 4, or at least 5 codons that encode glutamine is/are replaced with CAG compared to a reference wild type Factor IX sequence;
b) at least 1 of codon CAG is/are replaced with CAA compared to a reference wild type Factor IX sequence;
c) at least 80%, at least 85%, or at least 90% of the codons that encode glutamine are CAG; and/or
d) at least 80%, at least 85%, or at least 90% of the codons that encode glutamine are CAG and the remainder are CAA.

33. The polynucleotide of any one of aspects 2, 4 or 6-32, wherein, in the portion of the coding sequence that is codon optimised:
a) at least 1, at least 2, at least 4, or at least 5 codons that encode asparagine is/are replaced with AAC compared to a reference wild type Factor IX sequence;
b) at least 60%, at least 65%, or at least 70% of the codons that encode asparagine are AAC;
c) at least 60%, at least 65%, or at least 70% of the codons that encode asparagine are AAC and the remainder are AAT; and/or
d) the codons that encode asparagine are AAC, except where the following codon starts with a G.

34. The polynucleotide of any one of aspects 2, 4 or 6-33, wherein, in the portion of the coding sequence that is codon optimised:

a) at least 5, at least 7, at least 8, or at least 9 codons that encode lysine is/are replaced with AAG compared to a reference wild type Factor IX sequence;
b) at least 1 of codon AAG is/are replaced with AAA compared to a reference wild type Factor IX sequence;
c) at least 80%, at least 90%, or at least 95% of the codons that encode lysine are AAG; and/or
d) at least 80%, at least 90%, or at least 95% of the codons that encode lysine are AAG and the remainder are AAA.

35. The polynucleotide of any one of aspects 2, 4 or 6-34, wherein, in the portion of the coding sequence that is codon optimised:
a) at least 1, at least 2, at least 3, or at least 4 codons that encode aspartate is/are replaced with GAC compared to a reference wild type Factor IX sequence; b) at least 1 of codon GAC is/are replaced with GAT compared to a reference wild type Factor IX sequence, where the following codon starts with a G;
c) at least 45%, at least 50%, or at least 60% of the codons that encode aspartate are GAC;
d) at least 45%, at least 50%, or at least 60% of the codons that encode aspartate are GAC and the remainder are GAT; and/or
e) the codons that encode aspartate are GAC, except where the following codon starts with a G.

36. The polynucleotide of any one of aspects 2, 4 or 6-35, wherein, in the portion of the coding sequence that is codon optimised:
a) at least 15, at least 20, at least 25, or at least 26 codons that encode glutamate is/are replaced with GAG compared to a reference wild type Factor IX sequence;
b) at least 80%, at least 90%, or at least 95% of the codons that encode glutamate are GAG; and/or
c) at least 80%, at least 90%, or at least 95% of the codons that encode glutamate are GAG and the remainder are GAA.

37. The polynucleotide of any one of aspects 2, 4, or 6-36, wherein, in the portion of the coding sequence that is codon optimised:
a) at least 5, at least 6, at least 7, or at least 8 codons that encode cysteine is/are replaced with TGC compared to a reference wild type Factor IX sequence;
b) at least 1 of codon TGC is/are replaced with TGT compared to a reference wild type Factor IX sequence, where the following codon starts with a G;
c) at least 40%, at least 50%, or at least 55% of the codons that encode cysteine are TGC;
d) at least 40%, at least 50%, or at least 55% of the codons that encode cysteine are TGC and the remainder are TGT; and/or
e) the codons that encode cysteine are TGC, except where the following codon starts with a G.

38. The polynucleotide of any one of aspects 2, 4, or 6-37, wherein, in the portion of the coding sequence that is codon optimised the codons that encode tryptophan are TGG.

39. The polynucleotide of any one of aspects 2, 4, or 6-38, wherein, in the portion of the coding sequence that is codon optimised:
a) at least 5, at least 8, at least 10, or at least 11 codons that encode arginine is/are replaced with AGG compared to a reference wild type Factor IX sequence;
b) at least 1 codon that encodes arginine is/are replaced with AGA compared to a reference wild type Factor IX sequence;
c) at least 60%, at least 70%, or at least 75% of the codons that encode arginine are AGG; and/or
d) at least 60%, at least 70%, or at least 75% of the codons that encode arginine are AGG and the remainder are AGA.

40. The polynucleotide of any one of aspects 2, 4, or 6-39, wherein, in the portion of the coding sequence that is codon optimised:
a) at least 5, at least 10, at least 12, or at least 13 codons that encode glycine is/are replaced with GGC compared to a reference wild type Factor IX sequence; b) at least 5, at least 6, at least 7, or at least 8 codons that encode glycine is/are replaced with GGG compared to a reference wild type Factor IX sequence, where the following codon starts with a G;
c) at least 50%, at least 55%, or at least 60% of the codons that encode glycine are GGC;
d) at least 50%, at least 55%, or at least 60% of the codons that encode glycine are GGC and the remainder are GGG; and/or
e) the codons that encode glycine are GGC, except where the following codon starts with a G.

41. The polynucleotide of any one of aspects 2, 4, or 6-40, wherein the portion of the coding sequence that is codon optimised comprises codons that encode phenylalanine, leucine, isoleucine, valine, serine, proline, threonine, alanine, tyrosine, histidine, glutamine, asparagine, lysine, aspartate, glutamate, cysteine, tryptophan, arginine, and glycine.

42. The polynucleotide of any one of aspects 2, 4, or 6-41, wherein the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimised portion:
a) at least 5 codons that encode phenylalanine is/are replaced with TTC compared to a reference wild type Factor IX sequence;
b) at least 16 codons that encode leucine is/are replaced with CTG compared to a reference wild type Factor IX sequence;
c) at least 12 codons that encode isoleucine is/are replaced with ATC compared to a reference wild type Factor IX sequence;
d) at least 25 codons that encode valine is/are replaced with GTG compared to a reference wild type Factor IX sequence;
e) at least 13 codons that encode serine is/are replaced with AGC compared to a reference wild type Factor IX sequence;
f) at least 5 codons that encode proline is/are replaced with CCC compared to a reference wild type Factor IX sequence;
g) at least 10 codons that encode threonine is/are replaced with ACC compared to a reference wild type Factor IX sequence;
h) at least 4 codons that encode alanine is/are replaced with GCC compared to a reference wild type Factor IX sequence;
i) at least 2 codons that encode tyrosine is/are replaced with TAC compared to a reference wild type Factor IX sequence;
j) at least 1 codons that encode histidine is/are replaced with CAC compared to a reference wild type Factor IX sequence;

k) at least 5 codons that encode glutamine is/are replaced with CAG compared to a reference wild type Factor IX sequence;
l) at least 5 codons that encode asparagine is/are replaced with AAC compared to a reference wild type Factor IX sequence;
m) at least 9 codons that encode lysine is/are replaced with AAG compared to a reference wild type Factor IX sequence;
n) at least 4 codons that encode aspartate is/are replaced with GAC compared to a reference wild type Factor IX sequence;
o) at least 26 codons that encode glutamate is/are replaced with GAG compared to a reference wild type Factor IX sequence;
p) at least 8 codons that encode cysteine is/are replaced with TGC compared to a reference wild type Factor IX sequence;
q) the codons that encode tryptophan are TGG;
r) at least 11 codons that encode arginine is/are replaced with AGG compared to a reference wild type Factor IX sequence; and
s) at least 13 codons that encode glycine is/are replaced with GGC compared to a reference wild type Factor IX sequence.

43. The polynucleotide of any one of aspects 2, 4, or 6-42, wherein the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimised portion:
a) at least 70% of the codons that encode phenylalanine are TTC;
b) at least 94% of the codons that encode leucine are CTG;
c) at least 75% of the codons that encode isoleucine are ATC;
d) at least 95% of the codons that encode valine are GTG;
e) at least 70% of the codons that encode serine are AGC;
f) at least 60% of the codons that encode proline are CCC;
g) at least 55% of the codons that encode threonine are ACC;
h) at least 43% of the codons that encode alanine are GCC;
i) at least 48% of the codons that encode tyrosine are TAC;
j) at least 65% of the codons that encode histidine are CAC;
k) at least 90% of the codons that encode glutamine are CAG;
l) at least 70% of the codons that encode asparagine are AAC;
m) at least 95% of the codons that encode lysine are AAG;
n) at least 60% of the codons that encode aspartate are GAC;
o) at least 95% of the codons that encode glutamate are GAG;
p) at least 55% of the codons that encode cysteine are TGC;
q) the codons that encode tryptophan are TGG;
r) at least 75% of the codons that encode arginine are AGG; and
s) at least 60% of the codons that encode glycine are GGC.

44. The polynucleotide of any one of aspects 2, 4, or 6-43, wherein the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimised portion:
a) at least 70% of the codons that encode phenylalanine are TTC and the remainder are TTT;
b) at least 94% of the codons that encode leucine are CTG and the remainder are CTC;
c) at least 75% of the codons that encode isoleucine are ATC and the remainder are ATT;
d) at least 95% of the codons that encode valine are GTG;
e) at least 70% of the codons that encode serine are AGC;
f) at least 60% of the codons that encode proline are CCC and the remainder are CCA or CCT;
g) at least 55% of the codons that encode threonine are ACC and the remainder are ACT;
h) at least 43% of the codons that encode alanine are GCC and the remainder are GCT;
i) at least 48% of the codons that encode tyrosine are TAC and the remainder are TAT;
j) at least 65% of the codons that encode histidine are CAC and the remainder are CAT;
k) at least 90% of the codons that encode glutamine are CAG and the remainder are CAA;
l) at least 70% of the codons that encode asparagine are AAC and the remainder are AAT;
m) at least 95% of the codons that encode lysine are AAG and the remainder are AAA;
n) at least 60% of the codons that encode aspartate are GAC and the remainder are GAT;
o) at least 95% of the codons that encode glutamate are GAG and the remainder are GAA;
p) at least 55% of the codons that encode cysteine are TGC and the remainder are TGT;
q) the codons that encode tryptophan are TGG;
r) at least 75% of the codons that encode arginine are AGG and the remainder are AGA; and
s) at least 60% of the codons that encode glycine are GGC and the remainder are GGG.

45. The polynucleotide of any one of aspects 10-44, wherein the reference wild type Factor IX sequence is SEQ ID NO. 9 or SEQ ID NO. 19.

46. The polynucleotide of any one of aspects 2, 4 or 6-45, wherein the portion of the coding sequence that is codon optimised is at least 80%, at least 85%, at least 90%, at least 95%, at least 98%, at least 99%, at least 99.5%, at least 99.8%, or 100% identical to a fragment of at least 800, at least 900, at least 1100, less than 1191, less than 1100, less than 1000, between 800 and 1191, between 900 and 1191, or around 1191 nucleotides of SEQ ID NO. 1.

47. The polynucleotide of aspect 46, wherein the portion of the coding sequence that is codon optimised is at least 80%, at least 85%, at least 90%, at least 95%, at least 98%, at least 99%, at least 99.5%, at least 99.8%, or 100% identical to SEQ ID NO. 1.

48. The polynucleotide of aspect 46 or 47, wherein the portion of the coding sequence that is codon optimised is at least 95% identical to a fragment of between 900 and 1191 nucleotides of SEQ ID NO. 1.

49. The polynucleotide of any one of aspects 46-48, wherein the portion of the coding sequence that is codon optimised is at least 95%, or at least 98% identical to SEQ ID NO. 1.

50. The polynucleotide of any one of the preceding aspects, wherein the coding sequence comprises a portion that is not codon optimised.

51. The polynucleotide of aspect 50, wherein the portion that is not codon optimised is at least 100, at least 150, at least 170, at least 190, less than 250, less than 225, less than 200, or around 195 nucleotides.

52. The polynucleotide of any one of aspects 50 or 51, wherein the portion that is not codon optimised comprises exon 1 or a portion of at least 60, at least 70, at least 80, between 60 and 88, between 70 and 88, or between 80 and 88 nucleotides of exon 1.

53. The polynucleotide of any one of aspects 50-52, wherein the portion that is not codon optimised comprises a portion of at least 50, at least 75, at least 80, at least 90, at least 100, less than 140, less than 120, between 50 and 140, between 75 and 120, or around 107 nucleotides of exon 2.

54. The polynucleotide of any one of aspects 50-53, wherein the portion that is not codon optimised comprises CpGs.

55. The polynucleotide of aspect 54, wherein the portion that is not codon optimised comprises at least 1 or at least 2 CpGs per 100 nucleotides.

56. The polynucleotide of any one of aspects 50-55, wherein the portion that is not codon optimised comprises less than 50%, less than 45%, less than 40%, or less than 35% codons selected from the group consisting of:
    a) TTC;
    b) CTG;
    c) ATC;
    d) GTG;
    e) GTC;
    f) AGC;
    g) CCC;
    h) ACC;
    i) GCC;
    j) TAC;
    k) CAC;
    l) CAG;
    m) AAC;
    n) AAA;
    o) AAG;
    p) GAC;
    q) TGC;
    r) AGG;
    s) GGC; and
    t) GAG.

57. The polynucleotide of any one of aspects 50-56, wherein the portion that is not codon optimised is at least 80%, at least 85%, at least 90%, at least 95%, at least 98%, at least 99%, at least 99.5%, at least 99.8%, or 100% identical to a fragment of at least 100, at least 150, at least 175, less than 195, less than 190, or less than 180 nucleotides of SEQ ID NO. 15.

58. The polynucleotide of aspect 57, wherein the portion that is not codon optimised is at least 80%, at least 85%, at least 90%, at least 95%, at least 98%, at least 99%, at least 99.5%, at least 99.8%, or 100% identical to SEQ ID NO. 15.

59. The polynucleotide of any one of aspects 50-58, wherein the portion that is not codon optimised is wild type.

60. The polynucleotide of any one of aspects 50-59, wherein the portion that is not codon optimised is at least 90%, at least 95%, at least 98%, at least 99%, at least 99.5%, at least 99.8%, or 100% identical to SEQ ID NO: 15.

61. The polynucleotide of any one of the preceding aspects, wherein the polynucleotide further comprises an intron or a fragment of an intron that interrupts the coding sequence.

62. The polynucleotide of aspect 61, wherein the intron or the fragment of an intron is a portion of a wild type Factor IX intron.

63. The polynucleotide of aspect 61 or 62, wherein the fragment of an intron is less than 500, less than 400, less than 350, less than 300, at least 100, at least 200, at least 250, at least 290, between 100 and 500, between 200 and 400, between 250 and 350, or around 299 nucleotides.

64. The polynucleotide of any one of aspects 61-63, wherein the fragment of an intron is at least 80%, at least 85%, at least 90%, at least 95%, at least 98%, at least 99%, at least 99.5%, at least 99.8%, or 100% identical to a fragment of at least 100, at least 200, at least 250, or at least 290 nucleotides of SEQ ID NO. 3.

65. The polynucleotide of any one of aspects 61-64, wherein the intron or the fragment of an intron is at least 85%, at least 90%, at least 95%, at least 98%, at least 99%, at least 99.5%, at least 99.8%, or 100% identical to SEQ ID NO.3.

66. The polynucleotide of aspect 65, wherein the intron or the fragment of an intron is at least 95%, or at least 98% identical to SEQ ID NO.3.

67. The polynucleotide of any one of aspects 61-66, wherein the intron or the fragment of an intron interrupts the portion that is not codon optimised.

68. The polynucleotide of aspect 67, wherein the intron or the fragment of an intron is flanked by at least 60, at least 70, at least 80, at least 90, or at least 100 nucleotides that are not codon optimised.

69. The polynucleotide of aspect 68, wherein the intron or the fragment of an intron is flanked by between 110 and 120 nucleotides that are not codon optimised at the 5' end and between 100 and 110 nucleotides that are not codon optimised at the 3' end.

70. The polynucleotide of any one of aspects 61-69, wherein the intron or the fragment of an intron is positioned between exon 1 and exon 2.

71. The polynucleotide of any one of aspects 61-70, wherein the intron or the fragment of the intron is a fragment of native intron 1 (intron 1a).

72. The polynucleotide of any one of the preceding aspects, wherein the polynucleotide further comprises a transcription regulatory element.

73. The polynucleotide of aspect 72, wherein the transcription regulatory element comprises a liver-specific promoter.

74. The polynucleotide of aspect 72 or aspect 73, wherein the transcription regulatory element comprises an A1AT promoter or a fragment of an A1AT promoter.

75. The polynucleotide of aspect 74, wherein the fragment of an A1AT promoter is at least 100, at least 120, at least 150, at least 180, less than 255, between 100 and 255, between 150 and 225, between 150 and 300, or between 180 and 255 nucleotides in length.

76. The polynucleotides of aspect 75, wherein the fragment of an A1AT promoter is between 150 and 300 nucleotides in length.

77. The polynucleotides, of any one of aspects 72-76, wherein the transcription regulatory element comprises an enhancer.

78. The polynucleotide of aspect 77, wherein the enhancer is an HCR enhancer or a fragment of an HCR enhancer.

79. The polynucleotide of aspect 78, wherein the fragment of an HCR enhancer is a fragment of at least 80, at least 90, at least 100, less than 192, between 80 and 192, between 90 and 192, between 100 and 250, or between 117 and 192 nucleotides in length.

80. The polynucleotide of aspect 79, wherein the fragment of an HCR enhancer is between 100 and 250 nucleotides in length.

81. The polynucleotide of any one of aspects 72-80, wherein the transcription regulatory element is at least 80%, at least 85%, at least 90%, at least 95%, at least 98%, at least 99%, at least 99.5%, at least 99.8%, or 100% identical to SEQ ID NO. 6.

82. The polynucleotide of aspect 81, wherein the transcription regulatory element has a sequence of SEQ ID NO. 6.

83. The polynucleotide of any one of the preceding aspects, wherein the polynucleotide comprises an enhancer that is at least 80%, at least 85%, at least 90%, at least 95% at least 98%, at least 99%, at least 99.5%, at least 99.8%, or 100% identical to SEQ ID NO. 13.

84. The polynucleotide of any one of the preceding aspects, wherein the polynucleotide comprises an enhancer that is at least 98%, at least 99%, at least 99.5%, at least 99.8%, or 100% identical to SEQ ID NO. 13.

85. The polynucleotide of any one of the preceding aspects, wherein the polynucleotide comprises an enhancer of SEQ ID NO. 13.

86. The polynucleotide of any one of the preceding aspects, wherein the polynucleotide comprises a promoter that is at least 80%, at least 85%, at least 90%, at least 95% at least 98%, at least 99%, at least 99.5%, at least 99.8%, or 100% identical to SEQ ID NO. 14.

87. The polynucleotide of any one of the preceding aspects, wherein the polynucleotide comprises a promoter that is at least 98%, at least 99%, at least 99.5%, at least 99.8%, or 100% identical to SEQ ID NO. 14.

88. The polynucleotide of any one of the preceding aspects, wherein the polynucleotide comprises a promoter of SEQ ID NO. 14.

89. The polynucleotide of any one of the preceding aspects, wherein the Factor IX nucleotide sequence comprises a codon that encodes an amino acid at a position corresponding to codon 384 of wild type factor IX, and wherein the codon that encodes an amino acid at a position corresponding to position 384 of wild type Factor IX encodes alanine or leucine.

90. The polynucleotide of aspect 89, wherein the codon that encodes an amino acid at a position corresponding to position 384 of wild type Factor IX is CTX, wherein X is any nucleotide.

91. The polynucleotide of any one of the preceding aspects, wherein the polynucleotide comprises a Factor IX nucleotide sequence that is at least 80%, at least 85%, at least 90%, at least 95%, at least 98%, at least 99%, at least 99.5%, at least 99.8%, or 100% identical to a fragment at least 1200, at least 1350, or at least 1650 nucleotides of SEQ ID NO. 5.

92. The polynucleotide of any one of the preceding aspects, wherein the polynucleotide comprises a Factor IX nucleotide sequence that is at least 80%, at least 85%, at least 90%, at least 95%, at least 98%, at least 99%, at least 99.5%, at least 99.8%, or 100% identical to SEQ ID NO.5.

93. The polynucleotide of any one of the preceding aspects, wherein:
(i) the Factor IX nucleotide sequence comprises a sequence that is at least 95%, at least 98%, at least 99%, at least 99.5%, at least 99.8%, or 100% identical to SEQ ID NO.1; and
(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.

94. The polynucleotide of any one of the preceding aspects, wherein:
(i) the Factor IX nucleotide sequence comprises a coding sequence that is at least 95%, at least 98%, at least 99%, at least 99.5%, at least 99.8%, or 100% identical to SEQ ID NO.1;
(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine; and
(iii) the polynucleotide comprises a promoter element that is at least 98%, at least 99%, at least 99.5%, at least 99.8%, or 100% identical to SEQ ID NO. 14 and/or an enhancer element that is at least 98%, at least 99%, at least 99.5%, at least 99.8% or 100% identical to SEQ ID NO. 13.

95. The polynucleotide of any one of the preceding aspects, wherein:
(i) the Factor IX nucleotide sequence comprises a sequence that is at least 95%, at least 98%, at least 99%, at least 99.5%, at least 99.8%, or 100% identical to SEQ ID NO.1;
(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine; and
(iii) the polynucleotide comprise a transcription regulatory element that is at least 98%, at least 99%, at least 99.5%, at least 99.8%, or 100% identical to SEQ ID NO. 6.

96. The polynucleotide of any one of the preceding aspects, wherein:
(i) the Factor IX nucleotide sequence comprises a sequence that is at least 95%, at least 98%, at least 99%, at least 99.5%, at least 99.8%, or 100% identical to SEQ ID NO.1;
(ii) the Factor IX nucleotide sequence comprises a sequence that is at least 98%, at least 99%, at least 99.5%, at least 99.8%, or 100% identical to a corresponding portion of SEQ ID NO: 2; and
(iii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.

97. The polynucleotide of any one of aspects 95 or 96, wherein the Factor IX nucleotide sequence comprises an intron or a fragment of an intron, and the fragment of an intron is at least 98%, at least 99%, at least 99.5%, at least 99.8%, or 100% identical to SEQ ID NO. 3.

98. The polynucleotide of any one of the preceding aspects, wherein:
(i) the Factor IX nucleotide sequence comprises a coding sequence and a portion of the coding sequence is not codon optimised; and
(ii) the Factor IX nucleotide sequence comprises a codon that encodes an amino acid at a position corresponding to position 384 of wild type Factor IX wherein the codon that encodes an amino acid at a position corresponding to position 384 of wild type Factor IX encodes leucine.

99. The polynucleotide of any one of the preceding aspects, wherein a polypeptide encoded by the Factor IX nucleotide sequence is expressed in human liver cells at higher levels compared to a polypeptide encoded by a nucleotide sequence comprising a Factor IX nucleotide sequence of SEQ ID NO. 12 and a transcription regulatory element of SEQ ID NO. 7.

100. The polynucleotide of any one of the preceding aspects, wherein a polypeptide encoded by the Factor IX nucleotide sequence is expressed in human liver cells at higher levels compared to a polypeptide encoded by a nucleotide sequence comprising a Factor IX nucleotide sequence of SEQ ID NO. 18 and a transcription regulatory element of SEQ ID NO. 6.

101. The polynucleotide of any one of the preceding aspects, wherein a polypeptide encoded by the Factor IX nucleotide sequence is expressed in human liver cells at a level at least 2, or at least 3 times greater than a polypeptide encoded by a nucleotide sequence comprising a Factor IX nucleotide sequence of SEQ ID NO. 12 or SEQ ID NO. 18 and a transcription regulatory element of SEQ ID NO. 7 or SEQ ID NO. 6.

102. A viral particle comprising a recombinant genome comprising the polynucleotide of any one of the preceding aspects.

103. The viral particle of aspect 102, which is an AAV, adenoviral, or lentiviral viral particle.

104. The viral particle of aspect 103, which is an AAV viral particle.

105. The viral particle of any one of aspects 102-104, wherein the recombinant genome further comprises:
   a) AAV2 ITRs;
   b) a poly A sequence;
   c) an origin of replication; and/or
   d) two resolvable ITRs.

106. The viral particle of aspect 105, wherein the recombinant genome is single-stranded and/or comprises two resolvable ITRs.

107. The viral particle of any one of aspects 102-106, wherein the viral particle comprises a capsid selected from the group consisting of:
   (i) a capsid having at least 96%, at least 98%, at least 99%, at least 99.5%, at least 99.8% identity or 100% identity to SEQ ID NO.10;
   (ii) a capsid having at least 96%, at least 98%, at least 99%, at 99.5%, at least 99.8%, or 100% identity to SEQ ID NO. 17;
   (iii) AAVMutC; and
   (iv) AAV5.

108. The viral particle of any one of aspects 102-107, wherein on transduction into Huh7 cells, the viral particle expresses Factor IX protein or a fragment thereof having a Factor IX activity greater than the activity of Factor IX expressed from a viral particle comprising a Factor IX nucleotide sequence of SEQ ID NO: 12 and a transcription regulatory element of SEQ ID NO. 7 and/or a viral particle comprising a Factor IX nucleotide sequence of SEQ ID NO. 18 and a transcription regulatory element of SEQ ID NO. 6.

109. The viral particle of aspect 108, wherein the activity is measured using a chromogenic substrate which is specific for Factor Xa.

110. The polynucleotide or viral particle of any one of the preceding aspects, wherein the Factor IX protein fragment is at least 200, at least 250, at least 300, between 200 and 415, between 250 and 415, or between 300 and 415 amino acids in length.

111. The polynucleotide or viral particle of any one of the preceding aspects, wherein the Factor IX protein or fragment thereof comprises a sequence:
   a) at least 95%, at least 98%, at least 99%, at least 99.5%, at least 99.8%, or 100% identical to SEQ ID NO. 8; or
   b) at least 95%, at least 98%, at least 99%, at least 99.5%, at least 99.8%, or 100% identical to a fragment of SEQ ID NO. 8 at least 200, at least 250, at least 300, between 200 and 415, between 250 and 415, or between 300 and 415 amino acids in length.

112. A composition comprising the polynucleotide or viral particle of any one of the preceding aspects and a pharmaceutically acceptable excipient.

113. The polynucleotide, viral particle or composition of any one of the preceding aspects for use in a method of treatment.

114. The polynucleotide, viral particle or composition for use of aspect 113, wherein the method of treatment comprises administering an effective amount of the polynucleotide or viral particle of any one of aspects 1-111 to a patient.

115. A method of treatment comprising administering an effective amount of the polynucleotide or viral particle of any one of aspects 1-111 to a patient.

116. Use of the polynucleotide, viral particle or composition of any one of aspects 1-111 in the manufacture of a medicament for use in a method of treatment.

117. The use of aspect 116, wherein the method of treatment comprises administering an effective amount of the polynucleotide or viral particle of any one of aspects 1-111 to a patient.

118. The polynucleotide, viral particle, composition, use or method of any one of aspects 112-117, wherein the method of treatment is a method of treating haemophilia.

119. The polynucleotide, viral particle, composition, use or method of aspect 118, wherein the haemophilia is haemophilia B.

120. The polynucleotide, viral particle, composition, use or method of aspect 119, wherein the patient has antibodies or inhibitors to Factor IX.

The invention claimed is:

1. A method of treating a haemophilia patient in need thereof, the method comprising administering an effective amount of a polynucleotide comprising a Factor IX nucleotide sequence to the patient, wherein:
   (i) the Factor IX nucleotide sequence comprises a coding sequence that encodes a Factor IX protein that is at least 95% identical to a fragment of SEQ ID NO. 16 that is from 200 to 461 amino acids in length;
   (ii) a portion of the coding sequence is codon optimized;
   (iii) the portion of the coding sequence that is codon optimized is at least 1100 nucleotides in length;
   (iv) in the portion that is codon optimized at least 73% of the codons are selected from the group consisting of:
   TTC encoding phenylalanine,
   CTG encoding leucine,
   ATC encoding isoleucine,
   GTG or GTC encoding valine,
   AGC encoding serine,
   CCC encoding proline,
   ACC encoding threonine,
   GCC encoding alanine,
   TAC encoding tyrosine,
   CAC encoding histidine,
   CAG encoding glutamine,
   AAC encoding asparagine,
   AAA or AAG encoding lysine,
   GAC encoding aspartate,
   TGC encoding cysteine,
   AGG encoding arginine,
   GGC encoding glycine, and
   GAG encoding glutamate;
   (v) the portion that is codon optimized is CpG free;
   (vi) the polynucleotide further comprises a transcription regulatory element comprising:
      (a) a promoter comprising a sequence that is at least 98% identical to SEQ ID NO. 14; and
      (b) an enhancer comprising a sequence that is at least 98% identical to SEQ ID NO. 13; and
   (vii) the Factor IX nucleotide sequence comprises a codon that encodes leucine at a position corresponding to position 384 of SEQ ID NO. 16.

2. The method of claim 1, wherein:
   (i) the haemophilia is haemophilia B; or
   (ii) the patient has antibodies or inhibitors to Factor IX.

3. The method of claim 1, wherein a polypeptide encoded by the Factor IX nucleotide sequence is expressed in human liver cells at higher levels compared to a polypeptide encoded by a reference wild type Factor IX nucleotide sequence.

4. The method of claim 1, wherein the portion of the coding sequence that is codon optimized comprises at least a portion of exon 3, at least a portion of exon 4, at least a portion of exon 5, at least a portion of exon 6, at least a portion of exon 7, and at least a portion of exon 8.

5. The method of claim 1, wherein in the portion of the coding sequence that is codon optimized, the codon optimization is selected from the group consisting of:
  (i) a) at least 1 of the codons that encode phenylalanine are replaced with TTC compared to a reference wild type Factor IX sequence;
    b) at least 60% of the codons that encode phenylalanine are TTC;
    c) at least 60% of the codons that encode phenylalanine are TTC and the remainder are TTT; or
    d) the codons that encode phenylalanine are TTC, except where the following codon starts with a G;
  (ii) a) at least 5 of the codons that encode leucine are replaced with CTG compared to a reference wild type Factor IX sequence;
    b) at least 90% of the codons that encode leucine are CTG; or
    c) at least 90% of the codons that encode leucine are CTG and the remainder are CTC;
  (iii) a) at least 5 of the codons that encode isoleucine are replaced with ATC compared to a reference wild type Factor IX sequence;
    b) at least 1 of the ATC codons that encode isoleucine are replaced with ATT compared to a reference wild type Factor IX sequence, where the following codon starts with a G;
    c) at least 60% of the codons that encode isoleucine are ATC;
    d) at least 60% of the codons that encode isoleucine are ATC and the remainder are ATT; or
    e) the codons that encode isoleucine are ATC, except where the following codon starts with a G;
  (iv) a) at least 10 of the codons that encode valine are replaced with GTG compared to a reference wild type Factor IX sequence;
    b) at least 1 of the codons that encodes valine are replaced with GTC compared to a reference wild type Factor IX sequence;
    c) at least 80% of the codons that encode valine are GTG; or
    d) at least 80% of the codons that encode valine are GTG and the remainder are GTC;
  (v) a) at least 5 of the codons that encode serine are replaced with AGC compared to a reference wild type Factor IX sequence;
    b) at least 1 of the codons that encode serine are replaced with TCT compared to a reference wild type Factor IX sequence, where the following codon starts with a G;
    c) at least 60% of the codons that encode serine are AGC; or
    d) at least 60% of the codons that encode serine are AGC and the remainder are TCT or TCC;
  (vi) a) at least 1 of the codons that encode proline are replaced with CCC compared to a reference wild type Factor IX sequence;
    b) at least 1 of the codons that encode proline are replaced with CCT compared to a reference wild type Factor IX sequence, where the following codon starts with a G;
    c) at least 50% of the codons that encode proline are CCC;
    d) at least 50% of the codons that encode proline are CCC and the remainder are CCA or CCT; or
    e) the codons that encode proline are CCC, except where the following codon starts with a G;
  (vii) a) at least 6 of the codons that encode threonine are replaced with ACC compared to a reference wild type Factor IX sequence;
    b) at least 1 of the codons that encode threonine are replaced with ACT compared to a reference wild type Factor IX sequence, where the following codon starts with a G;
    c) at least 45% of the codons that encode threonine are ACC;
    d) at least 45% of the codons that encode threonine are ACC and the remainder are ACT; or
    e) the codons that encode threonine are ACC, except where the following codon starts with a G;
  (viii) a) at least 1 of the codons that encode alanine are replaced with GCC compared to a reference wild type Factor IX sequence;
    b) at least 1 of the codons that encode alanine are replaced with GCT compared to a reference wild type Factor IX sequence, where the following codon starts with a G;
    c) at least 35% of the codons that encode alanine are GCC;
    d) at least 35% of the codons that encode alanine are GCC and the remainder are GCT; or
    e) the codons that encode alanine are GCC, except where the following codon starts with a G;
  (ix) a) at least 1 of the codons that encode tyrosine are replaced with TAC compared to a reference wild type Factor IX sequence;
    b) at least 1 of the TAC codons that encode tyrosine are replaced with TAT compared to a reference wild type Factor IX sequence, where the following codon starts with a G;
    c) at least 40% of the codons that encode tyrosine are TAC;
    d) at least 40% of the codons that encode tyrosine are TAC and the remainder are TAT; or
    e) the codons that encode tyrosine are TAC, except where the following codon starts with a G;
  (x) a) at least 1 of the codons that encode histidine are replaced with CAC compared to a reference wild type Factor IX sequence;
    b) at least 50% of the codons that encode histidine are CAC;
    c) at least 50% of the codons that encode histidine are CAC and the remainder are CAT; or
    d) the codons that encode histidine are CAC, except where the following codon starts with a G;
  (xi) a) at least 1 of the codons that encode glutamine are replaced with CAG compared to a reference wild type Factor IX sequence;
    b) at least 1 of the CAG codons are replaced with CAA compared to a reference wild type Factor IX sequence;
    c) at least 80% of the codons that encode glutamine are CAG; or d) at least 80% of the codons that encode glutamine are CAG and the remainder are CAA;
(xii) a) at least 1 of the codons that encode asparagine are replaced with AAC compared to a reference wild type Factor IX sequence;
b) at least 60% of the codons that encode asparagine are AAC;
c) at least 60% of the codons that encode asparagine are AAC and the remainder are AAT; or
d) the codons that encode asparagine are AAC, except where the following codon starts with a G;
(xiii) a) at least 5 of the codons that encode lysine are replaced with AAG compared to a reference wild type Factor IX sequence;
b) at least 1 of the AAG codons are replaced with AAA compared to a reference wild type Factor IX sequence;
c) at least 80% of the codons that encode lysine are AAG; or
d) at least 80% of the codons that encode lysine are AAG and the remainder are AAA;
(xiv) a) at least 1 of the codons that encode aspartate are replaced with GAC compared to a reference wild type Factor IX sequence;
b) at least 1 of the GAC codons are replaced with GAT compared to a reference wild type Factor IX sequence, where the following codon starts with a G;
c) at least 45%, of the codons that encode aspartate are GAC;
d) at least 45% of the codons that encode aspartate are GAC and the remainder are GAT; or
e) the codons that encode aspartate are GAC, except where the following codon starts with a G;
(xv) a) at least 15 of the codons that encode glutamate are replaced with GAG compared to a reference wild type Factor IX sequence;
b) at least 80% of the codons that encode glutamate are GAG; or
c) at least 80% of the codons that encode glutamate are GAG and the remainder are GAA;
(xvi) a) at least 5 of the codons that encode cysteine are replaced with TGC compared to a reference wild type Factor IX sequence;
b) at least 1 of the TGC codons are replaced with TGT compared to a reference wild type Factor IX sequence, where the following codon starts with a G;
c) at least 40% of the codons that encode cysteine are TGC;
d) at least 40% of the codons that encode cysteine are TGC and the remainder are TGT; or
e) the codons that encode cysteine are TGC, except where the following codon starts with a G;
(xvii) a) at least 5 of the codons that encode arginine are replaced with AGG compared to a reference wild type Factor IX sequence;
b) at least 1 of the codons that encodes arginine are replaced with AGA compared to a reference wild type Factor IX sequence;
c) at least 60% of the codons that encode arginine are AGG; or
d) at least 60% of the codons that encode arginine are AGG and the remainder are AGA; and
(xviii) a) at least 5 of the codons that encode glycine are replaced with GGC compared to a reference wild type Factor IX sequence;
b) at least 5 of the codons that encode glycine are replaced with GGG compared to a reference wild type Factor IX sequence, where the following codon starts with a G;
c) at least 50% of the codons that encode glycine are GGC;
d) at least 50% of the codons that encode glycine are GGC and the remainder are GGG; or
e) the codons that encode glycine are GGC, except where the following codon starts with a G.

6. The method of claim 1, wherein the portion of the coding sequence that is codon optimized comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimized portion:
a) at least 70% of the codons that encode phenylalanine are TTC;
b) at least 94% of the codons that encode leucine are CTG;
c) at least 75% of the codons that encode isoleucine are ATC;
d) at least 95% of the codons that encode valine are GTG;
e) at least 70% of the codons that encode serine are AGC;
f) at least 60% of the codons that encode proline are CCC;
g) at least 55% of the codons that encode threonine are ACC;
h) at least 43% of the codons that encode alanine are GCC;
i) at least 48% of the codons that encode tyrosine are TAC;
j) at least 65% of the codons that encode histidine are CAC;
k) at least 90% of the codons that encode glutamine are CAG;
l) at least 70% of the codons that encode asparagine are AAC;
m) at least 95% of the codons that encode lysine are AAG;
n) at least 60% of the codons that encode aspartate are GAC;
o) at least 95% of the codons that encode glutamate are GAG;
p) at least 55% of the codons that encode cysteine are TGC;
q) at least 75% of the codons that encode arginine are AGG; and
r) at least 60% of the codons that encode glycine are GGC.

7. The method of claim 1, wherein the portion of the coding sequence that is codon optimised comprises codons encoding phenylalanine, leucine, isoleucine, valine, serine, proline, threonine, alanine, tyrosine, histidine, glutamine, asparagine, lysine, aspartate, glutamate, cysteine, tryptophan, arginine, and glycine, and in the codon optimized portion:
a) at least 70% of the codons that encode phenylalanine are TTC and the remainder are TTT;
b) at least 94% of the codons that encode leucine are CTG and the remainder are CTC;
c) at least 75% of the codons that encode isoleucine are ATC and the remainder are ATT;
d) at least 95% of the codons that encode valine are GTG;
e) at least 70% of the codons that encode serine are AGC;
f) at least 60% of the codons that encode proline are CCC and the remainder are CCA or CCT;
g) at least 55% of the codons that encode threonine are ACC and the remainder are ACT;

h) at least 43% of the codons that encode alanine are GCC and the remainder are GCT;
i) at least 48% of the codons that encode tyrosine are TAC and the remainder are TAT;
j) at least 65% of the codons that encode histidine are CAC and the remainder are CAT;
k) at least 90% of the codons that encode glutamine are CAG and the remainder are CAA;
l) at least 70% of the codons that encode asparagine are AAC and the remainder are AAT;
m) at least 95% of the codons that encode lysine are AAG and the remainder are AAA;
n) at least 60% of the codons that encode aspartate are GAC and the remainder are GAT;
o) at least 95% of the codons that encode glutamate are GAG and the remainder are GAA;
p) at least 55% of the codons that encode cysteine are TGC and the remainder are TGT;
q) at least 75% of the codons that encode arginine are AGG and the remainder are AGA; and
r) at least 60% of the codons that encode glycine are GGC and the remainder are GGG.

8. The method of claim 1, wherein the enhancer:
(i) comprises a sequence having at least 99% identity to SEQ ID NO. 13; or
(ii) comprises a sequence of SEQ ID NO. 13.

9. The method of claim 1, wherein the promoter:
(i) comprises a sequence having at least 99% identity to SEQ ID NO. 14; or
(ii) comprises a sequence of SEQ ID NO. 14.

10. The method of claim 1, wherein the codon that encodes leucine at a position corresponding to position 384 of SEQ ID NO. 16 is CTC or CTG.

11. The method of claim 1, wherein the codon that encodes leucine at a position corresponding to position 384 of SEQ ID NO. 16 is CTX, wherein X is any nucleotide.

12. The method of claim 3, wherein the reference wild type Factor IX nucleotide sequence is SEQ ID NO. 9.

13. The method of claim 5, wherein the reference wild type Factor IX nucleotide sequence is SEQ ID NO. 9.

14. The method of claim 1, wherein the administering comprises administering an AAV viral particle comprising a recombinant genome comprising the polynucleotide.

15. The method of claim 14, wherein the AAV viral particle expresses the Factor IX protein having an activity greater after transduction into a population of Huh7 cells than the activity of a Factor IX protein expressed from a comparable AAV viral particle comprising a Factor IX nucleotide sequence of SEQ ID NO: 12 and a transcription regulatory element of SEQ ID NO. 7 transduced into a comparable population of Huh7 cells.

16. The method of claim 1, wherein the polypeptide encoded by the Factor IX nucleotide sequence has a higher activity compared to a polypeptide encoded by a reference wild type Factor IX nucleotide sequence, wherein the activity is measured by a chromogenic assay.

17. The method of claim 1, wherein (iv) the portion of the coding sequence that is codon optimized comprises at least 19 codons encoding phenylalanine, at least 20 codons encoding leucine, at least 21 codons encoding isoleucine, at least 34 codons encoding valine, at least 24 codons encoding serine, at least 15 codons encoding proline, at least 28 codons encoding threonine, at least 20 codons encoding alanine, at least 14 codons encoding tyrosine, at least 9 codons encoding histidine, at least 12 codons encoding glutamine, at least 26 codons encoding asparagine, at least 25 codons encoding lysine, at least 18 codons encoding aspartate, at least 36 codons encoding glutamate, at least 21 codons encoding cysteine, at least 8 codons encoding tryptophan, at least 15 codons encoding arginine, at least 1 codon encoding methionine, and at least 32 codons encoding glycine.

18. The method of claim 1, wherein, in the portion of the coding sequence that is codon optimized, at least 75% of the codons that encode arginine are AGG.

19. The method of claim 14, wherein the recombinant genome is not packaged in self-complementary configuration.

20. The method of claim 14, wherein the recombinant genome further comprises:
a) AAV2 ITRs;
b) a poly A sequence;
c) an origin of replication; and/or
d) two resolvable ITRs.

21. The method of claim 1, wherein in the portion that is codon optimized:
(a) the codons that encode phenylalanine are TTC, except where the following codon starts with a G;
(b) the codons that encode isoleucine are ATC, except where the following codon starts with a G;
(c) the codons that encode threonine are ACC, except where the following codon starts with a G;
(d) the codons that encode alanine are GCC, except where the following codon starts with a G;
(e) the codons that encode tyrosine are TAC, except where the following codon starts with a G;
(f) the codons that encode histidine are CAC, except where the following codon starts with a G;
(g) the codons that encode asparagine are AAC, except where the following codon starts with a G;
(h) the codons that encode aspartate are GAC, except where the following codon starts with a G;
(i) the codons that encode cysteine are TGC, except where the following codon starts with a G; and
(j) the codons that encode glycine are GGC, except where the following codon starts with a G.

22. The method of claim 1, wherein the Factor IX nucleotide sequence comprises a coding sequence that encodes a Factor IX protein of SEQ ID NO.8.

23. A method of treating a haemophilia patient in need thereof, the method comprising administering an effective amount of a polynucleotide comprising a Factor IX nucleotide sequence to the patient, wherein:
(i) the Factor IX nucleotide sequence comprises a coding sequence that encodes a Factor IX protein of SEQ ID NO. 8;
(ii) a portion of the coding sequence is codon optimized;
(iii) the portion of the coding sequence that is codon optimized is at least 1100 nucleotides in length;
(iv) in the portion that is codon optimized at least 73% of the codons are selected from the group consisting of:
TTC encoding phenylalanine,
CTG encoding leucine,
ATC encoding isoleucine,
GTG or GTC encoding valine,
AGC encoding serine,
CCC encoding proline,
ACC encoding threonine,
GCC encoding alanine,
TAC encoding tyrosine,
CAC encoding histidine,
CAG encoding glutamine,
AAC encoding asparagine,
AAA or AAG encoding lysine, GAC encoding aspartate,
TGC encoding cysteine,
AGG encoding arginine,
GGC encoding glycine, and
GAG encoding glutamate; further wherein:
(a) the codons that encode phenylalanine are TTC, except where the following codon starts with a G;
(b) the codons that encode isoleucine are ATC, except where the following codon starts with a G;
(c) the codons that encode threonine are ACC, except where the following codon starts with a G;
(d) the codons that encode alanine are GCC, except where the following codon starts with a G;
(e) the codons that encode tyrosine are TAC, except where the following codon starts with a G;
(f) the codons that encode histidine are CAC, except where the following codon starts with a G;
(g) the codons that encode asparagine are AAC, except where the following codon starts with a G;
(h) the codons that encode aspartate are GAC, except where the following codon starts with a G;
(i) the codons that encode cysteine are TGC, except where the following codon starts with a G; and
(j) the codons that encode glycine are GGC, except where the following codon starts with a G;

(v) the portion that is codon optimized is CpG free;
(vi) the polynucleotide further comprises a transcription regulatory element comprising:
(a) a promoter comprising a sequence that is at least 98% identical to SEQ ID NO. 14; and
(b) an enhancer comprising a sequence that is at least 98% identical to SEQ ID NO. 13; and
(vii) the Factor IX nucleotide sequence comprises a codon that encodes leucine at a position corresponding to position 384 of SEQ ID NO. 16 which is CTX, wherein X is any nucleotide.

24. The method of claim 23, wherein the administering comprises administering an AAV particle comprising a recombinant genome comprising the polynucleotide, and the recombinant genome:
(i) is not packaged in self-complementary configuration; and
(ii) further comprises:
a) AAV2 ITRs;
b) a poly A sequence;
c) an origin of replication; and/or
d) two resolvable ITRs.

* * * * *